United States Patent
Dueber et al.

(10) Patent No.: US 12,098,405 B2
(45) Date of Patent: Sep. 24, 2024

(54) PROTECTING GROUP CHEMISTRY FOR CLEAN, REDUCTANT-FREE DYEING

(71) Applicant: The Regents of the University of California, Oakland, CA (US)

(72) Inventors: John Eugene Dueber, San Francisco, CA (US); Zachary Nicholas Russ, Darnestown, MD (US); Tammy Melody Hsu, Palo Alto, CA (US); Terry Don Johnson, Jr., Oakland, CA (US); Bernardo Cervantes, Berkeley, CA (US); Ramya Lakshmi Prathuri, Cupertino, CA (US); Shyam Pravin Bhakta, Humble, TX (US); Arthur Muir Fong, III, Sacramento, CA (US); Luke Nathaniel Latimer, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 206 days.

(21) Appl. No.: 17/522,523

(22) Filed: Nov. 9, 2021

(65) Prior Publication Data

US 2022/0136024 A1 May 5, 2022

Related U.S. Application Data

(60) Division of application No. 16/842,401, filed on Apr. 7, 2020, now Pat. No. 11,203,774, which is a continuation of application No. 15/555,026, filed as application No. PCT/US2016/020729 on Mar. 3, 2016, now Pat. No. 10,704,070.

(60) Provisional application No. 62/127,778, filed on Mar. 3, 2015.

(51) Int. Cl.
| | | |
|---|---|---|
| *C12N 9/00* | (2006.01) | |
| *C09B 7/02* | (2006.01) | |
| *C09B 7/04* | (2006.01) | |
| *C12N 9/02* | (2006.01) | |
| *C12N 9/10* | (2006.01) | |
| *C12N 9/14* | (2006.01) | |
| *C12P 17/16* | (2006.01) | |
| *C12P 19/60* | (2006.01) | |

(52) U.S. Cl.
CPC ............... *C12P 19/60* (2013.01); *C09B 7/02* (2013.01); *C09B 7/04* (2013.01); *C12N 9/0071* (2013.01); *C12N 9/0073* (2013.01); *C12N 9/1051* (2013.01); *C12N 9/13* (2013.01); *C12N 9/14* (2013.01); *C12P 17/165* (2013.01); *C12Y 114/13008* (2013.01); *C12Y 114/14001* (2013.01); *C12Y 204/01115* (2013.01); *C12Y 208/02001* (2013.01)

(58) Field of Classification Search
CPC .............. C09B 7/02; C12Y 114/13008; C12Y 114/14001; C12Y 208/02001; C12Y 204/01115
USPC ........................................................ 435/191
See application file for complete search history.

(56) References Cited

U.S. PATENT DOCUMENTS

| 4,520,103 | A | 5/1985 | Ensley, Jr. |
| 5,494,816 | A | 2/1996 | Murdock |
| 6,656,229 | B1 | 12/2003 | Taguchi et al. |
| 6,962,794 | B2 | 11/2005 | Valle et al. |
| 8,741,602 | B2 | 6/2014 | Ikushiro et al. |
| 2001/0010913 | A1 | 8/2001 | Hillman et al. |

FOREIGN PATENT DOCUMENTS

| CN | 103509819 | 1/2014 |
| KR | 10-2011-0037687 | 4/2011 |
| WO | WO 2006/015961 | 2/2006 |
| WO | WO 2013/022989 | 2/2013 |
| WO | WO 2014/067534 | 5/2014 |
| WO | WO 2014/106189 | 7/2014 |

OTHER PUBLICATIONS

Pathak et al.( Appl biochem., biotech. 2010, 160, pp. 1616-1626.*
Accession No. 2011-E15079, WPI/Thomson, Apr. 13, 2011, 2 pages.
Accession No. PREV201500761707, Biosis, Aug. 2015, 2 pages.
International Preliminary Report on Patentability received for PCT Patent Application No. PCT/US2016/020729, mailed on Sep. 14, 2017, 12 pages.
International Search Report and Written Opinion received for PCT Patent Application No. PCT/US2016/020729, mailed on Aug. 1, 2016, 21 pages.
Invitation to Pay Additional Fees received for PCT Patent Application No. PCT/US2016/020729, mailed on May 24, 20-16, 8 pages.
Altschul et al., "Basic Local Alignment Search Tool", „Journal oi Molecular Biology, vol. 215, 1990, pp. 403-410.
Altschul et al., "Gapped BLAST and PSI-BLAST: A New Generation of Protein Database Search Programs", Nucleic Acids Research, vol. 25, No. 17, 1997, pp. 3389-3402.

(Continued)

*Primary Examiner* — Robert B Mondesi
*Assistant Examiner* — Mohammad Y Meah
(74) *Attorney, Agent, or Firm* — James J. Diehl; Bozicevic, Field & Francis LLP

(57) ABSTRACT

The present disclosure relates to the biosynthesis of indigoid dye precursors and their conversion to indigoid dyes. Specifically, the present disclosure relates to methods of using polypeptides to produce indigoid dye precursors from indole feed compounds, and the use of the indigoid dye precursors to produce indigoid dyes.

23 Claims, 7 Drawing Sheets

Specification includes a Sequence Listing.

(56) References Cited

OTHER PUBLICATIONS

Banoglu et al., "Sulfation of indoxyl by human and rat aryl (phenol) sulfotransferases to form indoxyl sulfate", Eur J Drug Metab Pharmacokinet. Vol. 27, No. 2, 2002, 10 pages.
Beil et al., "Purification and characterization of the arylsulfatase synthesized by Pseudomonas aeruginosa PAO during growth in sulfate-free medium and cloning of the arylsulfatase gene (atsA)", Eur. J. Biochem. vol. 229, 1995, pp. 385-394.
Berger et al., "The Molecular Basis for the Broad Substrate Specificity of Human Sulfotransferase 1A1", PLoS One, vol. 6, Issue 11, Nov. 2011, 10 pages.
Berry, et al.; "Application of metabolic engineering to improve both the production and use of biotech indigo"; Journal of Industrial Microbiology & Biotechnology; vol. 28, pp. 127-133 (2002).
Blackburn et al., "The Development of Indigo Reduction Methods And Pre-Reduced Indigo Products", Color. Technol., vol. 125, 2009, pp. 193-207.
Bolger et al., "Trimmomatic: A Flexible Trimmer For Iliumina Sequence Data", Bioinformatics, vol. 30, No. 15, 2014, pp. 2114-2120.
Bonde et al., Modest: A Web-based Design Tool for Oligonucleotide-mediated genome engineering and Recombineering, Nucleic Acids Research, vol. 42, 2014, pp. W408-W415.
Choi et al., "A Novel Flavin-Containing Monooxygenase from *Methylophaga* sp. Strain sk1 and its Indigo Synthesis in *Escherichia coli*", Biochemical and Biophysical Research Communications, vol. 306, 2003, pp. 930-936.
Corpet, Florence, "Multiple Sequence Alignment with Hierarchical Clustering", Nucleic Acids Research, vol. 16 No. 22, 1988, pp. 10881-10890.
Dealler et al., "Enzymatic Degradation of Urinary Indoxyl Sulfate by Providencia stuartii and Klebsielia pneumoniae Causes the Purple Urine Bag Syndrome", Journal Of Clinical Microbiology, vol. 26, No. 10, 1988, pp. 2152--2156.
Dietrich et al., "A Novel Semi-biosynthetic Route for Artemisinin Production Using Engineered Substrate-Promiscuous P450BM3", ACS Chemical Biology, vol. 4, No. 4, 2009, pp. 261-267.
Eisen, Jonathan A., "Phylogenomics: Improving Functional Predictions for Uncharacterized Genes by Evolutionary Analysis", Genome Research, vol. 8, 1998, pp. 163-167.
Eng et al., "An Approach to Correlate Tandem Mass Spectral Data of Peptides with Amino Acid Sequences in a Protein Database", Journal American Society for Mass Spectrom, vol. 5, 1994, pp. 976-989.
Enomoto et al., "Role of Organic Anion Transporters in the Tubular Transport of Indoxyl Sulfate and the Induction of its Nephrotoxicity", Journal of the American Society of Nephrology, vol. 13, 2002, pp. 1711-1720.
Feng et al., "Progressive Sequence Alignment as a Prerequisite to Correct Phylogenetic Trees", Journal of Molecular Evolution, vol. 25, 1987, pp. 351-360.
Gietz et al., "High-Efficiency Yeast Transformation Using the LiAc/SS Carrier DNA/PEG method", Nature Protocols, vol. 2, No. 1, 2007, pp. 31-34.
Gillam et al., "Exploiting the Versatility of Human Cytochrome P450 Enzymes: The Promise of Blue Roses From Biotechnology", IUBMB Life, vol. 52, 2001, pp. 271-277.
Haas et al., "De Novo Transcript Sequence Reconstruction from RNA-seq using the Trinity Platform for Reference Generation and Analysis", Nature Protocols, vol. 8, No. 8, 2013, pp. 1494-1512.
Han et al., "Enhanced Indirubin Production In Recombinant *Escherichia coli* Harboring A Flavin-Containing Monooxygenase Gene By Cysteine Supplementation", Journal of Biotechnology, vol. 164, 2012, pp. 179-187.
Harayama et al. (1992). "Functional and Evolutionary Relationships Among Diverse Oxygenases," Annu. Rev. Microbiol., 46:565-601.
Higgins et al., "Clustal: A Package for Performing Multiple Sequence Alignment on a Microcomputer", Gene, vol. 73, 1988, pp. 237-244.
Higgins et al., "Fast and Sensitive Multiple Sequence Alignments on a Microcomputer", Cabios Communications, vol. 5, No. 2, 1989, pp. 151-153.
Higgins et al., "Using Clustal for Multiple Sequence Alignments", Methods In Enzymology, vol. 266, 1996, pp. 383-402.
Huang et al., "Parallelization of a Local Similarity Algorithm", Cabios, vol. 8, No., 2, 1992, pp. 155-165.
Karlin et al., "Applications and Statistics for Multiple High-Scoring Segments in Molecular Sequences", Proceedings of the National Academy of Sciences, vol. 90, Jun. 1993, pp. 5873-5877.
Kim et al., "Analysis of Cellodextrin Transporters from Neurospora Crassa in *Saccharomyces cerevisiae* for Cellobiose Fermentation", Applied Microbiology And Biotechnology, vol. 98, 2014, pp. 1087-1094.
Kimmel, Alan R., "Identification and Characterization of Specific Clones: Strategy for Confirming the Validity of Presumptive Clones", Methods In Enzymology, vol. 152, 1987, pp. 507-511.
Liang et al. (2015). "Glycosyltransferases: Mechanisms and Applications in Natural Product Development," Chemical Society Reviews, 44:8350-8374.
Lojda, Zdenek, "Indigogenic Methods for Glycosidases: I. An Improved Method for β-D—glucosidase and its Application to Localization Studies of Intestinal and Renal Enzymes", Histochemie, vol. 22, 1970, pp. 347-361.
Magoc et al., "FLASH: Fast Length Adjustment Of Short Reads To Improve Genome Assemblies", vol. 27, No. 21, 2011, pp. 2957-2963.
Mao et al., "Engineering the *E. coli* UDP-Glucose Synthesis Pathway for Oligosaccharide Synthesis", Biotechnol. Prog. Vol. 22, No. 2, 2006, pp. 369-374.
Marcinek et al., "Indoxyl-UDPG-glucosyltransferase from Baphicacanthus cusia", Phytochemistry, vol. 53, 2000, pp. 201-207.
Maugard et al., "β-Glucosidase-Catalyzed Hydrolysis of Indican from Leaves of Polygonum tinctorium", Biotechnol. Prog. vol. 18, No. 5, 2002, pp. 1104-1108.
Minami et al., "Tissue and Intracellular Localization of Indican and the Purification and Characterization of Indican Synthase from Indigo Plants", Plant Cell Physiol. vol. 41, No. 2, 2000, pp. 218-225.
Mount, David W., "Sequence and Genome Analysis", Cold Spring Harbor Laboratory Press, 2001, p. 543.
Murdock, et al.; "Construction of Metabolic Operons Catalyzing the De Novo Biosynthesis of Indigo in *Escherichia coli*"; Bio/Technology; vol. 11, pp. 381-386 (Mar. 11, 1993).
Myers et al., "Optimal Alignments in Linear Space", Cabios, vol. 4, No. 1, 1988, pp. 11-17.
Needleman et al., "A General Method Applicable to the Search for Similarities in the Amino Acid Sequence of Two Proteins", Journal of Molecular Biology, vol. 48, 1970, pp. 443-453.
Paavilainen et al., "Purification, Characterization, Gene Cloning, and Sequencing of a New ß-Glucosidase from *Bacillus circulans* subsp. *alkalophilus*", Applied And Environmental Microbiology, vol. 59, No. 3, Mar. 1993, pp. 927-932.
Paul et al. (2012). "Recent advances in sulfotransferase enzyme activity assays," Anal Bioanal Chem., 403(6):1491-1500.
Pearson et al., "Improved Tools for Biological Sequence Comparison", Proceedings of the National Academy of Sciences, vol. 85, Apr. 1988, pp. 2444-2448.
Pearson, William R., "Using the FASTA Program to Search Protein and DNA Sequence Databases", Methods in Molecular Biology, vol. 24, 1994, pp. 307-331.
Prathuri, Ramya, "oleD glucosyltransferase: S. antibiotics (characterized)", Registry of Standard Biological Parts, Part :BBa K1131006, Oct. 28, 2013, pp. 1-2.
Rioz-Martinez et al., "Exploring the biocatalytic scope of a bacterial flavin-containing monooxygenase", Organic & Biomolecular Chemistry, vol. 9, 2011, pp. 1337-1341.
Rossi et al., "Sulfate assimilation pathway intermediate phosphoadenosine 5-phosphosulfate acts as a signal molecule affecting production of curli fibres in Escherichia coli", Microbiology, vol. 160, 2014, pp. 1832-1844.
Saigo et al., "Meclofenamate elicits a nephropreventing effect in a rat model of ischemic acute kidney injury by suppressing indoxyl

(56) References Cited

OTHER PUBLICATIONS sulfate production and restoring renal organic anion transporters", Drug Design, Development and Therapy, vol. 8, 2014, pp. 1073-1082.

Saitou et al., "The Neighbor-Joining Method: A New Method for Reconstructing Phylogenetic Trees1", Mol. Biol. Evol., vol. 4, No. 4, 1987, pp. 406-425.

Sandermann, Jr. Heinrich, "β-D-Galactoside Transport in *Escherichia coli*: Substrate Recognition", Eur. ,J. Biochem. vol. 80, 1977, pp. 507-515.

Simkhada et al., "Exploration of Glycosylated Flavonoids from Metabolically Engineered *E.coli*", Biotechnology and Bioprocess Engineering, vol. 15, 2010, pp. 754-760.

Smith et al., "Comparison of Biosequences", Advances in Applied Mathematics, vol. 2, 1981, pp. 482-489.

Song et al., "Development of a Highly Efficient Indigo Dyeing Method using Indican with an Immobilized β-Glucosidase from Aspergillus Niger", Journal of Bioscience and Bioengineering, vol. 110, No. 3, 2010, pp. 281-287.

Tabb et al., "DTASelect and Contrast: Tools for Assembling and Comparing Protein Identifications from Shotgun Proteomics", J Proteome Res. vol. 1, No. 1, 2002, 14 pages.

Tamura et al., "MEGA4: Molecular Evolutionary Genetics Analysis (MEGA) Software Version 4.0", Mol. Biol. Evol., vol. 24, No. 8, 2007, pp. 1596-1599.

Thompson et al., "Clustal W: Improving the Sensitivity of Progressive Multiple Sequence Alignment through Sequence Weighting, Position-Specific Gap Penalties and Weight Matrix Choice", Nucleic Acids Research, vol. 22, No. 22, 1994, pp. 4673-4680.

Wahl et al., "Molecular Hybridization of Immobilized Nucleic Acids: Theoretical Concepts and Practical Considerations", Methods In Enzymology, vol. 152, 1987, pp. 399-407.

Wang et al., "Programming cells by multiplex genome engineering and accelerated evolution", Nature, vol. 460, Aug. 13, 2009, pp. 894-898.

Warzecha et al., "Formation of the indigo precursor indican in genetically engineered tobacco plants and cell cultures", Plant Biotechnology Journal, vol. 5, 2007, pp. 185-191.

Yuan et al., "Biooxidation of indole and characteristics oi the responsible enzymes", African Journal of Biotechnology, vol. 10, No. 86, Dec. 30, 2011, pp. 19855-19863.

Zuckerkandl et al., "Evolutionary Divergence and Convergence, in Proteins.", In Evolving Genes and Proteins, 1965, pp. 97-166.

\* cited by examiner

*before glucosidase application* indigo indican

*5 min incubation with glucosidase* indigo indican

*6 h + washing and drying* indigo indican

A: 5,5'-dichloro-[2,2'-biindolinylidene]-3,3'-dione
B: 6,6'-dichloro-[2,2'-biindolinylidene]-3,3'-dione
C: 7,7'-dichloro-[2,2'-biindolinylidene]-3,3'-dione
D: 5,5'-dibromo-[2,2'-biindolinylidene]-3,3'-dione
E: 6,6'-dibromo-[2,2'-biindolinylidene]-3,3'-dione
F: 7,7'-dibromo-[2,2'-biindolinylidene]-3,3'-dione

PROTECTING GROUP CHEMISTRY FOR CLEAN, REDUCTANT-FREE DYEING

CROSS REFERENCE TO RELATED APPLICATIONS

This application is a Division of U.S. patent application Ser. No. 16/842,401, filed Apr. 7, 2020, U.S. patent Ser. No. 11/203,774, which is continuation of U.S. patent application Ser. No. 15/555,026, filed Aug. 31, 2017, U.S. patent Ser. No. 10/704,070, which is a national stage filing under 35 U.S.C. § 371 of PCT/US2016/020729, filed Mar. 3, 2016, which claims the benefit of U.S. Prov. App. No. 62/127,778, filed on Mar. 3, 2015, each of which applications is hereby incorporated by reference in its entirety.

FIELD

The present disclosure relates generally to the production of dye precursors, and more specifically to the use of polypeptides to produce indigoid dye precursors.

BACKGROUND

The blue dye indigo, produced by some plants, is one of the oldest dyes in the world. It is still a widely used textile dye, particularly in the denim clothing industry. Modern indigo is no longer sourced from plants, but is produced synthetically, mostly from petroleum. Indigo itself is a water-insoluble compound. In order to dye denim, indigo must be treated with a reducing agent to produce an unstable, water-soluble intermediate. After application of this intermediate to the fabric, the fabric is exposed to air and the intermediate oxidizes back to indigo, crystallizing within the fabric fibers. The most common reducing agent used for this process is sodium dithionite, which has many limitations. Sodium dithionite is unstable; can over-reduce the indigo, destroying the dye; is required in excess quantities; and its use produces large amounts of sulfate and sulfite which are detrimental to the environment. Because of these shortcomings, substantial amounts of sodium dithionite are lost to byproducts and degradation during the dyeing process.

The biosynthesis of natural indigo in plants proceeds through a different synthetic pathway. An indigo precursor compound is produced and stored in the plant, then converted to indoxyl, which spontaneously dimerizes to form indigo. However, the quantity and variety of indigo precursors that can be produced through current natural biological pathways is limited.

Thus, there exists a need for new methods to produce indigoid dye precursors with greater structural variety and which can be used to produce indigoid dyes without a harsh reductant chemical.

BRIEF SUMMARY

In one aspect, the present disclosure relates to methods of producing indigoid dye precursors from indole feed compounds. In some aspects, the present disclosure relates to the use of polypeptides to produce indigoid dye precursors from indole feed compounds.

In one aspect, the present disclosure relates to a method of producing a compound of Formula (A), the method comprising:

a) contacting a host cell with a compound of Formula (II); and
b) culturing the host cell under conditions such that a compound of Formula (A) is produced from at least a portion of the compound of Formula (II);
wherein the host cell comprises a single or multiple recombinant nucleic acid(s) encoding:
  i) a polypeptide with oxygenase activity; and
  ii) a polypeptide with glycosyltransferase activity or a polypeptide with sulfotransferase activity, or a combination thereof;
wherein the compound of Formula (A) is:

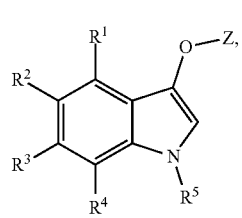

(A)

wherein:
  $R^1$, $R^2$, $R^3$, and $R^4$ are independently selected from H, halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and alkyl;
    wherein alkyl may be unsubstituted or substituted with one or more substituents independently selected from the group consisting of halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and —R$^a$OR$^d$;
  $R^5$ is H or alkyl, wherein alkyl is unsubstituted or substituted with one or more substituents independently selected from the group consisting of halo, hydroxyl, =O, —C(O)OR$^b$, —R$^a$C(O)OR$^b$, —R$^a$OC(O)R$^b$, —OR$^a$, —NR$^b$R$^c$, and —R$^a$OR$^d$;
  Z is a glycone, —C(O)R$^b$, or —SO$_3^-$;
  $R^a$ and $R^d$ are independently alkyl;
  $R^b$ and $R^c$ are independently H or alkyl; and
wherein the compound of Formula (II) is:

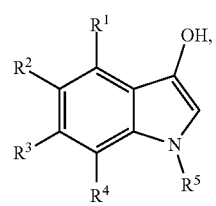

(II)

wherein $R^1$, $R^2$, $R^3$, $R^4$, and $R^5$ are defined as for Formula (A).

In some embodiments, the host cell is a bacterial cell. In some embodiments the host cell is selected from *Escherichia coli* and *Corynebacterium glutamicum*. In other embodiments, the host cell is a yeast. In certain embodiments, the host cell is selected from *Saccharomyces cerevisiae, Pichia pastoris, Kluyveromyces lactis, Kluyveromyces marxianus*, and *Schizosaccharomyces pombe*.

In some embodiments, the polypeptide with glycosyltransferase activity comprises SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20, or the amino acid sequence of any homologs thereof. In some embodiments, the polypeptide with sulfotransferase activity comprises SEQ ID NO: 9, SEQ ID NO: 10, SEQ ID NO: 11, SEQ ID NO: 12, SEQ ID NO: 13, or SEQ ID NO: 14, or the amino acid sequence of any homologs thereof. In some embodiments, the homolog of a polypeptide with oxygenase activity comprises an amino acid sequence at least 90%, at least 95%, or at least 99% identical to an amino acid sequence selected from SEQ ID NO: 1, SEQ ID NO: 2, SEQ ID NO: 21, SEQ ID NO: 22, SEQ ID NO: 23, and SEQ ID NO: 24. In some embodiments, the homolog of a polypeptide with glycosyltransferase comprises an amino acid sequence at least 90%, at least 95%, or at least 99% identical to an amino acid sequence selected from SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, and SEQ ID NO: 20. In some embodiments, the homolog of a polypeptide with sulfotransferase comprises an amino acid sequence at least 90%, at least 95%, or at least 99% identical to an amino acid sequence selected from SEQ ID NO: 9, SEQ ID NO: 10, SEQ ID NO: 11, SEQ ID NO: 12, SEQ ID NO: 13, and SEQ ID NO: 14.

In another aspect, the present disclosure relates to a method of producing a compound of Formula (A) from a compound of Formula (II), further comprising providing a compound of Formula (I):

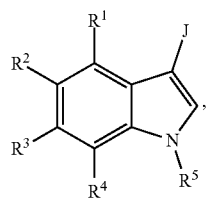

wherein:
$R^1$, $R^2$, $R^3$, $R^4$, and $R^5$ are defined as for Formula (A);
J is alkyl, —OC(O)$R^b$, or phosphate;
wherein alkyl is unsubstituted or substituted with one or more substituents independently selected from the group consisting of halo, hydroxyl, =O, —C(O)O$R^b$, —$R^a$C(O)O$R^b$, —$R^a$OC(O)$R^b$, —O$R^a$, —N$R^b$$R^c$, and —$R^a$O$R^d$; and
$R^a$, $R^b$, $R^c$, and $R^d$ are defined as for Formula (A).

In some embodiments, the titer of the compound of Formula (A) produced according to the methods herein is at least 50 mg/L, 100 mg/L, 1 g/L, 10 g/L, 25 g/L, 50 g/L, 75 g/L, 100 g/L, 125 g/L, 150 g/L, 175 g/L, or 200 g/L.

In some embodiments, the compound of Formula (A) is secreted by the host cell. In certain embodiments, the methods disclosed herein further comprise isolating the compound of Formula (A) produced.

In yet other embodiments, the methods disclosed herein further comprise converting the compound of Formula (A) to a compound of Formula (II).

In another aspect, disclosed herein is a method of producing a compound of Formula (B), the method comprising converting a first compound of Formula (A) and a second compound of Formula (A) to a compound of Formula (B);
wherein the first compound of Formula (A) and the second compound of Formula (A) are the same compound of Formula (A) or different compounds of Formula (A);

at least one of the first compound of Formula (A) and the second compound of Formula (A) is produced according to the methods described herein; and
the compound of Formula (B) is:

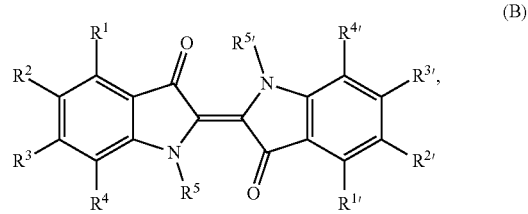

wherein $R^1$, $R^2$, $R^3$, $R^4$, $R^5$, $R^{1\prime}$, $R^{2\prime}$, $R^{3\prime}$, $R^{4\prime}$, and $R^{5\prime}$ are defined as for Formula (A).

In some embodiments, the compound of Formula (A) is converted to a compound of Formula (II); and the compound of Formula (II) is converted to the compound of Formula (B). In certain embodiments, the compound of Formula (A) is contacted by a hydrolase to convert the compound of Formula (A) to the compound of Formula (II). In some embodiments, the hydrolase is a glucosidase, while in other embodiments, the hydrolase is a sulfatase.

In some embodiments of the methods described herein, the polypeptide having oxygenase activity and the polypeptide having glycosyltransferase activity are the same polypeptide. In other embodiments, the polypeptide having oxygenase activity and the polypeptide having sulfotransferase activity are the same polypeptide.

In another aspect, disclosed herein is a host cell comprising single or multiple recombinant nucleic acid(s) encoding a polypeptide with monooxygenase activity and a polypeptide with glucosyltransferase activity.

In yet another aspect, disclosed herein is a host cell comprises a single or multiple recombinant nucleic acid(s) encoding a polypeptide with monooxygenase activity and a polypeptide with sulfotransferase activity.

In a further aspect, the present disclosure relates to a method of producing a compound of Formula (A), the method comprising contacting a compound of Formula (II) with i) a polypeptide with oxygenase activity; and ii) a polypeptide with glycosyltransferase activity or a polypeptide with sulfotransferase activity, or a combination thereof; and producing a compound of Formula (A) from at least a portion of the compound of Formula (II).

In some embodiments that may be combined with any of the preceding embodiments, the compound of Formula (I) is 1H-indol-3-yl and the compound of Formula (A) is 3-(β-D-glucosido)indole. In other embodiments, the compound of Formula (A) is 1H-indol-3-yl sulfate.

In certain embodiments, the present disclosure relates to cDNA encoding the polypeptides described herein, such as cDNAs encoding SEQ ID NOs: 1-29.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
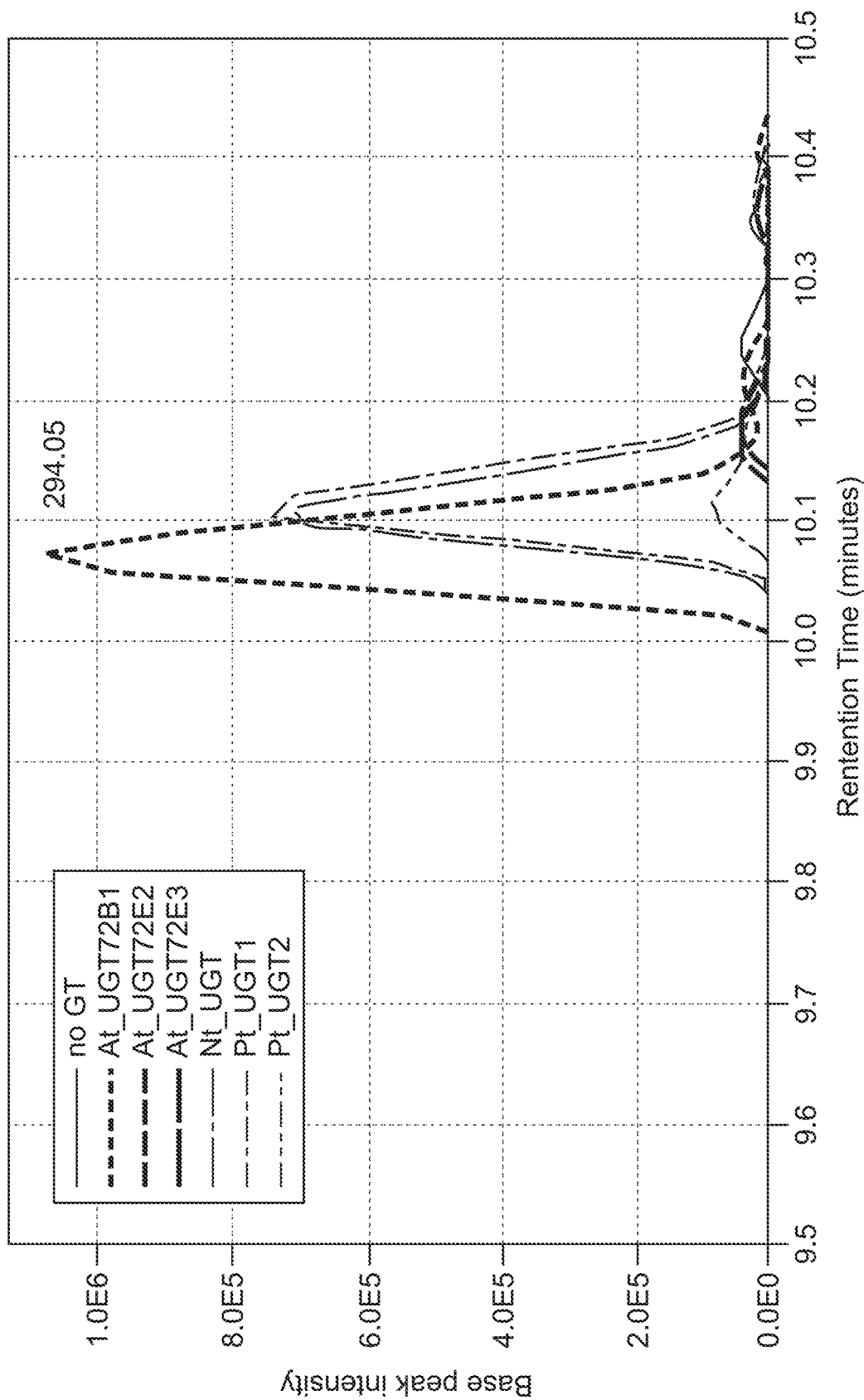
FIG. 1 depicts the high performance liquid chromatography/mass spectrometry (HPLC/MS) trace of 3-(β-D-glucosido)indole (i.e., indican) produced by E. coli host cells heterologously expressing different recombinant glucosyltransferases.

The following description sets forth exemplary methods, parameters and the like. It should be recognized, however, that such description is not intended as a limitation on the scope of the present disclosure but is instead provided as a description of exemplary embodiments.

Methods for Producing Compounds of Formula (A)

The methods described herein provide methods of producing indigoid dye precursors by contacting a feed indole compound with a) a polypeptide with oxygenase activity, and b) a polypeptide with glycosyltransferase activity, a polypeptide with sulfotransferase activity, a polypeptide with acyltransferase activity, or a polypeptide with phosphotransferase activity, or a combination thereof. The polypeptide with oxygenase activity and the polypeptide with glycosyltransferase activity, sulfotransferase activity, acyltransferase activity, or phosphotransferase activity, or a combination thereof, may be the same polypeptide or separate polypeptides. In some embodiments, the feed indole compound is contacted by the polypeptides in a host cell, while in other embodiments, the feed indole compound is contacted by the polypeptides in vitro.

The indigoid dye precursors produced according to the methods described herein may be used to produce indigoid dyes, including, for example, indigo. Thus, in one aspect, provided herein are methods of producing indigoid dyes from the indigoid dye precursors by: a) contacting a feed indole compound with i) a polypeptide with oxygenase activity, and ii) a polypeptide with glycosyltransferase activity, a polypeptide with sulfotransferase activity, a polypeptide with acyltransferase activity, or a polypeptide with phosphotransferase activity, or a combination thereof to produce an indigoid dye precursor; then b) converting the indigoid dye precursor to an indigoid dye.

Compounds of Formula (A): Indigoid Dye Precursors

In one aspect, provided herein are methods of producing indigoid dye precursors by contacting a host cell with a feed indole compound under conditions such that the indigoid dye precursor is produced from at least a portion of the feed indole compound. In certain embodiments the indigoid dye precursor produced is a compound of Formula (A):

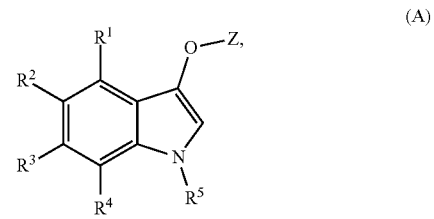

(A)

wherein:
R$^1$, R$^2$, R$^3$, and R$^4$ are independently selected from H, halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and alkyl;
wherein R$^a$ is alkyl; and
R$^b$ and R$^c$ are independently H or alkyl;
R$^5$ is H or alkyl;
Z is glycosyl, —C(O)R$^b$, —SO$_3^-$, or —PO$_3^{2-}$.

In some embodiments of Formula (A), the alkyl of R$^1$, R$^2$, R$^3$, and R$^4$ at each occurrence is independently unsubstituted or substituted with one or more substituents selected from halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and —R$^a$OR$^d$; wherein R$^a$ and R$^d$ are independently alkyl, and R$^b$ and R$^c$ are independently H or alkyl. In certain embodiments, R$^5$ is independently alkyl, and the alkyl is unsubstituted or substituted with one or more substituents selected from halo, hydroxyl, =O, —C(O)OR$^b$, —R$^a$C(O)OR$^b$, —R$^a$OC(O)R$^b$, —OR$^a$, and —NR$^b$R$^c$; wherein R$^a$ is independently alkyl, and R$^b$ and R$^c$ are independently H or alkyl.

In some variations of Formula (A), R$^1$, R$^2$, R$^3$, and R$^4$ are independently H, halo, nitro, hydroxyl, or alkyl. In certain variations, R$^1$, R$^2$, R$^3$, and R$^4$ are independently H, nitro, or hydroxyl. In other variations, R$^1$, R$^2$, R$^3$, and R$^4$ are independently H or nitro. In yet other variations, R$^1$, R$^2$, R$^3$, and R$^4$ are independently H or hydroxyl.

In some variations of the compound of Formula (A), R$^1$, R$^2$, R$^3$, and R$^4$ are independently H, chloro, bromo, iodo, or fluoro. In some variations, R$^1$, R$^2$, R$^3$, and R$^4$ are independently H, chloro, or bromo. In other variations, R$^1$, R$^2$, R$^3$, and R$^4$ are independently H or chloro. In yet other variations, R$^1$, R$^2$, R$^3$, and R$^4$ are independently H or bromo.

In some variations, R$^1$, R$^2$, R$^3$, and R$^4$ are independently H or alkyl. In some embodiments, R$^1$, R$^2$, R$^3$, and R$^4$ are independently H or methyl, ethyl, propyl, butyl, or pentyl. In certain variations $R^1$, $R^2$, $R^3$, and $R^4$ are independently H or methyl.

In certain variations, the alkyl of $R^1$, $R^2$, $R^3$, and $R^4$ at each occurrence is independently unsubstituted or substituted. For example, in certain variations, at least one of $R^1$, $R^2$, $R^3$, and $R^4$ is alkyl, and the alkyl is substituted with halo. In other variations, the alkyl is substituted with hydroxyl. In yet other variations, the alkyl is substituted with $-NR^bR^c$. In other variations, the alkyl is substituted with $-NR^bR^c$ and hydroxyl.

"Alkyl" as used herein refers to refers to a linear or branched saturated hydrocarbon chain. Examples of alkyl groups include methyl, ethyl, n-propyl, iso-propyl, n-butyl, sec-butyl, tert-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl. In some embodiments, alkyl as used herein, such as in compounds of Formulae (A), (B), (I), and (II), has 1 to 30 carbon atoms (i.e., $C_{1-30}$ alkyl), 1 to 20 carbon atoms (i.e., $C_{1-20}$ alkyl), 1 to 15 carbon atoms (i.e., $C_{1-15}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), 1 carbon atom (i.e., $C_1$ alkyl), or 5 to 30 carbon atoms (i.e., $C_{5-30}$ alkyl), or 5 to 20 carbon atoms (i.e., $C_{5-20}$ alkyl).

$R^1$, $R^2$, $R^3$, and $R^4$ may be the same or different. In some embodiments of Formula (A), $R^1$, $R^2$, $R^3$, and $R^4$ are all H. In other embodiments, one of $R^1$, $R^2$, $R^3$, and $R^4$ is nitro; and the remaining $R^1$, $R^2$, $R^3$, and $R^4$ are H. In other embodiments, one of $R^1$, $R^2$, $R^3$, and $R^4$ is halo; and the remaining $R^1$, $R^2$, $R^3$, and $R^4$ are H. In yet other embodiments, two of $R^1$, $R^2$, $R^3$, and $R^4$ are independently halo; and the remaining $R^1$, $R^2$, $R^3$, and $R^4$ are H.

In certain variations of Formula (A), $R^5$ is H. In other variations of Formula (A), $R^5$ is unsubstituted alkyl. For example, in some variations, $R^5$ is unsubstituted methyl, ethyl, propyl, butyl, or pentyl. In certain variations, $R^5$ is methyl. In other variations, $R^5$ is substituted alkyl. For example, in some variations, $R^5$ is alkyl substituted with halo, hydroxyl, =O, $-C(O)OR^b$, $-R^aC(O)OR^b$, $-R^aOC(O)R^b$, $-OR^a$, or $-NR^bR^c$. In certain variations, $R^5$ is ethyl substituted with =O. In one variation, $R^5$ is $-C(O)CH_3$.

In some embodiments of the compound of Formula (A), Z is glycosyl. The term "glycosyl", as used herein, refers to a sugar residue group bonded from the anomeric carbon. The bond from the anomeric carbon may be in the α orientation or the β orientation. In some embodiments, the glycosyl is glucosyl, fructosyl, glucuronosyl, mannosyl, xylosyl, or galactosyl. In certain variations, the glycosyl is glucosyl in which the bond from the anomeric carbon is in the β orientation. In other variations, the glycosyl is glucosyl in which the bond from the anomeric carbon is in the α orientation. In certain variations, the glycosyl is glucuronosyl in which the bond from the anomeric carbon is in the β orientation. In yet other variations, the glycosyl is glucuronosyl in which the bond from the anomeric carbon is in the α orientation.

In other embodiments of the compound of Formula (A), Z is $-C(O)R^b$, wherein $R^b$ is H or alkyl. In some embodiments, Z is $-C(O)R^b$, and $R^b$ is H, methyl, ethyl, propyl, butyl, pentyl, hexyl, heptyl, or octyl. In other embodiments, Z is $-C(O)R^b$, and $R^b$ is H, methyl, ethyl, propyl, or butyl. In certain embodiments, Z is $-C(O)R^b$, and $R^b$ is methyl.

In some embodiments of the compound of Formula (A), Z is $-SO_3^-$ or $-PO_3^{2-}$.

In one variation, $R^1$, $R^2$, $R^3$, $R^4$, and $R^5$ are all H; and Z is glucosyl in which the bond from the anomeric carbon is in the β orientation. Thus, in such a variation, the compound of Formula (A) is:

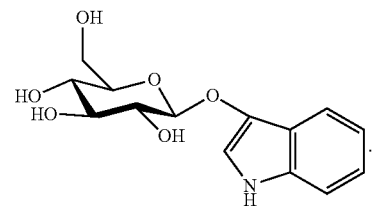

In one variation, $R^1$, $R^2$, $R^3$, $R^4$, and $R^5$ are all H; and Z is glucosyl in which the bond from the anomeric carbon is in the α orientation. Thus, in such a variation, the compound of Formula (A) is:

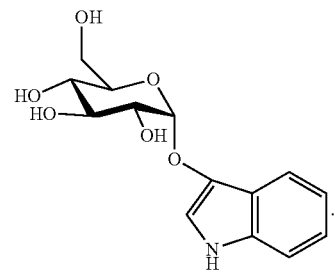

In another variation, $R^1$, $R^2$, $R^4$, and $R^5$ are all H; $R^3$ is bromo; and Z is glucosyl in which the bond from the anomeric carbon is in the β orientation. Thus, in such a variation, the compound of Formula (A) is:

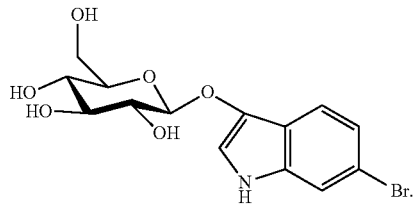

In another variation, $R^1$, $R^2$, $R^4$, and $R^5$ are all H; $R^3$ is bromo; and Z is glucosyl in which the bond from the anomeric carbon is in the α orientation. Thus, in such a variation, the compound of Formula (A) is:

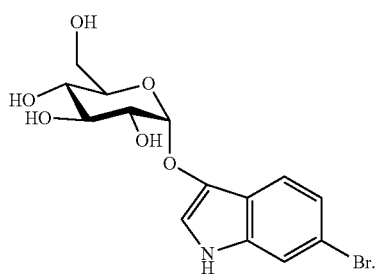

In yet another variation, $R^1$, $R^2$, $R^3$, $R^4$, and $R^5$ are all H; and Z is glucuronosyl in which the attachment from the anomeric carbon is in the β orientation. Thus, in such a variation, the compound of Formula (A) is:

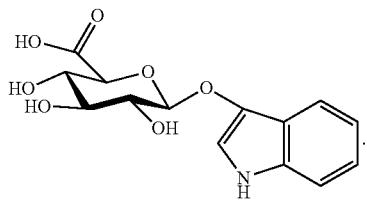

In another variation, $R^1$, $R^2$, $R^3$, and $R^5$ are all H; and Z is —C(O)$R^b$, wherein $R^b$ is methyl. Thus, in such a variation, the compound of Formula (A) is:

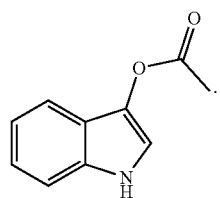

In another variation, $R^1$, $R^2$, $R^3$, $R^4$, and $R^5$ are all H; and Z is —$SO_3^-$. Thus, in such a variation, the compound of Formula (A) is:

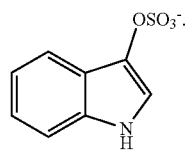

In other variations, the compound of Formula (A) is selected from:

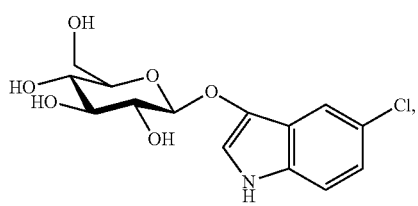

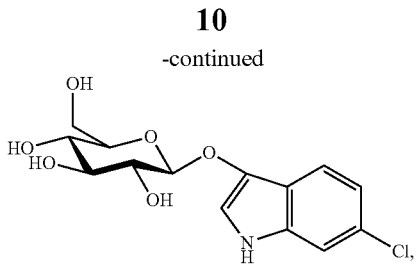

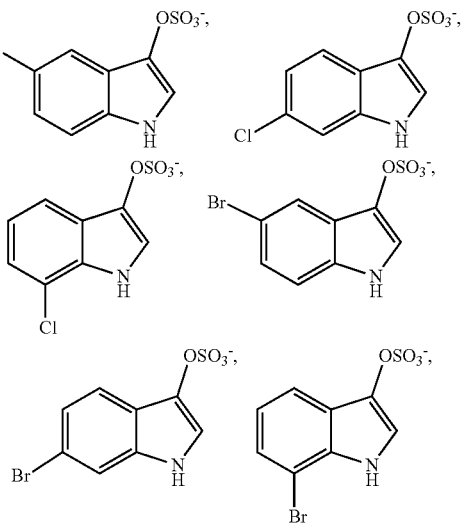

-continued

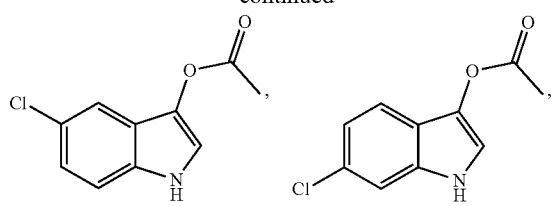
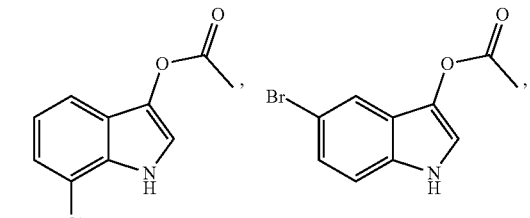
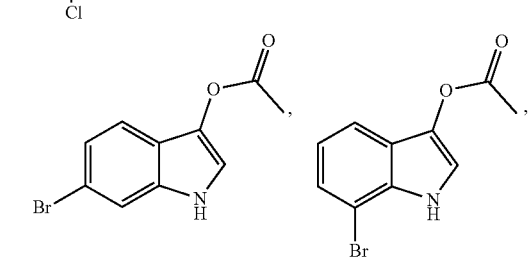
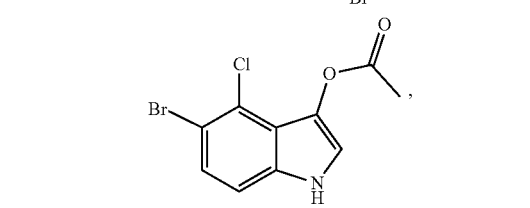
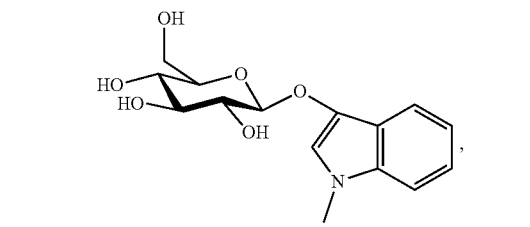
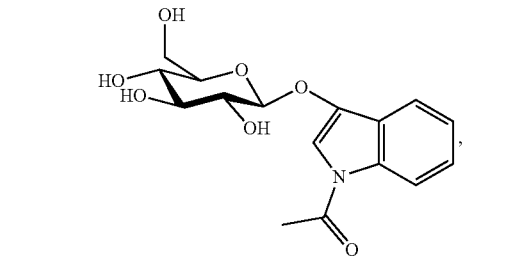
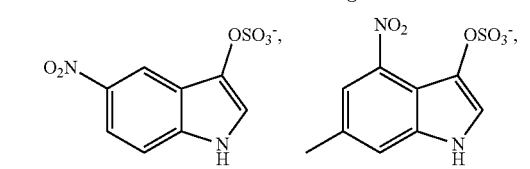
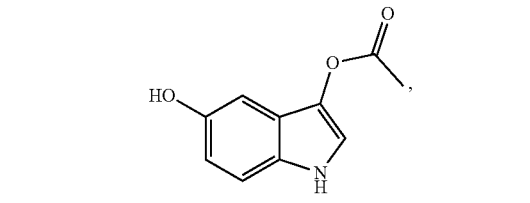

-continued

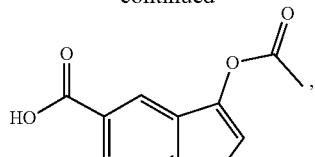
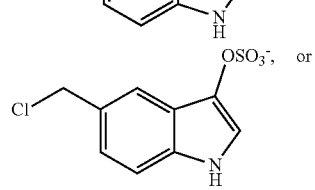, or
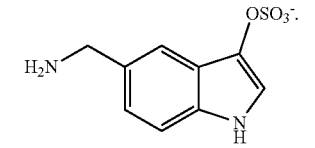

Compounds of Formula (I) and (II): Feed Indole Compounds

In some embodiments, the feed indole compound used in the methods described herein is a compound of Formula (I):

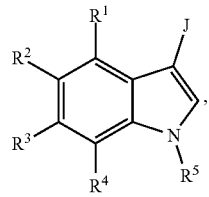

(I)

wherein:
$R^1$, $R^2$, $R^3$, and $R^4$ are independently selected from H, halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and alkyl;
wherein R$^a$ is alkyl; and
R$^b$ and R$^c$ are independently H or alkyl;
$R^5$ is H or alkyl; and
J is alkyl, —OC(O)R$^b$, hydroxyl, or phosphate.

In some embodiments of Formula (I), the alkyl of $R^1$, $R^2$, $R^3$, and $R^4$ at each occurrence is independently unsubstituted or substituted with one or more substituents selected from halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and —R$^a$OR$^d$; wherein R$^a$ and R$^d$ are independently alkyl, and R$^b$ and R$^c$ are independently H or alkyl. In certain embodiments, $R^5$ is independently alkyl, and the alkyl is unsubstituted or substituted with one or more substituents selected from halo, hydroxyl, =O, —C(O)OR$^b$, —R$^a$C(O)OR$^b$, —R$^a$OC(O)R$^b$, —OR$^a$, —NR$^b$R$^c$; wherein R$^a$ is independently alkyl, and R$^b$ and R$^c$ are independently H or alkyl.

In some embodiments of Formula (I), J is alkyl, and the alkyl is unsubstituted or substituted with one or more substituents independently selected from the group consisting of halo, hydroxyl, =O, —C(O)OR$^b$, —R$^a$C(O)OR$^b$, —R$^a$OC(O)R$^b$, —OR$^a$, —NR$^b$R$^c$, and —R$^a$OR$^d$; wherein R$^a$ and R$^d$ are independently alkyl, and R$^b$ and R$^c$ are independently H or alkyl.

In some variations of Formula (I), J is alkyl. In certain variations, J is unsubstituted alkyl. For example, in certain variations, J is unsubstituted methyl, ethyl, propyl, butyl, pentyl, hexyl, heptyl, oxtyl, nonyl, or decyl. In other variations, J is alkyl substituted one or more groups independently selected from halo, hydroxyl, =O, —C(O)OR$^b$, —R$^a$C(O)OR$^b$, —R$^a$OC(O)R$^b$, and —NR$^b$R$^c$. In certain variations, J is alkyl substituted with —C(O)OR$^b$ and —NR$^b$R$^c$, wherein R$^b$ and R$^c$ are H. In other variations, J is alkyl substituted with —NR$^b$R$^c$ and —R$^a$OC(O)R$^b$. In yet other variations, J is alkyl substituted with halo, —C(O)OR$^b$ and —NR$^b$R$^c$, wherein R$^b$ and R$^c$ are H.

In other variations of Formula (I), J is phosphate.

In yet other variations of Formula (I), J is —OC(O)R$^b$, wherein R$^b$ is H or alkyl. In certain variations, J is —OC(O)R$^b$, and R$^b$ is H, methyl, ethyl, propyl, butyl, pentyl, hexyl, heptyl, octyl, nonyl, or decyl. In one embodiment, J is —OC(O)R$^b$, and R$^b$ is methyl.

In other variations of Formula (I), J is hydroxyl, and the compound of Formula (I) is a compound of Formula (II):

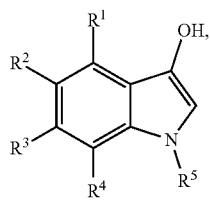

(II)

wherein R$^1$, R$^2$, R$^3$, R$^4$, and R$^5$ are defined as for Formula (I).

It should generally be understood that variations of Formula (I) detailed throughout, where applicable, apply equally to Formula (II), the same as if each and every variation were specifically and individually listed for Formula (II).

It should also generally be understood that any of the variations for R$^1$, R$^2$, R$^3$, R$^4$ and R$^5$ as described herein for Formula (I) or Formula (II) may be combined the same as if each and every combination of the variables were specifically and individually listed.

In some variations of Formula (I) or Formula (II), R$^1$, R$^2$, R$^3$, and R$^4$ are independently H, halo, nitro, hydroxyl, or alkyl. In certain variations, R$^1$, R$^2$, R$^3$, and R$^4$ are independently H, nitro, or hydroxyl. In other variations, R$^1$, R$^2$, R$^3$, and R$^4$ are independently H or nitro. In yet other variations, R$^1$, R$^2$, R$^3$, and R$^4$ are independently H or hydroxyl.

In some variations of the compound of Formula (I) or Formula (II), R$^1$, R$^2$, R$^3$, and R$^4$ are independently H, chloro, bromo, iodo, or fluoro. In some variations, R$^1$, R$^2$, R$^3$, and R$^4$ are independently H, chloro, or bromo. In other variations, R$^1$, R$^2$, R$^3$, and R$^4$ are independently H or chloro. In yet other variations, R$^1$, R$^2$, R$^3$, and R$^4$ are independently H or bromo.

In some variations, R$^1$, R$^2$, R$^3$, and R$^4$ are independently H or alkyl. In some embodiments, R$^1$, R$^2$, R$^3$, and R$^4$ are independently H or methyl, ethyl, propyl, butyl, or pentyl. In certain variations R$^1$, R$^2$, R$^3$, and R$^4$ are independently H or methyl.

In certain variations, the alkyl of R$^1$, R$^2$, R$^3$, and R$^4$ at each occurrence is independently unsubstituted or substituted. For example, in certain variations, at least one of R$^1$, R$^2$, R$^3$, and R$^4$ is alkyl, and the alkyl is substituted with halo. In other variations, the alkyl is substituted with hydroxyl. In yet other variations, the alkyl is substituted with —NR$^b$R$^c$. In other variations, the alkyl is substituted with —NR$^b$R$^c$ and hydroxyl.

R$^1$, R$^2$, R$^3$, and R$^4$ may be the same or different. In some embodiments of Formula (I) or Formula (II), R$^1$, R$^2$, R$^3$, and R$^4$ are all H. In other embodiments, one of R$^1$, R$^2$, R$^3$, and R$^4$ is nitro; and the remaining R$^1$, R$^2$, R$^3$, and R$^4$ are H. In yet other embodiments, one of R$^1$, R$^2$, R$^3$, and R$^4$ is halo; and the remaining R$^1$, R$^2$, R$^3$, and R$^4$ are H.

In certain variations of Formula (I) or Formula (II), R$^5$ is H. In other variations of Formula (I) or Formula (II), R$^5$ is unsubstituted alkyl. For example, in some variations, R$^5$ is unsubstituted methyl, ethyl, propyl, butyl, or pentyl. In certain variations, R$^5$ is methyl. In other variations, R$^5$ is substituted alkyl. For example, in some variations, R$^5$ is alkyl substituted with one or more of halo, hydroxyl, =O, —C(O)OR$^b$, —R$^a$C(O)OR$^b$, —R$^a$OC(O)R$^b$, and —NR$^b$R$^c$. In certain variations, R$^5$ is ethyl substituted with =O. In one variation, R$^5$ is —C(O)CH$_3$.

In some variations of the compound of Formula (I), R$^1$, R$^2$, R$^3$, R$^4$ and R$^5$ are H; J is ethyl substituted with —C(O)OR$^b$ and —NR$^b$R$^c$; R$^b$ in each instance is H, and R$^c$ is H. In one such variation, the compound of Formula (I) is:

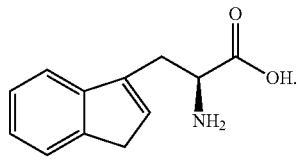 [SMILES: N[C@@H](CC1=CCc2ccccc21)C(=O)O]

In another variation, R$^1$, R$^2$, R$^3$, R$^4$ and R$^5$ are H; and J is phosphate; and the compound of Formula (I) is:

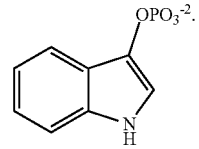

In yet another variation, R$^1$, R$^2$, R$^3$, R$^4$ and R$^5$ are H; J is —OC(O)R$^b$; R$^b$ is methyl; and the compound of Formula (I) is:

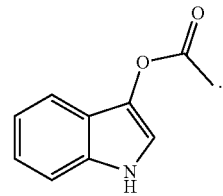

In yet other variations, the compound of Formula (I) is:

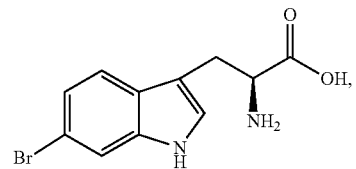

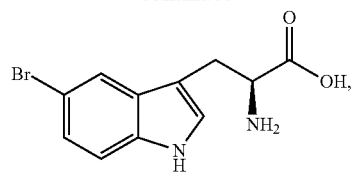
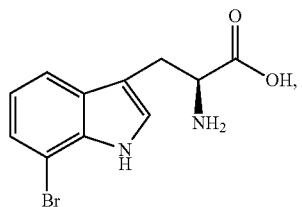
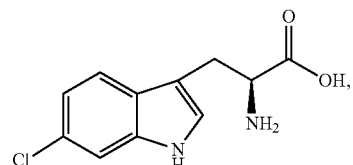
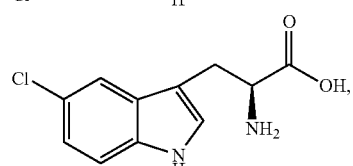
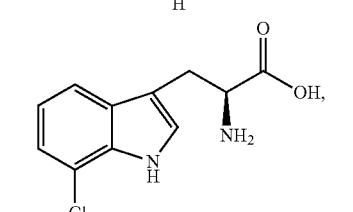
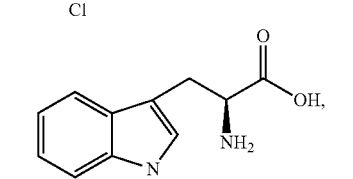
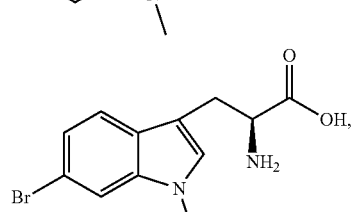
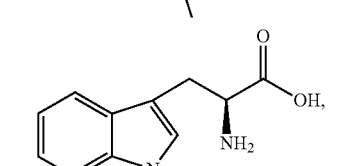
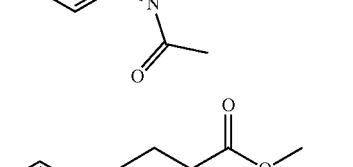
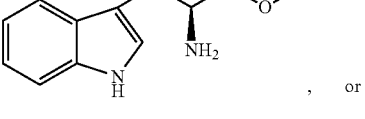, or

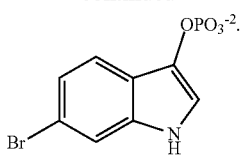

In one variation of the compound of Formula (II), $R^1$, $R^2$, $R^3$, $R^4$, and $R^5$ are all H. In such a variation, the compound of Formula (II) is:

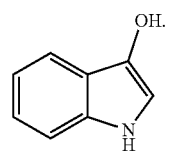

In other variations, the compound of Formula (II) is:

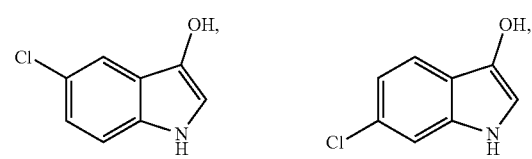

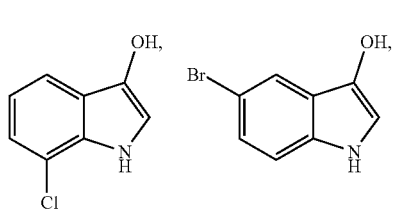

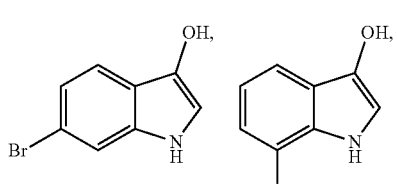

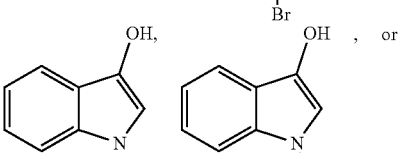, or

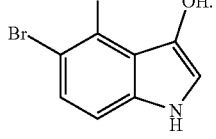

One of skill in the art would recognize that compounds of Formula (II) may readily undergo keto-enol tautomerization to form the corresponding ketone. For example, in some embodiments, the compound of Formula (II):

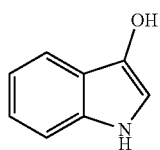

may tautomerize to form the corresponding ketone

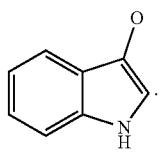

One of skill in the art would recognize conditions that favor one tautomer over the other, including, for example, changes in temperature, the presence of water, and/or the presence of acid. The corresponding ketone tautomers of compounds of Formula (II) may be used to produce indigoid dyes. Thus, in one aspect, provided herein are methods of producing indigoid dyes from the indigoid dye precursors by: a) contacting a feed indole compound with i) a polypeptide with oxygenase activity, and ii) a polypeptide with glycosyltransferase activity, a polypeptide with sulfotransferase activity, a polypeptide with acyltransferase activity, or a combination thereof to produce an indigoid dye precursor; b) tautomerizing the indigoid dye precursor to the corresponding ketone tautomer; and c) converting the indigoid dye precursor ketone tautomer to an indigoid dye.

In some embodiments, the indigoid dye precursor ketone tautomer may undergo additional steps before being converted to an indigoid dye. For example, in some embodiments, the compound of Formula (I) 1H-indol-3-ol is produced according to the methods described herein; the 1H-indol-3-ol is tautomerized to form the corresponding ketone indolin-3-one; the indolin-3-one is oxidized to form indoline-2,3-dione; and the indoline-2,3-dione is converted into the indigoid dye indirubin.

Polypeptides of the Disclosure

The present disclosure relates to polypeptides which facilitate the production of indigoid dye precursors from feed indole compounds. As used herein, a "polypeptide" is an amino acid sequence including a plurality of consecutive polymerized amino acid residues (e.g., at least about 15 consecutive polymerized amino acid residues). As used herein, "polypeptide" refers to an amino acid sequence, oligopeptide, peptide, protein, or portions thereof, and the terms "polypeptide" and "protein" are used interchangeably.

In some embodiments, a polypeptide for use in the methods described herein is a polypeptide with oxygenase activity. As used herein, "oxygenase activity" refers to the ability of a polypeptide to oxidize a substrate by transferring at least one atom of oxygen to the substrate. In some embodiments, the polypeptide is a monooxygenase, i.e., transfers one atom of oxygen to the substrate. In other embodiments, the polypeptide is a dioxygenase, i.e., transfers two atoms of oxygen to the substrate. Any suitable polypeptide with oxygenase activity may be used in the methods described herein. For example, in some embodiments, the polypeptide with oxygenase activity is a naphthalene 1,2-dioxygenase; a cytochrome P450; or a flavin-containing monooxygenase.

In some embodiments, the polypeptide with oxygenase activity for use in the methods described herein is a polypeptide having the amino acid sequence of SEQ ID NO: 1, which encodes the flavin monooxygenase (FMO) from *Methylophaga* sp. strain SK1. In other embodiments, the polypeptide with oxygenase activity has the amino acid sequence of SEQ ID NO: 2, which encodes the cytochrome P450 oxygenase CYP102A1 from *Bacillus megaterium*. In yet other embodiments, the polypeptide with oxygenase activity has the amino acid sequence of SEQ ID NO: 21-24, which encode subunits ndoA, ndoB, ndoC, and ndoR, respectively, of the naphthalene dioxygenase (NDO) from *Pseudomonas putida*. In some embodiments, the polypeptide with oxygenase activity for use in the methods of the present disclosure is a homolog of the polypeptide having the amino acid sequence of any of one of SEQ ID NO: 1, SEQ ID NO: 2, SEQ ID NO: 21, SEQ ID NO: 22, SEQ ID NO: 23, and/or SEQ ID NO: 24. Methods for the identification of polypeptides that are homologs of a polypeptide of interest are well-known to one of skill in the art, as described herein. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 1, SEQ ID NO: 2, SEQ ID NO: 21, SEQ ID NO: 22, SEQ ID NO: 23, and/or SEQ ID NO: 24. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 1, SEQ ID NO: 2, SEQ ID NO: 21, SEQ ID NO: 22, SEQ ID NO: 23, and/or SEQ ID NO: 24.

In some embodiments, a polypeptide for use in the methods described herein is a polypeptide with glycosyltransferase activity. As used herein, "glycosyltransferase activity" refers to the ability of a polypeptide to transfer a glycosyl group to a substrate. In some embodiments, the polypeptide is a glucosyltransferase, i.e., transfers a glucosyl group to a substrate. In other embodiments, the polypeptide is a glucuronosyltransferase, i.e., transfers a glucuronosyl group to a substrate.

In some embodiments, the polypeptide with glycosyltransferase activity for use in the methods described herein is a polypeptide having the amino acid sequence of SEQ ID NO: 3, which encodes the UDP-glucosyltransferase isoform 1 protein from *P. tinctorium*. In other embodiments, the polypeptide with glycosyltransferase activity has the amino acid sequence of SEQ ID NO: 4, which encodes the UDP-glucosyltransferase isoform 2 protein from *P. tinctorium*. In other embodiments, the polypeptide with glycosyltransferase activity has the amino acid sequence of SEQ ID NO: 5, which encodes the UDP-glucosyltransferase protein AHZ08761.1 from *N. tabacum*. In yet other embodiments, the polypeptide with glycosyltransferase activity has the amino acid sequence of SEQ ID NO: 6, which encodes the UDP-glucosyltransferase protein UGT72B1 from *A. thaliana*. In yet other embodiments, the polypeptide with glycosyltransferase activity has the amino acid sequence of SEQ ID NO: 7, which encodes the UDP-glucosyltransferase protein UGT72E2 from *A. thaliana*. In yet other embodiments, the polypeptide with glycosyltransferase activity has the amino acid sequence of SEQ ID NO: 8, which encodes the UDP-glucosyltransferase protein UGT72E3 from *A. thaliana*.

In yet other embodiments, the polypeptide with glycosyltransferase activity has the amino acid sequence of SEQ ID NO: 15, which encodes the protein UGT1 from *I. tinctoria*. In yet other embodiments, the polypeptide with glycosyltransferase activity has the amino acid sequence of SEQ ID NO: 16, which encodes the protein UGT2 from *I. tinctoria*. In yet other embodiments, the polypeptide with glycosyltransferase activity has the amino acid sequence of SEQ ID NO: 17, which encodes the protein UGT1 from *I. suffruticosa*. In yet other embodiments, the polypeptide with glycosyltransferase activity has the amino acid sequence of SEQ ID NO: 18, which encodes the protein UGT2 from *I. suffruticosa*. In yet other embodiments, the polypeptide with glycosyltransferase activity has the amino acid sequence of SEQ ID NO: 19, which encodes the protein XP_002320190.1 from *P. trichocarpa*. In yet other embodiments, the polypeptide with glycosyltransferase activity has the amino acid sequence of SEQ ID NO: 20, which encodes the protein BAG80556.1 from *L. barbarum*.

In yet other embodiments, the polypeptide with glycosyltransferase activity has the amino acid sequence of the catalytic core of the amino acid sequence of any one of SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, and/or SEQ ID NO: 20. In some embodiments, the catalytic core of any one of SEQ ID NO: 3 through SEQ ID NO: 8, or SEQ ID NO: 15 through SEQ ID NO: 20 comprises amino acid 1 through amino acid 270 of the corresponding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20.

In some embodiments, the polypeptide with glycosyltransferase activity for use in the methods of the present disclosure is a homolog of the polypeptide having the amino acid sequence of any of one of SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, and/or SEQ ID NO: 20. Methods for the identification of polypeptides that are homologs of a polypeptide of interest are well-known to one of skill in the art, as described herein. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, and/or SEQ ID NO: 20. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, and/or SEQ ID NO: 20.

In some embodiments, a polypeptide for use in the methods described herein is a polypeptide with sulfotransferase activity. As used herein, "sulfotransferase activity" refers to the ability of a polypeptide to transfer a sulfo group to a substrate.

In some embodiments, the polypeptide with sulfotransferase activity for use in the methods described herein is a polypeptide having the amino acid sequence of SEQ ID NO: 9, which encodes the sulfotransferase protein variant SULT1A1*1 wild type from *H. sapiens*. In other embodiments, the polypeptide with sulfotransferase activity is a polypeptide having the amino acid sequence of SEQ ID NO: 10, which encodes the sulfotransferase protein variant SULT1A1*1 D249G from *H. sapiens*. In other embodiments, the polypeptide with sulfotransferase activity is a polypeptide having the amino acid sequence of SEQ ID NO: 11, which encodes the sulfotransferase protein variant SULT1A1*1 enh1 from *H. sapiens*. In yet other embodiments, the polypeptide with sulfotransferase activity is a polypeptide having the amino acid sequence of SEQ ID NO: 12, which encodes the sulfotransferase protein variant SULT1A3*1 wild type from *H. sapiens*. In other embodiments, the polypeptide with sulfotransferase activity is a polypeptide having the amino acid sequence of SEQ ID NO: 13, which encodes the sulfotransferase protein variant SULT1A3*1 D249G from *H. sapiens*. In other embodiments, the polypeptide with sulfotransferase activity is a polypeptide having the amino acid sequence of SEQ ID NO: 14, which encodes the sulfotransferase protein variant SULT1A3*1 enh1 from *H. sapiens*.

In some embodiments, the polypeptide with sulfotransferase activity for use in the methods of the present disclosure is a homolog of the polypeptide having the amino acid sequence of any of one of SEQ ID NO: 9, SEQ ID NO: 10, SEQ ID NO: 11, SEQ ID NO: 12, SEQ ID NO: 13, and/or SEQ ID NO: 14. Methods for the identification of polypeptides that are homologs of a polypeptide of interest are well-known to one of skill in the art, as described herein. In some embodiments, polypeptides of the present disclosure include polypeptides containing an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of any one of SEQ ID NO: 9, SEQ ID NO: 10, SEQ ID NO: 11, SEQ ID NO: 12, SEQ ID NO: 13, and/or SEQ ID NO: 14. Polypeptides of the disclosure also include polypeptides having at least 10, at least 12, at least 14, at least 16, at least 18, at least 20, at least 30, at least 40, at least 50, at least 60, at least 70, or at least 80 consecutive amino acids of the amino acid sequence of any one of SEQ ID NO: 9, SEQ ID NO: 10, SEQ ID NO: 11, SEQ ID NO: 12, SEQ ID NO: 13, and/or SEQ ID NO: 14.

In some embodiments of the methods described herein, the polypeptide with oxygenase activity and the polypeptide with glycosyltransferase activity, sulfotransferase activity, acyltransferase activity, or a combination thereof, are the same polypeptide. For example, in some embodiments, the polypeptide with oxygenase activity and the polypeptide with glycosyltransferase activity, sulfotransferase activity, acyltransferase activity, or a combination thereof is a fusion protein. As used herein, "fusion protein" refers to a single polypeptide that is produced by joining two or more polynucleotides that previously coded for separate polypeptides. In some variations of the methods described herein, the feed indole compound is contacted by a single polypeptide with both oxygenase activity and glycosyltransferase activity to produce the indigoid dye precursor. In other variations, the feed indole compound is contacted by a single polypeptide with both oxygenase activity and sulfotransferase activity. In yet other variations, the feed indole is contacted by a single polypeptide with both oxygenase activity and acyltransferase activity.

In some embodiments, a polypeptide for use in the methods described herein is a polypeptide with phosphotransferase activity. As used herein, "phosphotransferase activity" refers to the ability of a polypeptide to catalyze a phosphorylation reaction, in which a phosphate group is transferred to a substrate.

In certain embodiments, the present disclosure relates to cDNA encoding the polypeptides described herein, such as cDNAs encoding SEQ ID NOs: 1-29.

Methods of Identifying Sequence Similarity

As described above, various polypeptides having similar sequences to the polypeptides used in the methods and compositions of the present disclosure may also be used herein. Various methods are known to those of skill in the art for identifying similar (e.g. homologs, orthologs, paralogs, etc.) polypeptide and/or polynucleotide sequences, including phylogenetic methods, sequence similarity analysis, and hybridization methods.

Phylogenetic trees may be created for a gene family by using a program such as CLUSTAL (Thompson et al. Nucleic Acids Res. 22: 4673-4680 (1994); Higgins et al. *Methods Enzymol* 266: 383-402 (1996)) or MEGA (Tamura et al. *Mol. Biol. & Evo.* 24:1596-1599 (2007)). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou and Nei, *Mol. Biol. & Evo.* 4:406-425 (1987)). Homologous sequences may also be identified by a reciprocal BLAST strategy. Evolutionary distances may be computed using the Poisson correction method (Zuckerkandl and Pauling, pp. 97-166 in *Evolving Genes and Proteins*, edited by V. Bryson and H. J. Vogel. Academic Press, New York (1965)).

In addition, evolutionary information may be used to predict gene function. Functional predictions of genes can be greatly improved by focusing on how genes became similar in sequence (i.e. by evolutionary processes) rather than on the sequence similarity itself (Eisen, *Genome Res.* 8: 163-167 (1998)). Many specific examples exist in which gene function has been shown to correlate well with gene phylogeny (Eisen, *Genome Res.* 8: 163-167 (1998)).

When a group of related sequences are analyzed using a phylogenetic program such as CLUSTAL, closely related sequences typically cluster together or in the same clade (a group of similar genes). Groups of similar genes can also be identified with pair-wise BLAST analysis (Feng and Doolittle, *J. Mol. Evol.* 25: 351-360 (1987)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, Bioinformatics: Sequence and Genome Analysis Cold Spring Harbor Laboratory Press, Cold Spring Harbor, N.Y., page 543 (2001)).

To find sequences that are homologous to a reference sequence, BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used.

Methods for the alignment of sequences and for the analysis of similarity and identity of polypeptide and polynucleotide sequences are well-known in the art.

As used herein "sequence identity" and a "sequence at least X % identical to . . . " refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, *J. Mol. Biol.* 48:443-453 (1970); the search-for-similarity-method of Pearson and Lipman, *Proc. Natl. Acad. Sci.* 85:2444-2448 (1988); the algorithm of Karlin and Altschul, *Proc. Natl. Acad. Sci. USA* 87:2264-2268 (1990), modified as in Karlin and Altschul, *Proc. Natl. Acad. Sci. USA* 90:5873-5877 (1993).

Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version10.3.0 (Invitrogen, Carlsbad, CA) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. *Gene* 73:237-244 (1988); Higgins et al. *CABIOS* 5:151-153 (1989); Corpet et al., *Nucleic Acids Res.* 16:10881-90 (1988); Huang et al. *CABIOS* 8:155-65 (1992); and Pearson et al., *Meth. Mol. Biol.* 24:307-331 (1994). The BLAST programs of Altschul et al. *J. Mol. Biol.* 215:403-410 (1990) are based on the algorithm of Karlin and Altschul (1990) supra.

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in references cited below (e.g., Sambrook et al., Molecular Cloning: A Laboratory Manual, 2nd Ed., Vol. 1-3, Cold Spring Harbor Laboratory, Cold Spring Harbor, N.Y. ("Sambrook") (1989); Berger and Kimmel, Guide to Molecular Cloning Techniques, Methods in Enzymology, vol. 152 Academic Press, Inc., San Diego, Calif. ("Berger and Kimmel") (1987); and Anderson and Young, "Quantitative Filter Hybridisation." In: Hames and Higgins, ed., Nucleic Acid Hybridisation, A Practical Approach. Oxford, TRL Press, 73-111 (1985)).

Encompassed by the disclosure are polynucleotide sequences that are capable of hybridizing to the disclosed polynucleotide sequences and fragments thereof under various conditions of stringency (see, for example, Wahl and Berger, *Methods Enzymol.* 152: 399-407 (1987); and Kimmel, *Methods Enzymo.* 152: 507-511, (1987)). Full length cDNA, homologs, orthologs, and paralogs of polynucleotides of the present disclosure may be identified and isolated using well-known polynucleotide hybridization methods.

With regard to hybridization, conditions that are highly stringent, and means for achieving them, are well known in the art. See, for example, Sambrook et al. (1989) (supra); Berger and Kimmel (1987) pp. 467-469 (supra); and Anderson and Young (1985) (supra).

Hybridization experiments are generally conducted in a buffer of pH between 6.8 to 7.4, although the rate of hybridization is nearly independent of pH at ionic strengths likely to be used in the hybridization buffer (Anderson and Young (1985)(supra)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency. As a general guideline, high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH.

Hybridization and wash conditions that may be used to bind and remove polynucleotides with less than the desired homology to the nucleic acid sequences or their complements that encode the present polypeptides include, for example: 6×SSC and 1% SDS at 65° C.; 50% formamide, 4×SSC at 42° C.; 0.5×SSC to 2.0×SSC, 0.1% SDS at 50° C. to 65° C.; or 0.1×SSC to 2×SSC, 0.1% SDS at 50° C.-65° C.; with a first wash step of, for example, 10 minutes at about 42° C. with about 20% (v/v) formamide in 0.1×SSC, and with, for example, a subsequent wash step with 0.2×SSC and 0.1% SDS at 65° C. for 10, 20 or 30 minutes.

For identification of less closely related homologs, wash steps may be performed at a lower temperature, e.g., 50° C. An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Wash procedures will generally employ at least two final wash steps. Additional variations on these conditions will be readily apparent to those skilled in the art (see, for example, US Patent Application No. 20010010913).

If desired, one may employ wash steps of even greater stringency, including conditions of 65° C.-68° C. in a solution of 15 mM NaCl, 1.5 mM trisodium citrate, and 0.1% SDS, or about 0.2×SSC, 0.1% SDS at 65° C. and washing twice, each wash step of 10, 20 or 30 min in duration, or about 0.1×SSC, 0.1% SDS at 65° C. and washing twice for 10, 20 or 30 min. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C.

Polynucleotide probes may be prepared with any suitable label, including a fluorescent label, a colorimetric label, a radioactive label, or the like. Labeled hybridization probes for detecting related polynucleotide sequences may be produced, for example, by oligolabeling, nick translation, end-labeling, or PCR amplification using a labeled nucleotide.

Host Cells of the Disclosure

Host cells of the present disclosure are capable of producing an indigoid dye precursor compound of Formula (A) from a feed indole compound. Host cells of the disclosure express a polypeptide with oxygenase activity; and a polypeptide with glycosyltransferase activity, sulfotransferase activity, acyltransferase activity, or phosphotransferase activity, or a combination thereof. In some embodiments, the polypeptide with oxygenase activity and the polypeptide with glycosyltransferase activity, sulfotransferase activity, acyltransferase activity, or phosphotransferase activity, or a combination thereof, expressed by the host cell are separate polypeptides. In other embodiments, the polypeptide with oxygenase activity and the polypeptide with glycosyltransferase activity, sulfotransferase activity, acyltransferase activity, or phosphotransferase activity, or a combination thereof, expressed by the host cell are the same polypeptide.

Host cells of the disclosure may be cultured under conditions such that one or more polypeptides facilitate the production of an indigoid dye precursor compound of Formula (A) from a feed indole compound.

In some embodiments, host cells contain a recombinant nucleic acid of the present disclosure. In some embodiments, host cells of the present disclosure contain a recombinant nucleic acid encoding SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and/or SEQ ID NO: 24. In some embodiments, host cells of the present disclosure contain a recombinant nucleic acid encoding a homolog or fragment of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and/or SEQ ID NO: 24.

In some embodiments, the host cells contain a recombinant nucleic acid encoding SEQ ID NO: 1 and a recombinant nucleic acid encoding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20. In other embodiments, the host cells contain a contain a recombinant nucleic acid encoding SEQ ID NO: 2 and a recombinant nucleic acid encoding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20. In other embodiments, the host cells contain a contain a recombinant nucleic acid encoding SEQ ID NO: 21 and a recombinant nucleic acid encoding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20. In other embodiments, the host cells contain a contain a recombinant nucleic acid encoding SEQ ID NO: 22 and a recombinant nucleic acid encoding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20. In other embodiments, the host cells contain a contain a recombinant nucleic acid encoding SEQ ID NO: 23 and a recombinant nucleic acid encoding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20. In other embodiments, the host cells contain a contain a recombinant nucleic acid encoding SEQ ID NO: 24 and a recombinant nucleic acid encoding SEQ ID NO: 3, SEQ ID NO: 4, SEQ ID NO: 5, SEQ ID NO: 6, SEQ ID NO: 7, SEQ ID NO: 8, SEQ ID NO: 15, SEQ ID NO: 16, SEQ ID NO: 17, SEQ ID NO: 18, SEQ ID NO: 19, or SEQ ID NO: 20.

In yet other embodiments, the host cells contain a contain a recombinant nucleic acid encoding SEQ ID NO: 1 and a recombinant nucleic acid encoding SEQ ID NO: 9, SEQ ID NO: 10, SEQ ID NO: 11, SEQ ID NO: 12, SEQ ID NO: 13, or SEQ ID NO: 14. In still other embodiments, the host cells contain a contain a recombinant nucleic acid encoding SEQ ID NO: 2 and a recombinant nucleic acid encoding SEQ ID NO: 9, SEQ ID NO: 10, SEQ ID NO: 11, SEQ ID NO: 12, SEQ ID NO: 13, or SEQ ID NO: 14. In still other embodiments, the host cells contain a contain a recombinant nucleic acid encoding SEQ ID NO: 21 and a recombinant nucleic acid encoding SEQ ID NO: 9, SEQ ID NO: 10, SEQ ID NO: 11, SEQ ID NO: 12, SEQ ID NO: 13, or SEQ ID NO: 14. In still other embodiments, the host cells contain a contain a recombinant nucleic acid encoding SEQ ID NO: 22 and a recombinant nucleic acid encoding SEQ ID NO: 9, SEQ ID NO: 10, SEQ ID NO: 11, SEQ ID NO: 12, SEQ ID NO: 13, or SEQ ID NO: 14. In still other embodiments, the host cells contain a contain a recombinant nucleic acid encoding SEQ ID NO: 23 and a recombinant nucleic acid encoding SEQ ID NO: 9, SEQ ID NO: 10, SEQ ID NO: 11, SEQ ID NO: 12, SEQ ID NO: 13, or SEQ ID NO: 14. In still other embodiments, the host cells contain a contain a recombinant nucleic acid encoding SEQ ID NO: 24 and a recombinant nucleic acid encoding SEQ ID NO: 9, SEQ ID NO: 10, SEQ ID NO: 11, SEQ ID NO: 12, SEQ ID NO: 13, or SEQ ID NO: 14.

When the recombinant nucleotide is expressed in the host to produce a polypeptide such as, for example, the polypeptide encoded by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and/or SEQ ID NO: 24, the recombinant polypeptide may facilitate the production of a compound of Formula (A) from a compound of Formula (II) when the host cell has been contacted with a compound of Formula (II).

Host Cell Types

Host cells of the present disclosure may include or be derived from a variety of sources readily apparent to those skilled in the art. Host cells of the present disclosure may be prokaryotic such as, for example, an organism from the kingdom Eubacteria, which includes species of bacteria. In some embodiments, a prokaryotic host cell may include, for example, a cell from the bacterium *Escherichia coli* or the bacterium *Corynebacterium glutamicum*.

Host cells of the present disclosure may also be eukaryotic and may include, for example, fungal, plant, insect and mammalian cells. In some embodiments, the host cell is from yeast, such as, for example, *Saccharomyces cerevisiae, Pichia pastoris, Kluyveromyces lactis, Kluyveromyces marxianus*, and *Schizosaccharomyces pombe*.

Host Cell Modifications

Host cells of the present disclosure may also include, for example, host cells that produce uracil-diphosphate glucose (UDP-glucose). Host cells of the present disclosure may be modified to produce excess quantities of UDP-glucose as compared to a corresponding unmodified host cell. The modification may be, for example, genetic modification. Where the modification is a genetic modification, a corresponding unmodified host cell may be, for example, a host cell that lacks the same genetic modification facilitating the production of excess quantities UDP-glucose in the modified host cell.

Host cells that produce excess quantities of UDP-glucose, as well as methods of making such host cells, are known in the art. For example, in some embodiments, overexpression of UDP-glucose biosynthesis enzymes (e.g., UDP-glucose pyrophosphorylase) and/or sugar interconversion enzymes (e.g., phosphoglucomutase) in the host cell result in increased production of UDP-glucose as compared to host cells without the corresponding overexpression. In other embodiments, heterologous overexpression of sucrose synthase and sucrose transporter genes by the host cell result in regeneration of UDP-glucose via the breakdown of sucrose. See Zichao Mao, Hyun-Dong Shin, and Rachel Ruizhen Chen, Engineering the *E. coli* UDP-Glucose Synthesis Pathway for Oligosaccharide Synthesis, Biotechnol. Prog. (2006), 22, pages 369-374; and WO2013022989. In still other embodiments, the expression of genes encoding phosphoglucose isomerase, phosphoglucose mutase, or UDP-glucose-4-epimerase are reduced or eliminated in the host cell, which prevents loss of UDP-glucose to glycolysis and galactose. See Dinesh Simkhada, Nagendra Prasad Kurumbang, Hei Chan Lee, and Jae Kyung Sohng, Exploration of Glycosylated Flavonoids from Metabolically Engineered *E. coli, Biotechnology and Bioprocess Engineering* (2010), 15, pages 754-760.

Host cells of the present disclosure may also include, for example, host cells that produce 3'-phosphoadenosine-5'-phosphosulfate (PAPS). Host cells of the present disclosure may be modified to produce excess quantities of PAPS as compared to a corresponding unmodified host cell. The modification may be, for example, genetic modification. Where the modification is a genetic modification, a corresponding unmodified host cell may be, for example, a host cell that lacks the same genetic modification facilitating the production of excess quantities PAPS in the modified host cell.

Host cells that produce excess quantities of PAPS, as well as methods of making such host cells, are known in the art. In some embodiments, the overexpression of ATP sulfurylase and adenosine-5'-phosphosulfate kinase by the host cell leads to production of excess quantities of PAPS. In other embodiments, the reduction or elimination of expression of genes encoding PAPS reductase in the host cell leads to decreased production of PAPS. See Elio Rossi, Sara Motta, Pierluigi Mauri, Paolo Landini, Sulfate assimilation pathway intermediate phosphoadenosine 5'-phosphosulfate acts as a signal molecule affecting production of curli fibres in *Escherichia coli, Microbiology* (2014), 160, 9, pages 1832-1844.

Host cells of the present disclosure may yet also include, for example, host cells that produce indole. Host cells of the present disclosure may be modified to produce excess quantities of indole as compared to a corresponding unmodified host cell. The modification may be, for example, genetic modification. Where the modification is a genetic modification, a corresponding unmodified host cell may be, for example, a host cell that lacks the same genetic modification facilitating the production of excess quantities indole in the modified host cell.

Host cells that produce excess quantities of indole, as well as methods of making such host cells, are known in the art. In some embodiments, the reduction or elimination of genes encoding the glucose phosphotransferase system of the host cell and the overexpression of genes encoding a pentose phosphate pathway transketolase of the host cell leads to accumulation of phosphoenolpyruvate and erythrose-4-phosphate, a precursor to aromatic amino acid and indole synthesis. See U.S. Pat. No. 6,962,794 In other embodiments, overexpression of genes encoding enzymes of aromatic amino acid (e.g, tryptophan) biosynthesis pathways in the host cell lead to increased production of tryptophan, indole, and indole precursors. For example, in certain embodiments, the genes that encode 3-deoxy-D-arabino-heptulosonic acid 7-phosphate synthase and/or anthranilate synthase are overexpressed in the host cell. See Berry, A. et al. Application of metabolic engineering to improve both the production and use of biotech indigo, *Journal of Industrial Microbiology & Biotechnology,* (2002), 28, 127, pages 133. In still other embodiments, a gene encoding tryptophan indole-lyase or mutant indole-releasing tryptophan synthase is overexpressed in the host cell, which leads to increased conversion of tryptophan or indole precursors into free indole. See U.S. Pat. No. 5,494,816.

Host cells of the present disclosure may also include, for example, host cells that naturally produce one or more hydrolases, including, for example, glycosidase, sulfatase, and/or esterase. Host cells of the present disclosure may be modified to produce decreased quantities of one or more hydrolases as compared to a corresponding unmodified host cell. The modification may be, for example, genetic modification. Where the modification is a genetic modification, a corresponding unmodified host cell may be, for example, a host cell that lacks the same genetic modification facilitating the production of decreased quantities of one or more hydrolases in the modified host cell.

Host cells that produce decreased quantities of one or more hydrolases, as well as methods of making such host cells, are known in the art. In some embodiments, the expression of genes encoding native glycosylhydrolases, sulfatases, and/or esterases is decreased or eliminated in the host cell, which leads to reduced hydrolysis of desired products.

Host cells of the present disclosure may also include, for example, host cells that possess heterologous genes encoding oligosaccharide transporters, organic anion transporters, and/or multidrug transporters, which may lead to increased export of glycosyl- or sulfate-containing compounds. See Sandermann H Jr, beta-D-Galactoside transport in *Escherichia coli:* substrate recognition, *Eur J Biochem* (1977), 80, 2, pages 507-515; Enomoto A, Takeda M, Tojo A, Sekine T, Cha S H, Khamdang S, Takayama F, Aoyama I, Nakamura S, Endou H, Niwa T. Role of organic anion transporters in the tubular transport of indoxyl sulfate and the induction of its nephrotoxicity, *J Am Soc Nephrol,* (2002), 13, 7, pages 1711-1720.

Host cells of the present disclosure may also include, for example, host cells that possess a heterologous gene for an isatin hydrolase, which may lead to decreased production of the indirubin by-product during production of indoxyl by the host cell. See Berry, A. et al., Application of metabolic engineering to improve both the production and use of biotech indigo. *Journal of Industrial Microbiology & Biotechnology,* (2002), 28, pages 127-133.

Host cells of the present disclosure may also include cells that either naturally exhibit reduced hydrolysis of compounds produced by methods of the present disclosure or are engineered to reduce hydrolysis of compounds produced by methods of the present disclosure, including, for example, indoxyl acetate. Such host cells may naturally, or be engineered such that they do not produce one or more of the following polypeptides: acetyl esterase, esterase yjfP, pimeloyl-[acyl-carrier protein] methyl ester esterase, S-formylglutathione hydrolase YeiG, S-formylglutathione hydrolase FrmB, proofreading thioesterase EntH, uncharacterized protein YdiL, acyl-CoA thioesterase I, probable 9-O-acetyl-N-acetylneuraminic acid deacetylase, esterase YqiA, esterase YbfF, esterase YpfH, acetylornithine deacetylase, esterase FrsA, acyl-CoA thioester hydrolase YbgC, and tryptophanase.

Contacting a Host Cell with a Compound of Formula (I)

In some embodiments of the methods of the present disclosure, a host cell containing a recombinant polypeptide of the disclosure is contacted with a feed indole compound of Formula (I), and an indigoid dye precursor of Formula (A) is produced from the feed indole compound. In certain embodiments, the compound of Formula (I) is a compound of Formula (II).

In certain embodiments, to contact a host cell with a feed indole compound, the feed indole compound is added to the growth medium of the host cell. In other embodiments, to contact a host cell with a feed indole compound, the feed indole compound is produced by the host cell. For example, in certain embodiments, the host cell produces 1H-indol-3-ol, and converts the 1H-indol-3-ol to a compound of Formula (A).

In yet other embodiments, to contact a host cell with a feed indole compound, the host cell produces a first feed indole compound and converts the first feed indole compound to one or more additional feed indole compounds. For example, in certain embodiments, the host cell produces tryptophan, converts the tryptophan to 1H-indol-3-ol, and converts the 1H-indol-3-ol to a compound of Formula (A).

In still other embodiments, to contact a host cell with a feed indole compound, the feed indole compound is produced by other means in the growth medium of the host cell. For example, in certain embodiments, the feed indole compound is produced by another organism in the growth medium of the host cell, and the host cell converts the feed indole compound to a compound of Formula (A). In another variation, for example, the feed indole compound is produced in vitro in the growth medium of the host cell, and the host cell converts the feed indole compound to a compound of Formula (A).

Culture Conditions for Host Cells

In some embodiments, the methods of the present disclosure include contacting a host cell containing a recombinant polypeptide of the disclosure with a feed indole compound, and culturing the host cell under conditions such that an indigoid dye precursor of Formula (A) is produced from the feed indole compound.

Standard methods of culturing organisms such as, for example, bacteria and yeast, are well-known in the art and are described herein. For example, host cells may be cultured in a standard growth media under standard temperature and pressure conditions, and in an aerobic environment. Standard growth media for various host cells are commercially available and well-known in the art, as are standard conditions for growing various host cells. Suitable conditions for facilitating the production of compounds of Formula (A) from compounds of Formula (I) or (II) by host cells are described herein and will be readily apparent to one of skill in the art in view of the present disclosure.

In some embodiments, various compounds and/or reagents may be added to the growth medium of a host cell that produces a recombinant polypeptide of the disclosure to enhance or facilitate the production of compounds of Formula (A) from compounds of Formula (II). In some embodiments, the culture medium is supplemented with protecting group precursors such as glucose, galactose, xylose, sucrose, sulfate, or acetate. In some embodiments, the culture medium is supplemented with feed indole compounds, including, for example, tryptophan or indole. The culture media may be supplemented with combinations of various compounds and/or reagents. For example, in some embodiments, the culture media is supplemented with tryptophan and glucose.

Isolation of the Compound of Formula (A)

In some embodiments, after a compound of Formula (A) has been produced from a feed indole compound, a recovery step may be performed to recover the compound of Formula (A) from the host cell, the growth medium, or the in vitro reaction. In some embodiments, the host cells used in the methods described herein may excrete the compounds of Formula (A) produced. In other embodiments, the compounds of Formula (A) produced are not excreted by the host cells. Methods for the recovery of compounds of Formula (A) may include, for example, sonication, centrifugation, precipitation, filtration, chromatography, crystallization, and/or solvent extraction.

Compounds of Formula (A) that have been recovered from a host cell may be referred to as substantially purified compounds of Formula (A). A substantially purified compound of Formula (A) generally refers to a compound of Formula (A) that is substantially free of contaminating agents (e.g. cellular material and other culture medium components) from the culture medium source where the compound of Formula (A) is produced by the host cell. For example, a substantially purified compound of Formula (A) may be in association with less than 30%, 20%, 10%, and more preferably 5% or less (by weight) contaminating agents. A composition containing a substantially purified compound of Formula (A) preparation may include, for example, a composition where culture medium (and associated contaminating agents) represents less than about 20%, sometimes less than about 10%, and often less than about 5% of the volume of the compound of Formula (A) preparation.

The titer of the compound of Formula (A) produced may be, for example, at least 1 mg/L, at least 10 mg/L, at least 50 mg/L, at least 100 mg/L, at least 1 g/L, at least 10 g/L, at least 25 g/L, at least 50 g/L, at least 75 g/L, at least 100 g/L, at least 125 g/L, at least 150 g/L, at least 175 g/L, at least 200 g/L, or at least 250 g/L. In certain embodiments, the titer of the compound of Formula (A) produced is between 75 g/L and 150 g/L. In other embodiments, the titer of the compound of Formula (A) produced is at least 100 g/L.

In Vitro Methods for Production of Compounds of Formula (A)

In some embodiments, the methods of the present disclosure include contacting a feed indole compound with a recombinant polypeptide of the disclosure and incubating the feed indole compound under conditions such that a compound of Formula (A) is produced from the feed indole compound.

Standard methods of performing in vitro enzymatic reactions are well-known in the art and are described herein. In an exemplary embodiment, a polypeptide of the present disclosure is expressed in a host cell and substantially purified. The substantially purified polypeptide may be added to an in vitro reaction platform, such, for example, as a well of a 96-well plate, where the well contains a feed indole compound, such as a compound of Formula (II). The purified polypeptide and the feed indole compound may be incubated together for a period of time to allow production of a compound of Formula (A) from the feed indole compound.

In some embodiments, various compounds and/or reagents may be added to the in vitro platform containing a polypeptide of the disclosure and a feed indole compound to enhance or facilitate the production of a compound of Formula (A) from a feed indole compound. In some embodiments, the platform is supplemented with redox cofactors, including, for example, nicotinamide adenine dinucleotide (NAD⁺) or nicotinamide adenine dinucleotide phosphate (NADP⁺), or their respective hydrides (NADH or NADPH). The platform may be supplemented with combinations of various compounds and/or reagents, such as, for example, a redox cofactor regeneration system comprising a redox-active enzyme, an enzyme substrate, NADP⁺, and/or NADPH. In some variations, the redox cofactor regeneration system comprises glucose oxidase, glucose, NADP⁺, and/or NADPH.

Use of Compounds of Formula (A) to Produce Compounds of Formula (B)

The indigoid dye precursor compounds of Formula (A) produced according to the methods described herein may be used to produce an indigoid dye compound of Formula (B):

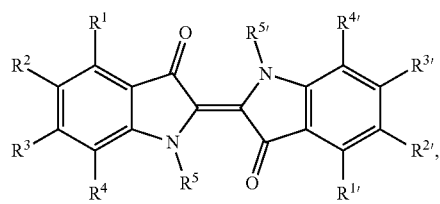

(B)

wherein $R^1$, $R^2$, $R^3$, $R^4$, $R^5$, $R^{1'}$, $R^{2'}$, $R^{3'}$, $R^{4'}$, and $R^{5'}$ are defined as for Formula (A).

Thus, in one aspect, provided herein are methods of producing a compound of Formula (B), comprising converting a first compound of Formula (A) and a second compound of Formula (A) to a compound of Formula (B). In some embodiments, the first compound of Formula (A) and the second compound of Formula (A) are the same compound of Formula (A). In other embodiments, the first compound of Formula (A) and the second compound of Formula (A) are different compounds of Formula (A). In some embodiments, at least one of the first compound of Formula (A) and the second compound of Formula (A) is produced according to the methods described herein.

In some embodiments, one or more compounds of Formula (A) may be used to produce a compound of Formula (B). It should be appreciated by one of skill in the art that the $R^1$, $R^2$, $R^3$, $R^4$, $R^5$, $R^{1'}$, $R^{2'}$, $R^{3'}$, $R^{4'}$, and $R^{5'}$ of the one or more compounds of Formula (A) are the same $R^1$, $R^2$, $R^3$, $R^4$, $R^5$, $R^{1'}$, $R^{2'}$, $R^{3'}$, $R^{4'}$, and $R^{5'}$ of the compound of Formula (B).

The one or more compounds of Formula (A) used to produce the compound of Formula (B) may be the same compound of Formula (A).

For example, in one variation, the compound of Formula (A) is:

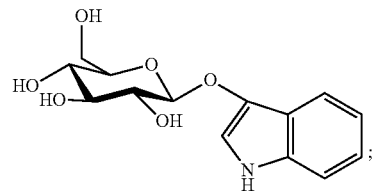

and the compound of Formula (B) is:

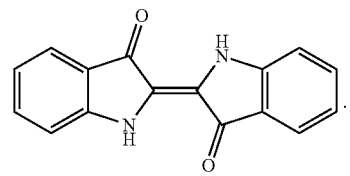 [SMILES: O=C1/C(=C2\Nc3ccccc3C2=O)Nc2ccccc21]

In another variation, the compound of Formula (A) is:

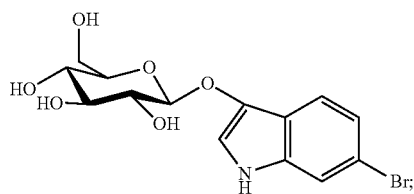

and the compound of Formula (B) is:

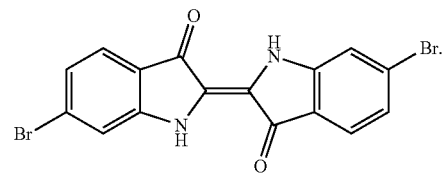 [SMILES: O=C1/C(=C2\Nc3cc(Br)ccc3C2=O)Nc2cc(Br)ccc21]

In another variation, the compound of Formula (A) is:

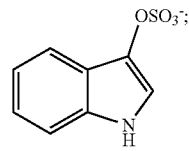

and the compound of Formula (B) is:

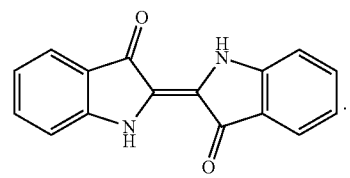 [SMILES: O=C1/C(=C2\Nc3ccccc3C2=O)Nc2ccccc21]

In yet another variation, the compound of Formula (A) is:

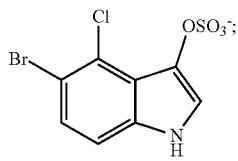

and the compound of Formula (B) is:

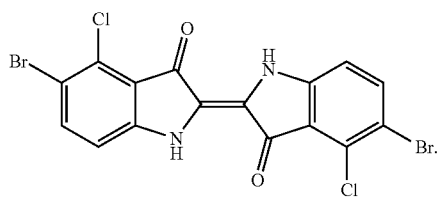 [SMILES: O=C1/C(=C2\Nc3ccc(Br)c(Cl)c3C2=O)Nc2ccc(Br)c(Cl)c21]

In other embodiments, the one or more compounds of Formula (A) used to produce the compound of Formula (B) may be different compounds of Formula (A).

For example, in one variation, the compounds of Formula (A) are:

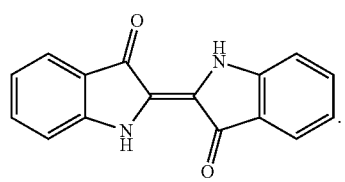 [SMILES: O=C1/C(=C2\Nc3ccccc3C2=O)Nc2ccccc21]

and the compound of Formula (B) is:

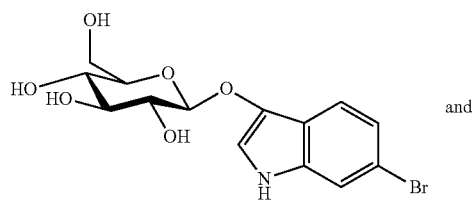

In another variation, the compounds of Formula (A) are:

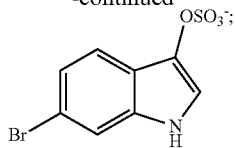

-continued

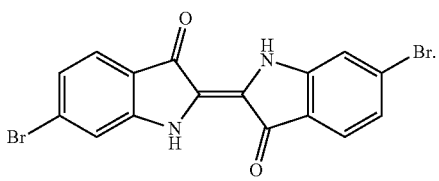 [SMILES: O=C1/C(=C2\Nc3cc(Br)ccc3C2=O)Nc2cc(Br)ccc21]

and the compound of Formula (B) is:

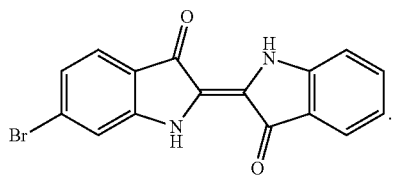 [SMILES: O=C1/C(=C2\Nc3cc(Br)ccc3C2=O)Nc2ccccc21]

In yet another variation, the compounds of Formula (A) are:

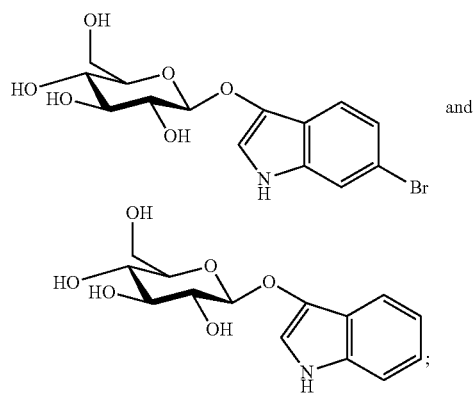

and the compound of Formula (B) is:

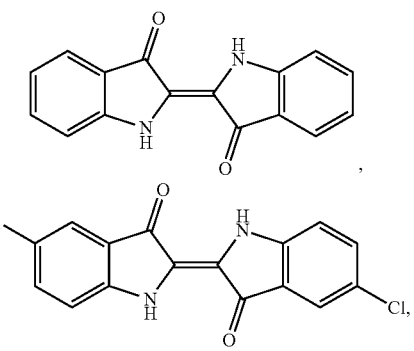

In certain variations, the compound of Formula (B) is:

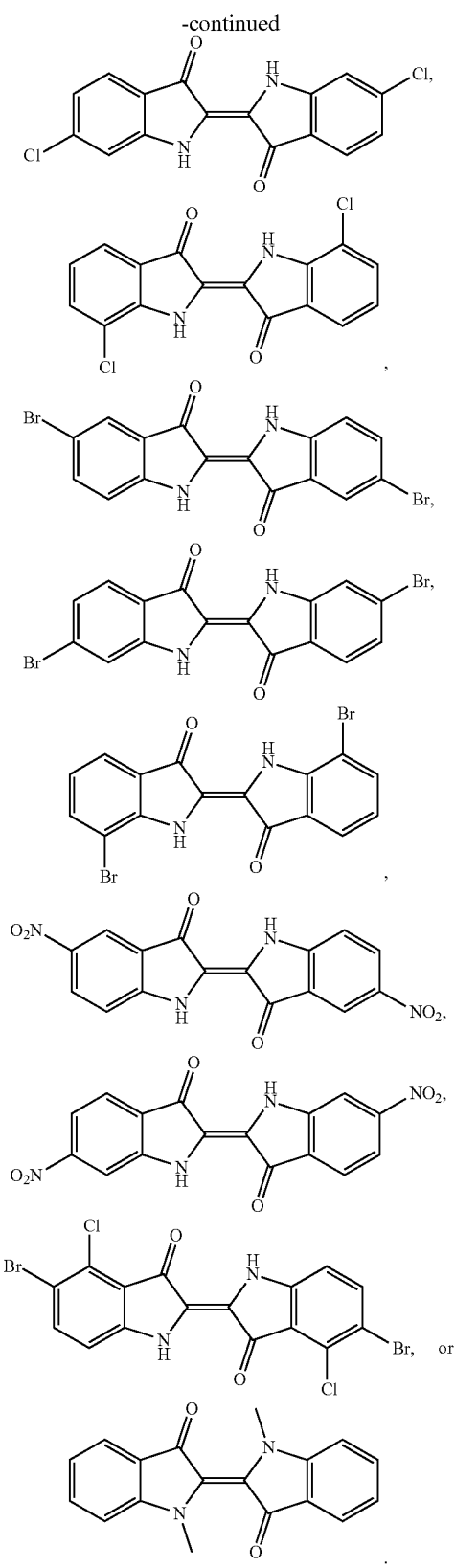

In some embodiments, a compound of Formula (B) is produced from one or more compounds of Formula (A), and each of the one or more compounds of Formula (A) is produced according to the methods described herein.

In other embodiments, a compound of Formula (B) is produced from one or more compounds of Formula (A), and at least a portion of the one or more compounds of Formula (A) is produced according to the methods described herein, while at least a portion of the one or more compounds of Formula (A) is produced according to other methods. For example, in certain embodiments, at least a portion of the one or more compounds of Formula (A) is isolated from a plant.

In some embodiments, a compound of Formula (B) may be produced by i) converting one or more compounds of Formula (A) to one or more compounds of Formula (II), then ii) converting the one or more compounds of Formula (II) to a compound of Formula (B). The one or more compounds of Formula (A) may be converted to the one or more compounds of Formula (II) by any suitable methods known in the art.

For example, in some embodiments, a compound of Formula (A) is contacted by a hydrolase to produce a compound of Formula (II). Any appropriate hydrolase may be used to produce a compound of Formula (II) from a compound of Formula (A). For example, in certain embodiments, a compound of Formula (A) is contacted by a β-glucosidase, α-glucosidase, sulfatase, phosphatase or esterase to produce a compound of Formula (II). In one variation, a compound of Formula (A) is contacted by the hydrolase atsA from P. aeruginosa to produce a compound of Formula (II). In another variation, a compound of Formula (A) is contacted by the hydrolase bglA from Bacillus circulans to produce a compound of Formula (II).

In other embodiments, a compound of Formula (A) is converted to a compound of Formula (II) in the presence of an acid catalyst. For example, in certain embodiments, a compound of Formula (A) is converted to a compound of Formula (II) in the presence of hydrochloric acid. In some embodiments, a compound of Formula (A) is converted to a compound of Formula (II) in the presence of 0.001 M hydrochloric acid at a temperature above room temperature.

In some embodiments, a compound of Formula (B) is produced by i) converting one or more compounds of Formula (A) to one or more compounds of Formula (II), ii) combining the one or more compounds of Formula (II) with one or more additional compounds of Formula (II), then iii) converting the one or more compounds of Formula (II) to a compound of Formula (B). In some embodiments, the one or more additional compounds of Formula (II) are not produced according to the methods described herein.

One or more compounds of Formula (II) may be converted to a compound of Formula (B) by any suitable methods known in the art. See Lojda, Z. Indigogenic methods for glycosidases, Histochemie (1970), 22, 4, pages 347-361. For example, in certain variations, one or more compounds of Formula (II) is contacted by oxygen to produce a compound of Formula (B). In some embodiments, one or more compounds of Formula (II) is contacted by atmospheric oxygen to produce a compound of Formula (B). In some embodiments, one or more compounds of Formula (II) is contacted by air to produce a compound of Formula (B).

In certain embodiments, a compound of Formula (II) is converted to a compound of Formula (B) in the additional presence of an oxidative catalyst, including, for example, $[Fe(CN)_6]^{4-}$ or $[Fe(CN)_6]^{3-}$. In some embodiments, one or more compounds of Formula (II) is contacted by oxygen in the presence of $[Fe(CN)_6]^{4-}$ or $[Fe(CN)_6]^{3-}$ to produce a compound of Formula (B).

A compound of Formula (A), Formula (II), and/or Formula (B) produced according to the methods described herein may be used in any suitable application. For example, in some embodiments, a compound of Formula (A), Formula (II), and/or Formula (B) is used in the dyeing of clothes or objects. In some variations, a compound of Formula (A), Formula (II), and/or Formula (B) is used in the dyeing of jeans. In certain variations, a compound of Formula (A) is converted to a compound of Formula (II), the compound of Formula (II) is applied to clothes, and then the compound of Formula (II) is converted to a compound of Formula (B).

EXAMPLES

The following Examples are offered for illustrative purposes and to aid one of skill in better understanding the various embodiments of the disclosure. The following examples are not intended to limit the scope of the present disclosure in any way.

Example 1

Identification and Isolation of Gene Encoding UDP-Glucose:Glucosyltransferase Isoform 1 from *Polygonum tinctorium*

This Example demonstrates the identification and isolation of the glycosyltransferase gene encoding UDP-glucose:glucosyltransferase isoform 1 from the plant *Polygonum tinctorium*.

*P. tinctorium* plants were grown indoors in a greenhouse or laboratory environment. Samples of leaf tissue were taken from live plants at several points during the day and frozen in liquid nitrogen. These samples were mixed, kept frozen with liquid nitrogen, and crushed using 5 mm diameter steel beads in a beadbeater at 30 Hz for 2 min. Total RNA was extracted from the 100 mg of powdered frozen leaf tissue using the Qiagen RNEasy Plant Mini kit obtained from Qiagen GMBH (Hilden, Germany), in accordance with the manufacturer recommended protocol. The mRNA was extracted from the total RNA using magnetic beads coated with oligo $(dT)_{25}$. The mRNA was then sheared to approximately 550 base pairs in length using a Covaris S2 ultrasonicator from Covaris Inc. (Woburn, MA). A cDNA library was generated using the Apollo 324 Next-Gen Library Prep System from Wafergen Biosystems Inc. (Fremont, CA) using the manufacturer-supplied PrepX RNA-Seq Library Preparation Kit. The cDNA library was then clustered using the cBot from Illumina Inc. (San Diego, CA) and the clustered sample was loaded onto an Illumina HiSeq2500 and sequenced using the Rapid Run reagent kit for 150 base, paired-end reads.

Paired-end reads received from the Illumina HiSeq2500 sequencer were first trimmed to remove low-quality reads using the Trimmomatic software package in paired-end mode to remove Illumina adapter sequences and using a sliding quality window of 30 or greater, where reads with under 36 acceptable bases are dropped. See Bolger A M, Lohse M, Usadel B, Trimmomatic: a flexible trimmer for Illumina sequence data, *Bioinformatics*, (2014), 30(15), pages 2114-20. Overlapping paired-end reads were then merged using the FLASH software package with a minimum overlap size of 15 bases and an expected fragment length of 350 bases. See Tanja Magoč and Steven L. Salzberg. FLASH: fast length adjustment of short reads to improve genome assemblies, *Bioinformatics*, (2011), 27(21), pages 2957-2963. The remaining merged and unmerged reads were pooled and digitally normalized to remove redundant data using the khmer software package with options set to paired-end, k-mer size of 19, culling count of 20, and 4 hash tables of 4 GiB each. See Brown C T, Howe A C, Zhang Q, Pyrkosz A B, Brom T H, A Reference-Free Algorithm for Computational Normalization of Shotgun Sequencing Data, arXiv:1203.4802 [q-bio.GN], http://arxiv.org/abs/1203.4802, accessed Mar. 2, 2015. Following digital normalization, reads were assembled into transcript scaffolds using the Trinity RNA-seq assembly package in paired-end mode. Scaffolds were then annotated using BLASTX against a library of known plant glycosyltransferases with an E-value threshold of 1e-60 to identify glucosyltransferase candidates. These candidates were then translated into peptides using the Trinity package, Transdecoder, using the default settings. See Haas B J, Papanicolaou A, Yassour M, Grabherr M, Blood P D, Bowden J, Couger M B, Eccles D, Li B, Lieber M, Macmanes M D, Ott M, Orvis J, Pochet N, Strozzi F, Weeks N, Westerman R, William T, Dewey C N, Henschel R, Leduc R D, Friedman N, Regev A, De novo transcript sequence reconstruction from RNA-seq using the Trinity platform for reference generation and analysis, *Nat Protoc*, (2013), 8, pages 1494-1512.

The predicted UDP-glucose:glucosyltransferase was purified from *P. tinctorium* following the protocol of Minami et al. See Yoshiko Minami, Osamu Nishimura, Ikuko Hara-Nishimura, Mikio Nishimura, Hiroshi Matsubara, Tissue and Intracellular Localization of Indican and the Purification and Characterization of Indican Synthase from Indigo Plants, *Plant Cell Physiology* (2000), 41, 2, pages 218-225. 200 grams of fresh leaves were flash frozen with liquid nitrogen and ground into a fine powder using a mortar and pestle. The fine powder was suspended in 400 mL of extraction buffer (2 mM EDTA, 20 mM β-mercaptoethanol, 100 mM $H_2KPO_4$, 1× cOmplete protease inhibitor, pH 7.0 in water) and centrifuged at 24500 rcf for 30 min while refrigerated at 4° C. The supernatant was transferred to a new tube and precipitated by adding 600 mL of extraction buffer with 50% w/v polyethylene glycol ($M_w$ 6000 Da) to make 1 L total solution with 30% w/v PEG 6000. This solution was centrifuged at 143000 rcf for 30 min at 4° C. The supernatant of this process was mixed with 25 mL DEAE-Sepharose beads. The beads were washed with 125 mL of wash buffer A (1 mM EDTA, 10 mM β-mercaptoethanol, 50 mM HEPES-NaOH pH 7.0), then washed with 50 mL of wash buffer A+50 mM NaCl, and then protein was eluted with 50 mL of wash buffer A+100 mM NaCl. This 50 mL elution was loaded on a 10 mL hydroxyapatite column, which was washed with 50 mL buffer A1 (1 mM EDTA, 5 mM dithiothreitol, 10% v/v glycerol, 50 mM HEPES-NaOH pH 7.0) and eluted with 98% A1/2% B1 where buffer B1 is buffer A1+500 mM $H_2KPO_4$ pH 7.0. This eluate was loaded onto a Mono Q 5/50 GL column and washed with 5 column volumes of buffer A2 (1 mM EDTA, 5 mM dithiothreitol, 10% v/v glycerol, 10 mM $H_2KPO_4$, 50 mM HEPES-NaOH pH 7.0). Protein was eluted with a gradient from 0-100% Buffer B2 (Buffer A2+200 mM NaCl), at a 1 mL per minute flow rate over 30 min. The protein eluate from 5-9 min was collected and concentrated tenfold using a Millipore 10 kDa molecular weight-cutoff spin column. This concentrate was run on a Superdex 200 size-exclusion column, eluting with 5 mM dithiothreitol, 50 mM HEPES-NaOH pH 7.0. Fractions were lyophilized, resuspended in water, dialyzed in water, and then separated using SDS-PAGE. Proteins trapped in the polyacrylamide gel were electroblotted onto a PVDF membrane and extracted for trypsin digestion and column separation followed by tandem mass spectrometry to identify protein fragments. These protein fragments were correlated to the Transdecoder-predicted sequences using DTAselect and SEQUEST. See David L. Tabb, W. Hayes McDonald, John R. Yates III, DTASelect and Contrast: Tools for Assembling and Comparing Protein Identifications from Shotgun Proteomics, *J Proteome Res*, (2002), 1(1): pages 21-26; Eng J K, McCormack A L, Yates J R, An approach to correlate tandem mass spectral data of peptides with amino acid sequences in a protein database, *J Am Soc Mass Spectrom*, (1994), 5(11), pages 976-989. The sequences with the most complete coverage of matching peptide fragments were selected for further study.

Another sample of total RNA was prepared as described above, but was converted to adaptor-tagged cDNA using the GeneRacer® Kit with SuperScript® III RT and TOPO TA Cloning® Kit for Sequencing from Life Technologies (Carlsbad, CA). Using gene specific oligonucleotide primers, a polymerase chain reaction was used on the adaptor-tagged cDNA library to clone the sequences of interest identified previously. These genes were then Sanger sequenced to confirm their identity and nucleotide sequence.

Example 2

Identification and Isolation of Gene Encoding UDP-Glucose:Glucosyltransferase Isoform 2 from *Polygonum tinctorium*

This Example demonstrates the identification and isolation of the glycosyltransferase gene encoding UDP-glucose:glucosyltransferase isoform 2 from the plant *Polygonum tinctorium*.

The mRNA was extracted from *P. tinctorium* plants and a cDNA library constructed following the procedure as described in Example 1 above.

The cDNA library was analyzed and the predicted UDP-glucose:glucosyltransferase isoform 2 was purified as described in Example 1 above.

Another sample of total RNA was prepared from the plants, and sequences of interest identified and Sanger sequenced to confirm their identity and nucleotide sequence as described in Example 1 above.

Example 3

Identification and Isolation of Gene Encoding a UDP-Glucose:Glucosyltransferase from *Nicotiana tabacum*

The UDP-glucose:glucosyltransferase of interest from *N. tabacum* was identified to be of interest through BLASTP similarity to other glucosyltransferases of interest. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 4

Identification and Isolation of Gene Encoding the UDP-Glucose:Glucosyltransferase UGT72B1 from *Arabidopsis thaliana*

The UDP-glucose:glucosyltransferase UGT72B1 from *A. thaliana* was identified to be of interest through BLASTP similarity to other glucosyltransferases of interest. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 5

Identification and Isolation of Gene Encoding the UDP-Glucose:Glucosyltransferase UGT72E2 from *Arabidopsis thaliana*

The UDP-glucose:glucosyltransferase UGT72E2 from *A. thaliana* was identified to be of interest through BLASTP similarity to other glucosyltransferases of interest. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 6

Identification and Isolation of Gene Encoding the UDP-Glucose:Glucosyltransferase UGT72E3 from *Arabidopsis thaliana*

The UDP-glucose:glucosyltransferase UGT72E3 from *A. thaliana* was identified to be of interest through BLASTP similarity to other glucosyltransferases of interest. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 7

Identification and Isolation of Gene Encoding the Cytochrome P450 BM3 CYP102A1 from *Bacillus megaterium*

The gene encoding the Cytochrome P450 BM3 CYP102A1 from *B. megaterium* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 8

Identification and Isolation of Gene Encoding the Flavin Monooxygenase FMO from *Methylophaga* sp. Strain SK1

The gene encoding the Flavin monooxygenase FMO from *Methylophaga* sp. strain SK1 was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 9

Identification and Isolation of Gene Encoding Sulfotransferase SULT1A1*1 Wildtype from *Homo sapiens*

The gene encoding the sulfotransferase SULT1A1*1 wildtype from *Homo sapiens* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 10

Identification and Isolation of Gene Encoding Sulfotransferase SULT1A1*1 D249G from *H. sapiens*

The gene encoding the sulfotransferase SULT1A1*1 D249G from *Homo sapiens* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 11

Identification and Isolation of Gene Encoding Sulfotransferase SULT1A1*1 Enh1 from *H. sapiens*

The gene encoding the sulfotransferase SULT1A1*1 enh1 from *Homo sapiens* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 12

Identification and Isolation of Gene Encoding Sulfotransferase SULT1A3*1 Wildtype from *H. sapiens*

The gene encoding the sulfotransferase SULT1A3*1 wildtype from *Homo sapiens* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 13

Identification and Isolation of Gene Encoding Sulfotransferase SULT1A3*1 D249G from *H. sapiens*

The gene encoding the sulfotransferase SULT1A3*1 D249G from *Homo sapiens* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 14

Identification and Isolation of Gene Encoding Sulfotransferase SULT1A3*1 Enh1 from *H. sapiens*

The gene encoding the sulfotransferase SULT1A3*1 enh1 from *Homo sapiens* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 15

Identification and Isolation of Genes Encoding UDP-Glucose:Glucosyltransferase from *Indigofera tinctoria* and *Indigofera suffruticosa*

*Indigofera tinctoria* or *Indigofera suffruticosa* plants were grown indoors in a greenhouse or laboratory environment. Samples of leaf tissue were taken from live plants at several points during the day and frozen in liquid nitrogen. These samples were mixed, kept frozen with liquid nitrogen, and crushed using 5 mm. diameter steel bead in a beadbeater at 30 Hz for 2 minutes. Total RNA was extracted from the 100 mg of powdered frozen leaf tissue using the Qiagen RNEasy Plant Mini kit obtained from Qiagen GMBH (Hilden, Germany), in accordance with the manufacturer recommended protocol. The total RNA was converted to adaptor-tagged cDNA using the GeneRacer® Kit with SuperScript® III RT and TOPO TA Cloning® Kit for Sequencing from Life Technologies (Carlsbad, CA). Using gene specific oligonucleotide primers, a polymerase chain reaction was used on the adaptor-tagged cDNA library to clone the sequences of interest identified through BLASTX similarity to successful sequences found in *Polygonum tinctorium*.

Example 16

Identification and Isolation of Gene Encoding Sulfohydrolase atsA from *Pseudomonas aeruginosa*

The gene encoding the sulfohydrolase atsA from *P. aeruginosa* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 17

Identification and Isolation of Genes Encoding the Sulfohydrolase Arylsulfatase3 and the Sulfohydrolase Companion Anaerobic Sulfatase Maturase (ansME) from *Providencia stuartii*

The genes encoding the sulfohydrolase arylsulfatase3 and the sulfohydrolase companion anaerobic sulfatase maturase (ansME) from *P. stuartii* was identified to be of interest by review of the reference source listed in Table 1. This sequence was cloned via polymerase chain reaction using as template a synthetic piece of DNA ordered from Integrated DNA Technologies, Inc. (Coralville, IA). The product of the polymerase chain reaction was cloned into an expression vector as described in Example 18.

Example 18

Construction of Recombinant DNA Plasmids

This Example demonstrates the construction of recombinant DNA plasmids for use in transforming host cells.

Plasmids were constructed using a variant of the "Golden Gate" method. In the design stage, fragments were planned such that they would have flanking BsaI, BsmBI, or BpiI type IIS restriction enzyme recognition sites. These sites were set up such that, upon cleavage with one of these type IIS restriction enzymes, fragments to be assembled together would expose matching overhangs or "sticky ends," allowing multiple distinct fragments to assemble in an ordered fashion. This assembly was achieved by mixing together, in 5 μL of water, from 50-200 ng of each individual plasmid or PCR product to contribute a fragment to the assembly. To this mixture was added 1 μL of 10×NEB ligase buffer from New England Biolabs, Inc. (Ipswich, MA), 3 μL of water, and 0.5 μL each of 3000 kU/mL T7 ligase and 10 kU/mL type IIS restriction enzyme, from New England Biolabs, Inc. The 10 μL solution was pipetted to mix, and placed in a thermocycler to run the following temperature program: 45° C. for 2 min, then 20° C. for 5 min, repeated 25 times, followed by 60° C. for 10 min to enhance digestion of half-assembled product and 80° C. for 10 min to achieve heat inactivation of enzymes. The assembled plasmid was then transformed into the host cells.

Example 19

Transformation of E. coli Host Cells

This Example demonstrates the transformation of E. coli host cells with a plasmid for heterologous gene expression. Plasmids were constructed following the procedure described in Example 18.

A TSS buffer, 100 mL total, was prepared and filtered with a 0.2 μm filter for sterility, the TSS buffer containing of 85 mL LB media, 10 g polyethylene glycol 3350 in 5 mL $H_2O$, 5 mL DMSO, 3 mL $H_2O$, and 2 mL of 1 M $MgCl_2$. A second buffer was prepared, KCM5×, containing 500 mM KCl, 150 mM $CaCl_2$, and 250 mM $MgCl_2$ in water. The host cell E. coli strain was inoculated by dilution 1:1000 of 1 mL of saturated culture into 1 L LB media, in a 2 L flask. This was kept shaking at 250 rpm and 37° C. until the E. coli had grown to an optical density at 600 nm (OD600) of 0.5. Once grown, the culture was centrifuged at 4800 rcf for 5 min, then resuspended in 100 mL of TSS buffer while kept on ice. A 50 μL aliquot of these cells were mixed with 0.5 μL of the appropriate plasmid, and 10 μL of KCM5× buffer was added. The mixture was kept on ice for 2 min, transferred to a 42° C. water bath for 90 sec, incubated at 37° C. for one h, and then the entire mixture was plated onto an LB-agar plate supplemented with the appropriate selective marker. These plates were incubated at 37° C. to allow transformed cell colonies to grow.

Example 20

Transformation of S. cerevisiae Host Cells

This Example demonstrates the transformation of S. cerevisiae host cells with a plasmid for heterologous gene expression. Plasmids were constructed following the procedure described in Example 18.

Growth media (YPD) was prepared by dissolving 20 g of glucose, 10 g of yeast extract, and 20 g of peptone in 1 L of distilled water, and then filtering the resulting mixture with a 0.2 μm filter for sterility. The host cell S. cerevisiae strain was inoculated by dilution 1:100 from 50 μL of saturated culture into 5 mL of YPD in a culture tube. This culture was incubated at 250 rpm shaking, 30° C. for approximately 5 hours, until an OD600 of 0.8 was reached. At this point, the cells were transferred to a centrifuge tube and spun down at 4800 rcf for 5 min. The supernatant was discarded and the pellet was resuspended with 5 mL water. The mixture was spun down again at 4800 rcf for 5 min, and the supernatant discarded and the cells resuspended with 5 mL 100 mM lithium acetate in water. The mixture was spun down again at 4800 rcf for 5 min, the supernatant discarded and the cells resuspended with 50 μL of water. To this was added 36 μL of 1 M lithium acetate in water, 240 μL of 50% w/v polyethylene glycol 3350 in water, 25 μL of 2 mg/mL salmon sperm DNA in water, and 1 μL of the plasmid of interest in water. The resulting mixture was vortexed for one minute and transferred to a 42° C. heat bath to heat shock for 30 min. After heat shock, the cell mixture was transferred to ambient temperature and centrifuged at 2000 rcf for 3 min. The supernatant was discarded, the cells were resuspended with 60 μL water, and the cell solution was plated onto SD-dropout agar plates, where one amino acid has been removed from the media to select for cells carrying an auxotrophic marker. See Gietz R D, Schiestl R H, High-efficiency yeast transformation using the LiAc/SS carrier DNA/PEG method, Nat Protoc (2007), 2(1), pages 31-4. These plates were then incubated at 30° C. to allow transformed cell colonies to grow.

Example 21

Expression and Purification of Hydrolases in E. coli Host Cells

This Example demonstrates purification of hydrolases which were heterologously expressed in E. coli host cells. The E. coli host cells were transformed with recombinant plasmids for inducible expression of hexahistidine-tagged proteins following the procedure of Example 19. The strain BL21 DE3 was typically used for expression.

Hydrolase expression: A 2 L flask containing 0.5 L LB media supplemented with 100 μg/mL ampicillin was inoculated with the transformed host cells by the addition of 5 mL of saturated culture, a 1:100 dilution. This was kept shaking at 250 rpm and 37° C. until the E. coli had grown to an OD600 of about 0.5. Once grown, the culture was induced to produce protein by addition of isopropyl β-D-1-thiogalactopyranoside (IPTG) to a final concentration of 1 mM. The flask was then allowed to continue shaking at 250 rpm and 37° C. for 16 h.

Hydrolase purification: Once incubation was complete, cells were harvested by centrifugation at 4800 rcf for 5 min. The supernatant was discarded and the cells were resuspended in 35 mL of ice-cold lysis buffer containing 150 mM NaCl, 25 mM imidazole, and 25 mM Tris pH 8.0 in water. Cells were kept at 4° C. and sonicated for 30 sec at maximum amplitude to achieve lysis. Lysate was centrifuged at 24500 rcf for 10 min, and the supernatant mixed with 4 mL nickel-nitriloacetic acid agarose beads for 10 min. The beads and supernatant were packed into a column and allowed to flow through by gravity. The column was washed twice with 30 mL of fresh lysis buffer to remove any unbound protein, and the hydrolase was eluted off of the column by running 10 mL of elution buffer (150 mM NaCl, 500 mM imidazole, and 25 mM Tris pH 8.0 in water) through the column. The eluate was concentrated using a Millipore 10 kDa molecular weight-cutoff spin column and glycerol was added to a final concentration of 10% v/v, then aliquots of the hydrolase were frozen at −80° C.

Example 22

In Vivo Production of (3-(β-D-glucosido)indole) in E. coli Host Cells Heterologously Expressing Glucosyltransferases This Example demonstrates the production of (3-(β-D-glucosido)indole), also known as indican, by different E. coli host cells expressing recombinant glucosyltransferases.

Plasmids were constructed following the procedure described in Example 18. E. coli host cells were transformed with recombinant plasmids according to Example 19, to produce a series of host cells expressing both the oxygenase Flavin-containing monooxygenase (FMO) and one glucosyltransferase selected from UGT72E3 from A. thaliana, UGT72B1 from A. thaliana, AHZ08761.1 from N. tabacum, UGT72E2 from A. thaliana, UGT isoform 1 from P. tinctorium, and UGT isoform 2 from P. tinctorium.

For each host cell culture, a 24-well culture block containing 3 mL per well of EZ-Rich MOPS culture medium obtained from Teknova (Hollister, CA) supplemented with 50 μg/mL spectinomycin and 5 mM L-tryptophan and 2% w/v glucose was inoculated with one recombinant strain of E. coli by scraping a single colony from an agar plate. Each block was kept at 37° C. with shaking at 750 rpm for 12 h.

After incubation, indican was extracted by taking 360 μL of each reaction and adding 40 μL of 50% w/v aqueous NH$_4$OH to achieve a final volume of 400 μL supplemented with 5% w/v NH$_4$OH. This mixture was allowed to sit for 5 minutes. Samples were vortexed with 800 μL of methyl tert-butyl ether for 10 min, centrifuged at 20000 rcf for 5 min, and the aqueous phase separated by LC/MS on a C18 column. Indican was detected via time-of-flight mass spectrometry using a negative electrospray ion source.

Figure 2:
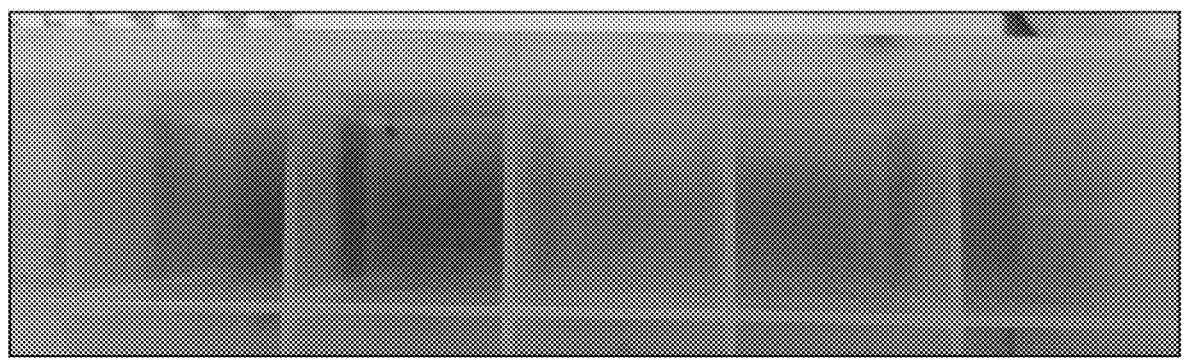
FIG. 2 depicts an image of *E. coli* host cell cultures heterologously expressing different recombinant glucosyltransferases and a heterologous flavin-containing monooxygenase (FMO).

FIG. 1 depicts the liquid-chromatography mass spectrometry (LC-MS) traces of each sample quantified. FIG. 2 depicts a photograph of the host cells grown in LB supplemented with 50 μg/mL spectinomycin expressing, from right to left, UGT72E2, UGT72E3, AHZ08761.1, UGT isoform 1 from P. tinctorium, and UGT isoform 2 from P. tinctorium. The blue coloration is due to indigo production.

Example 23

Conversion of Indican Secreted from E. coli Host Cells to Indigo

This example demonstrates the conversion of indican (3-(β-D-glucosido)indole) secreted by a recombinant E. coli culture to indigo in the presence of β-glucosidase.

Plasmids were constructed following the procedure described in Example 18. E. coli host cells were transformed with recombinant plasmids according to Example 19 to produce host cells expressing the UGT AHZ08761.1 glucosyltransferase Nicotiana tabacum. A 4 mg/mL solution of β-glucosidase bglA from B. circulans was obtained via protein purification as according to Example 21.

For each host cell culture, a 24-well culture block containing 3 mL of LB culture medium per well supplemented with 50 μg/mL spectinomycin was inoculated with one recombinant strain of E. coli by scraping a single colony from an agar plate. Each block was kept at 37° C. with shaking at 750 rpm for 12 h.

Figure 3:
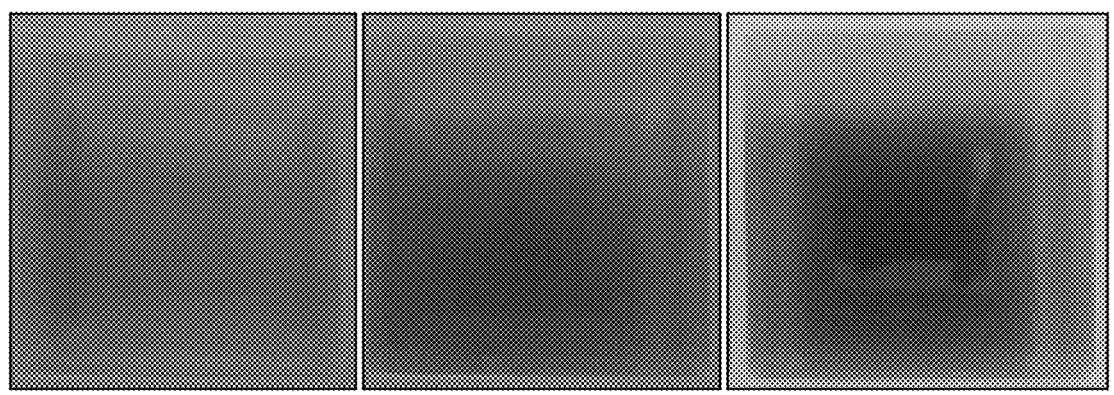
FIG. 3 depicts images of an *E. coli* host cell culture heterologously expressing a recombinant glucosyltransferase and a heterologous oxygenase FMO, immediately after the addition of β-glucosidase (left), 75 min after the addition of β-glucosidase (middle), and 20.5 h after the addition of β-glucosidase (right).

A 50 μL aliquot of 4 mg/mL β-glucosidase solution was then added to the culture and allowed to sit at ambient temperature for 20.5 h. FIG. 3 depicts photographs of the culture taken immediately after the addition of β-glucosidase (left), 75 min after the addition of β-glucosidase (middle), and 20.5 h after the addition of β-glucosidase (right). Without wishing to be bound by any theory, this demonstrates that indican is being made and secreted by the recombinant E. coli, and the indican remains accessible to a β-glucosidase. The presence and accessibility of indican in the culture media allows for indicates the media may be used to dye objects directly.

Example 24

In vivo Production of 3-(β-D-glucosido)indole in Yeast Strains Heterologously Expressing an Oxygenase and Different Glucosyltransferases This example demonstrates the in vivo production of 3-(β-D-glucosido)indole, also known as indican, by cultures of Saccharomyces cerevisiae heterologously expressing the oxygenase cytochrome P450 CYP102A1 from Bacillus megaterium and different glucosyltransferases, when supplemented with indole. This Example also demonstrates the effect that optional coexpression of UDP-glucose synthesis enzymes UGP1 and PGM2 from S. cerevisiae, and optional coexpression of the oligosaccharide transporter CDT1 from Neurospora crassa have on indican production.

Plasmids were constructed following the procedure described in Example 18. S. cerevisiae host cells were transformed with recombinant plasmids following the procedure described in Example 20, to produce a series of host cells expressing the oxygenase CYP102A1 and one glucosyltransferase selected from UGT72B1 from A. thaliana, UGT AHZ08761.1 from N. tabacum, UGT isoform 1 from P. tinctorium, and UGT isoform 2 (mut) from P. tinctorium; optionally overexpressing UGP1 and PGM2 from S. cerevisiae; and optionally overexpressing CDT1 N. crassa.

Two control host cell cultures were also produced, one expressing CYP102A1 with no recombinant glucosyltransferase, and one expressing no recombinant CYP102A1 or glucosyltransferase. Indole was obtained from Sigma-Aldrich (St. Louis, MO).

For each host cell culture, one well in a 24-well culture block containing 3 mL of SD-Uracil dropout medium per well was inoculated with the recombinant strain of S. cerevisiae by scraping colony growth off of an agar plate. The block was kept at 30° C. with shaking at 750 rpm overnight. The next day, the 3 mL cell solution was centrifuged at 4800 rcf for 5 min. Cells were resuspended in 600 μL phosphate buffered saline, pH 7.4, supplemented with 1.26 mM glucose; of this, 100 μL was diluted into 3000 μL phosphate buffered saline, pH 7.4, supplemented with 1.26 mM glucose, 1% dimethyl sulfoxide, and 5 mM indole. 500 μL of this mixture was transferred to a 96-well block, which was then incubated at 30° C. with shaking at 750 rpm for 6 h.

After incubation, indican was extracted by taking 360 μL of each reaction and adding 40 μL of 50% w/v aqueous NH$_4$OH to achieve a final volume of 400 μL supplemented with 5% w/v NH$_4$OH. This mixture was allowed to sit for 5 min. Samples were then vortexed with 800 µL of methyl tert-butyl ether for 10 min, centrifuged at 20000 rcf for 5 min, and the aqueous phase separated by LC/MS on a C18 column. Indican was detected via time-of-flight mass spectrometry using a negative electrospray ion source.

Figure 4:
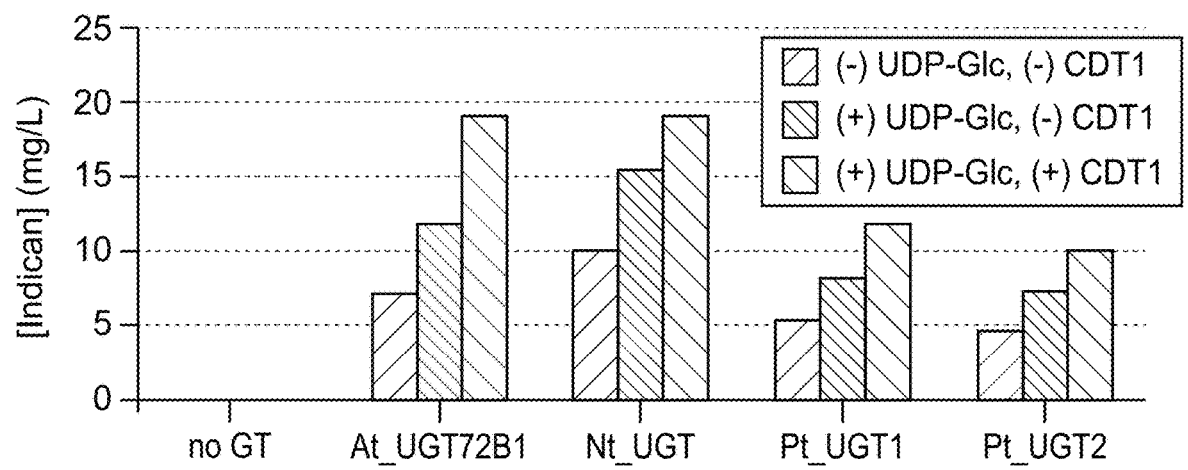
FIG. 4 depicts a graph comparing the concentration of indican of each *E. coli* host cell culture expressing a different glucosyltransferase and an FMO, and additionally with and without expression of UDP-glucose synthesis enzymes ("UDP-Glc"), and the oligosaccharide transporter CDT1.

FIG. 4 depicts a graph comparing the concentration of indican of each culture expressing a glucosyltransferase, and additionally with and without expression of both UGP1 and PGM2 ("UDP-Glc"), and the transporter CDT1. These results show that expression of UGP1, PGM2 and CDT1 lead to higher levels of indican production. This indicates that both UGP1 and PGM2, and the oligosaccharide transporter CDT1 contribute to indican production in *S. cerevisiae*.

Example 25

Use of Indigo and Indican in the Presence of *Bacillus circulans* β-Glucosidase to Dye Cloth This example demonstrates the level of cloth dyeing obtained when using indican (3-(β-D-glucosido)indole) or indigo in the presence of the β-glucosidase bglA from *Bacillus circulans*.

Indican and indigo were purchased from Sigma-Aldrich (St. Louis, MO). A 4 mg/mL solution of β-glucosidase bglA from *B. circulans* was obtained via protein purification according to Example 21.

Separate solutions of 10 g/L indigo or indican were prepared by suspension in water; the indigo remained in microscale crystals, while the indican dissolved. A 1 square inch piece of undyed cotton cloth was added to a 5 mL Eppendorf tube containing either the indigo solution or the indican solution. The cloth was allowed to soak in the liquid for 10 min at ambient temperature. The cloth pieces were removed from the solution and laid flat on wax paper. Then, 100 µL of a 4 mg/mL β-glucosidase solution was pipetted unevenly across each cloth piece. The cloth pieces were incubated at ambient temperature for 6 h, then washed repeatedly with water and allowed to dry.

Figure 5:
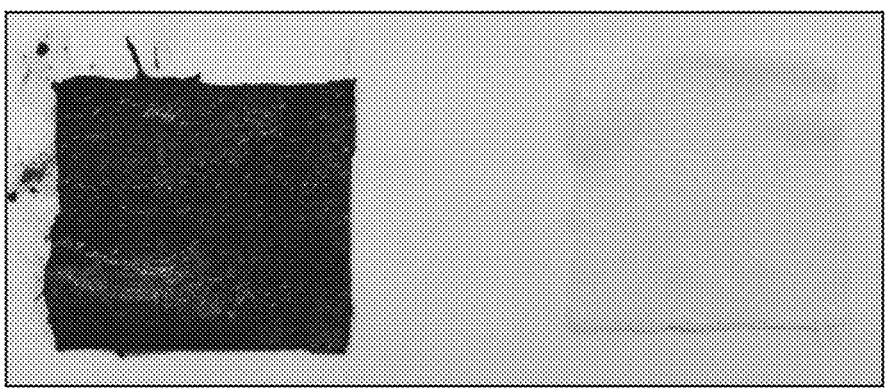
FIG. 5 depicts the appearance of cloth pieces after incubation with indigo or indican (top), 5 min after application of β-glucosidase (middle), and after six hours of incubation followed by washing and drying (bottom).
Figure 5:
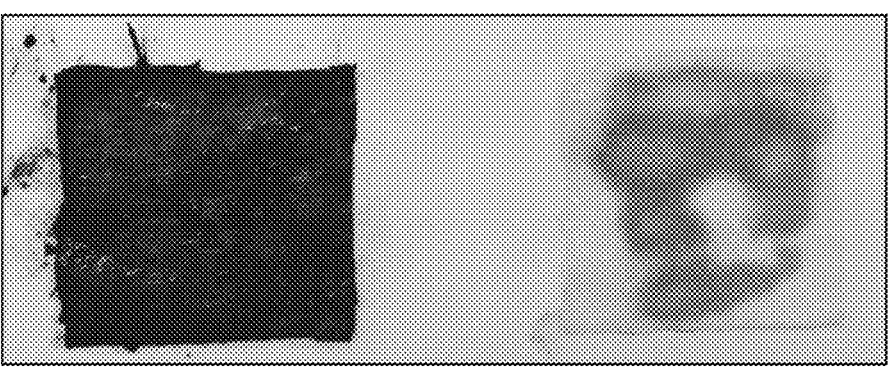
Figure 5:
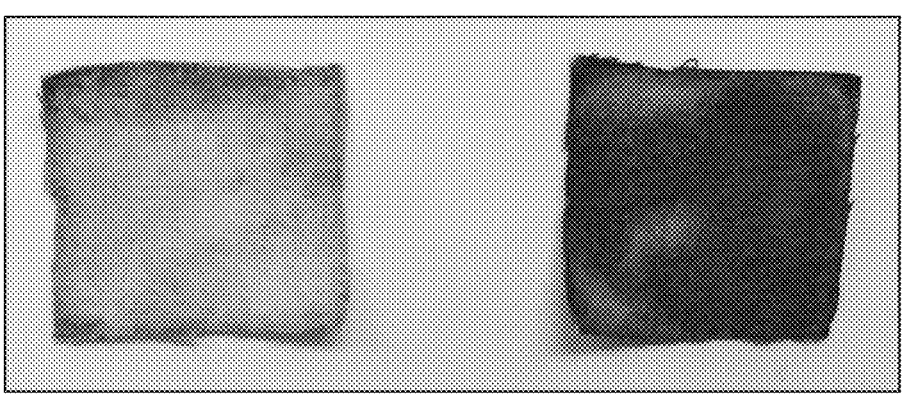

FIG. 5 shows the appearance of the cloth pieces after incubation with indigo or indican (top), the cloth pieces 5 min after application of β-glucosidase (middle), and the degree of color remaining after washing each piece of cloth (bottom). These results indicate that enzymatic hydrolysis of indican on fabric can be used to generate indigo dyeing that remains even after repeated washing.

Example 26

In Vitro Production of Indigoid Dyes in the Presence of a Sulfatase

This example demonstrates the in vitro conversion of sulfated indigoid dye precursors to indigoid dyes in the presence of the sulfatase atsA from *P. aeruginosa*.

The sulfated dye precursor 1H-indol-3-yl sulfate was obtained from Sigma-Aldrich (St. Louis, MO) and dissolved in water to obtain a stock concentration of 10 mM. The sulfated dye precursor 5-bromo-4-chloro-1H-indol-3-yl sulfate was obtained from Sigma-Aldrich (St. Louis, MO) and dissolved in dimethyl sulfoxide (DMSO) to obtain a stock concentration of 10 mM.

Following the procedure described in Example 19, *E. coli* host cells were transformed with plasmids expressing the hydrolase atsA from *Pseudomonas aeruginosa*. These transformed cells were grown a tube filled with 5 mL LB medium supplemented with 100 µg/mL ampicillin, and left shaking at 250 rpm, 37° C., overnight. The next day, the 5 mL *E. coli* saturated culture was centrifuged at 4800 rcf for 5 min. Spent media supernatant was removed and saved for usage in the assay as "supernatant."

Figure 6:
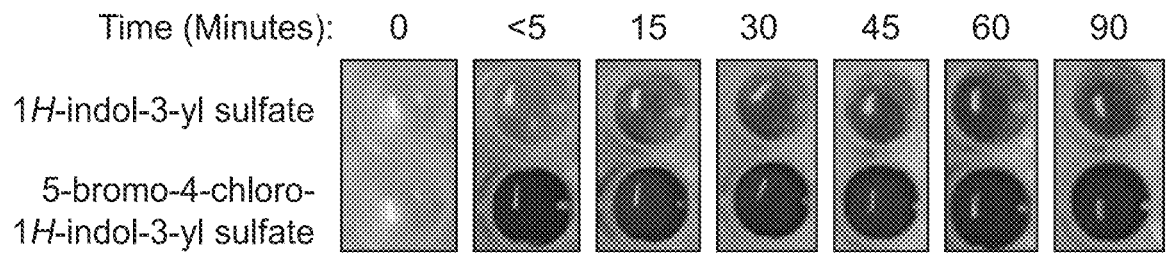
FIG. 6 depicts images of the conversion of indigoid dye precursors to indigoid dyes in the presence of the sulfatase atsA, from *P. aeruginosa*.

To two wells in a plastic 96-well plate were added 20 µL of a 10 mM solution of one of the sulfated dye precursor substrates. To the 5-bromo-4-chloro-1H-indol-3-yl sulfate containing well was added 20 µL of deionized water. To the f 1H-indol-3-yl sulfate containing well was added 20 µL of dimethyl sulfoxide (DMSO). To this mixture, 160 µL of supernatant was added for a final concentration of 10% DMSO and 1 mM substrate. During this procedure, the plate was kept cold until all reagents had been added and mixed. The mixtures were then allowed to incubate for 90 min at ambient temperature, and monitored visually for production of indigoid dyes over time. FIG. 6 depicts images of each well taken over time, showing the production of indigoid dyes from indigoid dye precursors in the presence of the sulfatase atsA.

Example 27

In Vivo Production of 1H-Indol-3-Yl Sulfate by *E. coli* Heterologously Expressing Different Sulfatases This example demonstrates the production of 1H-indol-3-yl sulfate by *E. coli* cultures expressing different recombinant sulfatases and supplemented with 1H-indol-3-yl acetate and 3'-phosphoadenosine-5'-phosphosulfate (PAPS).

The compounds 1H-indol-3-yl acetate and 3'-phosphoadenosine-5'-phosphosulfate (PAPS). were obtained from Sigma-Aldrich (St. Louis, MO). *E. coli* BL21 DE3 host cells were transformed with recombinant plasmids according to Example 19 to produce host cells inducibly expressing SULT1A1*1 wildtype from *Homo sapiens*, SULT1A1*1 D249G from *Homo sapiens*, SULT1A1*1 enh1 from *Homo sapiens*, SULT1A3*1 wildtype from *Homo sapiens*, SULT1A3*1 D249G from *Homo sapiens*, or SULT1A3*1 enh1 from *Homo sapiens*.

For each host cell strain, a well in a 24-well culture block was filled with 3 mL of LB culture medium supplemented with 34 µg/mL chloramphenicol and inoculated by 1:100 dilution of saturated overnight culture with one recombinant strain of *E. coli*. The block was incubated while shaking at 750 rpm at 37° C. for 3 h, after which point isopropyl β-D-1-thiogalactopyranoside (IPTG) was added to a final concentration of 0.5 mM. The block was then incubated for another 16 h, with shaking at 750 rpm and at a temperature of 37° C. At this point, the block was centrifuged at 4800 rcf for 3 min to collect the cells. The supernatant was discarded and the cell pellets were transferred into an anaerobic environment, where they were each resuspended with 600 µL of LB supplemented with 34 µg/mL chloramphenicol, concentrating the cells five-fold. 58.5 µL of this cell resuspension was supplemented, bringing the total volume to 75 µL and a final concentration of 2 mM 1H-indol-3-yl acetate, 2% v/v dimethyl sulfoxide and 2 mM PAPS. This mixture was sealed and incubated for 24 h at 37° C., to allow native esterase activity of the cells to hydrolyze 1H-indol-3-yl acetate to indoxyl. At the end of the incubation, the mixture was exposed to air to oxidize any unprotected indoxyl.

Figure 7:
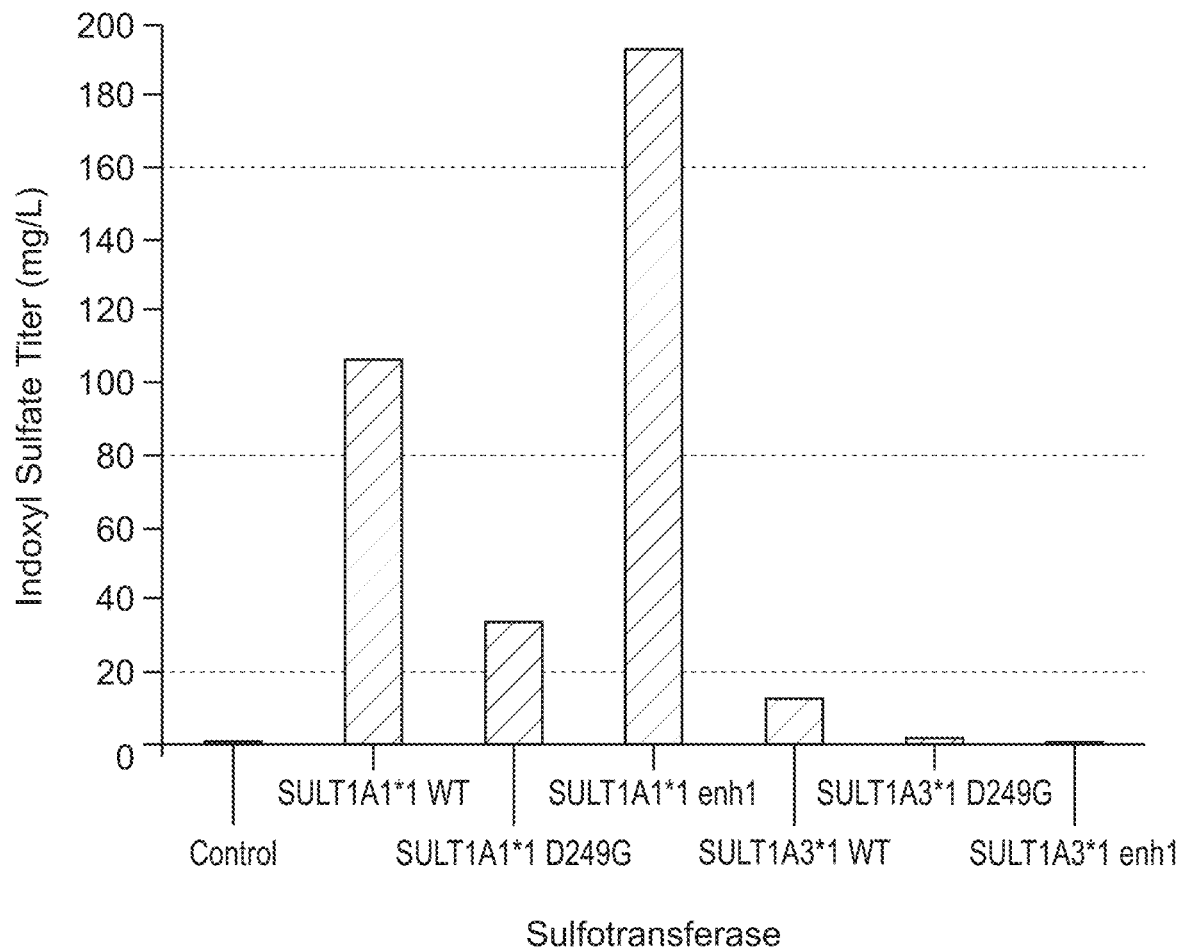
FIG. 7 depicts a graph of the concentration of 1H-indol-3-yl sulfate produced by *E. coli* host cell cultures heterologously expressing different sulfotransferases.

Following exposure to air, the quantity of 1H-indol-3-yl sulfate produced was measured by extraction and LC/MS. To extract the 1H-indol-3-yl sulfate, the 75 µL reaction was diluted and aqueous $NH_4OH$ added to achieve a final volume of 400 µL supplemented with 5% w/v $NH_4OH$. This mixture was allowed to sit for 5 min. Samples were then vortexed with 800 µL of methyl tert-butyl ether for 10 min, centrifuged at 20000 rcf for 5 min, and the aqueous phase separated by LC/MS on a C18 column. 1H-indol-3-yl sulfate was detected via time-of-flight mass spectrometry using a negative electrospray ion source. FIG. 7 depicts a graph of the concentration of 1H-indol-3-yl sulfate produced by each strain of *E. coli*.

Example 28

Comparison of Different Hydrolases in the In Vitro Production of Dyes from Sulfated Dye Precursors This example demonstrates the use of four different hydrolase enzymes in the in vitro conversion of sulfated dye precursors to dyes.

The sulfated dye precursors 1H-indol-3-yl sulfate and 4-nitrophenyl sulfate were obtained from Sigma-Aldrich (St. Louis, MO) and dissolved in water to obtain stock concentrations of 10 mM. The sulfated dye precursor 5-bromo-4-chloro-1H-indol-3-yl sulfate was obtained from Sigma-Aldrich (St. Louis, MO) and dissolved in dimethyl sulfoxide (DMSO) to obtain a stock concentration of 10 mM. The sulfated dye precursor 4-nitrocatechol sulfate was dissolved in water to obtain a stock concentration of 1 mM.

Following the procedure described in Example 19, *E. coli* host cells were transformed with plasmids to express the hydrolases yidJ from *Escherichia coli*, atsA from *Pseudomonas aeruginosa*, or both arylsulfatase3 and the companion maturase anSME from *Providencia stuartii*. The transformed cells were grown in tubes filled with 5 mL LB medium supplemented with 100 µg/mL ampicillin with shaking at 250 rpm, 37° C., overnight. The next day, the 5 mL *E. coli* saturated cultures were centrifuged at 4800 rcf for 5 min. Spent media supernatant was removed and saved for usage in the assay as "media." Pellets were resuspended with 3 mL 1.25× phosphate buffered saline (PBS) pH 7.4 and then centrifuged again. This supernatant was discarded and the pellets were once more resuspended with 3 mL 1.25× phosphate buffered saline (PBS) pH 7.4. Of this 3 mL of PBS-washed cells, 1.5 mL was kept for usage as "cell solution." The final remaining 1.5 mL of cells was lysed by adding 160 uL of 10× Bugbuster HT Protein Extraction Reagent obtained from EMD/Millipore-Merck KGaA (Darmstadt, Germany). In this way, the final component, "cell lysate," was produced.

Figure 8:
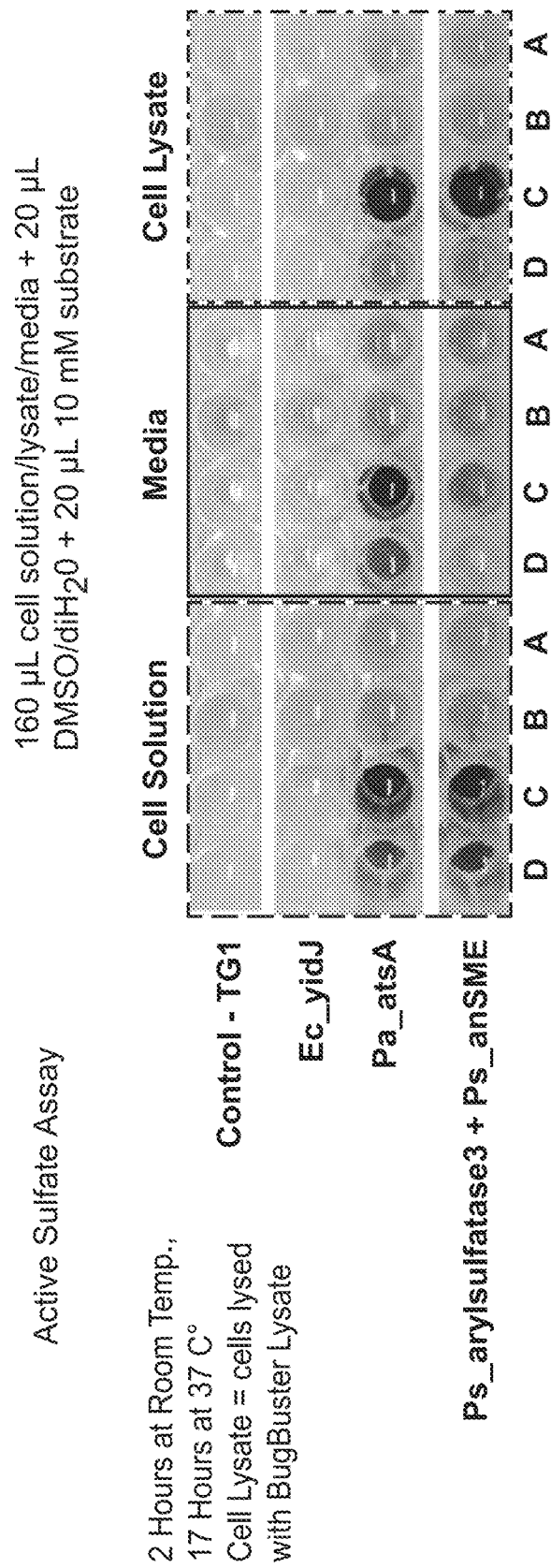
FIG. 8 depicts a photograph of different dyes produced from sulfated dye precursors in the presence of different hydrolases.

To a plastic 96-well plate was added 20 µL of one of the prepared sulfated dye precursor substrate solutions. To this solution was added 20 µL of deionized water for the substrate 5-bromo-4-chloro-1H-indol-3-yl sulfate, or dimethyl sulfoxide (DMSO) for all other substrates. To this mixture, 160 µL of cell solution, supernatant, or cell lysate was added for a final concentration of 10% DMSO and 0.01 mM of 4-nitrocatechol sulfate, or 1 mM of all other substrates. The plate was incubated for 2 h at room temperature, followed by 17 h at 37° C., at which point the qualitative production of indigoid dyes was visually determined. FIG. 8 depicts a photograph of the wells taken at the 19-hour point, with indigoid dye production indicated by blue coloration and other dye production indicated by yellow coloration. These results indicate that *E. coli* strain TG1 naturally lacks significant sulfate hydrolase activity, but the hydrolases yidJ from *Escherichia coli*, atsA from *Pseudomonas aeruginosa*, or arylsulfatase3 and companion maturase anSME from *Providencia stuartii* can cleave sulfated dye precursors.

Example 29

Production of Halogenated Indigoid Dyes by *E. coli* Host Cells Expressing FMO

This example demonstrates the in vivo production of halogenated indigoid dyes by *E. coli* host cells expressing a Flavin-containing monooxygenase (FMO).

The halogenated indoles 5-chloro-1H-indol-3-ol, 6-chloro-1H-indol-3-ol, 7-chloro-1H-indol-3-ol, 5-bromo-1H-indol-3-ol, 6-bromo-1H-indol-3-ol, and 7-bromo-1H-indol-3-ol were obtained from Sigma-Aldrich (St. Louis, MO). *E. coli* host cells were transformed with recombinant plasmids according to Example 19 to produce host cells expressing the FMO from *Methylophaga* sp. strain SK1.

Figure 9:
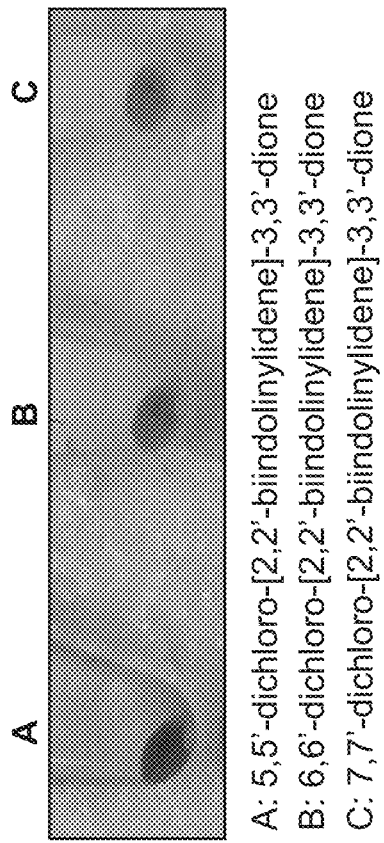
FIG. 9 depicts halogenated indigoid dyes produced by contacting substituted haloindoles with an *E. coli* host cell expressing a heterologous oxygenase FMO.

For each halogenated indole, one well in a 24-well culture block containing 2 mL of LB culture medium per well supplemented with 100 µg/mL ampicillin was inoculated with the recombinant strain of *E. coli* by 1:1000 dilution of saturated culture. The block was kept at 37° C. with shaking at 750 rpm overnight. The next day, the 2 mL cell solution was centrifuged at 4800 rcf for five minutes. Cells were resuspended in 400 µL phosphate buffered saline, pH 7.4, supplemented with 1.26 mM glucose, 1% dimethyl sulfoxide, and 1 mM of a halogenated indole. Cells were incubated at 37° C. for 16 h, resuspended, and 200 µL was transferred to 8-well strip tubes. Pellets were collected by centrifugation at 4800 rcf for 5 min, at which point a photograph was taken. FIG. 9 depicts the color of the indigoid dyes obtained. These color results match reference images of these dyes, demonstrating the presence of halogenated indigoid dyes, indicating the *E. coli* whole-cell catalyzed conversion of precursors to dyes was successful.

Example 30

Production of Indigo Dye by *E. coli* Host Cells Expressing FMO

This example demonstrates the in vivo production of indigo dye by *E. coli* host cells expressing a Flavin-containing monooxygenase (FMO). *E. coli* host cells were transformed with recombinant plasmids according to Example 19 to produce host cells expressing the FMO from *Methylophaga* sp. strain SK1.

Figure 10:
FIG. 10 depicts the production of indigo in *E. coli* host cells expressing a heterologous oxygenase FMO.

To a 250 mL flask was added 50 mL LB culture medium supplemented with 100 µg/mL ampicillin and 3.7 mM L-tryptophan, and inoculated by 1:1000 dilution of saturated culture of a recombinant strain of *E. coli*. The recombinant strain of *E. coli* was constitutively expressing the FMO from *Methylophaga* sp. strain SK1. The flask was kept at 37° C. with shaking at 250 rpm for 24 h. FIG. 10 depicts the color of the indigo dyes obtained. These results demonstrate facile microbial biosynthesis of indigo dye from host cells heterologously expressing an FMO.

Example 31

This Example illustrates that host cells having knockouts in certain genes exhibit lower rates of hydrolysis of indoxyl acetate.

Methods

5×KO (Δaes, ΔyjfP, ΔbioH, ΔyeiG, ΔfrmB) and 11×KO (Δaes, ΔyjfP, ΔbioH, ΔyeiG, ΔfrmB, ΔentH, ΔydiL, ΔtesA, ΔnanS, ΔyqiA, Δybf) knockouts of *E. coli* strain MG1655 were generated using the MAGE technique (See Wang H H, Isaacs F J, Can P A, Sun Z Z, Xu G, Forest C R, Church G M, Programming cells by multiplex genome engineering and accelerated evolution, Nature (2009), 460, pages 894-898) using oligonucleotide primers designed using the MODEST software package (See Bonde M T, Klausen M S, Anderson M V, Wallin A I N, Wang H H, Sommer M O A, MODEST: a web-based design tool for oligonucleotide-mediated genome engineering and recombineering, Nucl Acids Res, (2014), 42, pages W408-W415) and validated using polymerase chain reaction.

| Gene | Ordered Locus Name | Extended Name |
|---|---|---|
| aes | b0476 | Acetyl esterase |
| yjfP | b4190 | Esterase yjfP |
| bioH | b3412 | Pimeloyl-[acyl-carrier protein] methyl ester esterase |
| yeiG | b2154 | S-formylglutathione hydrolase YeiG |
| frmB | b0355 | S-formylglutathione hydrolase FrmB |
| entH | b0597 | Proofreading thioesterase EntH |
| ydiL | b1689 | Uncharacterized protein YdiL |
| tesA | b0494 | Acyl-CoA thioesterase I |
| nanS | b4309 | Probable 9-O-acetyl-N-acetylneuraminic acid deacetylase |
| yqiA | b3031 | Esterase YqiA |
| ybfF | b0686 | Esterase YbfF |
| ypfH | b2473 | Esterase YpfH |
| argE | b3957 | Acetylornithine deacetylase |
| frsA | b0239 | Esterase FrsA |
| ybgC | b0736 | Acyl-CoA thioester hydrolase YbgC |
| tnaA | b3708 | Tryptophanase |

Bacterial colonies (wild type or knockouts) were grown in LB for 16 hours at 37° C. (200 rpm shaking). Cells were pelleted and resuspended to a concentration of OD600=2 in phosphate buffered saline pH 7 with 5% DMSO and 1 mM indoxyl acetate added. Indoxyl acetate hydrolysis rate was then determined by measuring the increase in free indoxyl fluorescence (excitation 410 nm, emission 490 nm) for 30 minutes. Fluorescence increases were observed to be linear.

Results and Discussion

Figure 11:
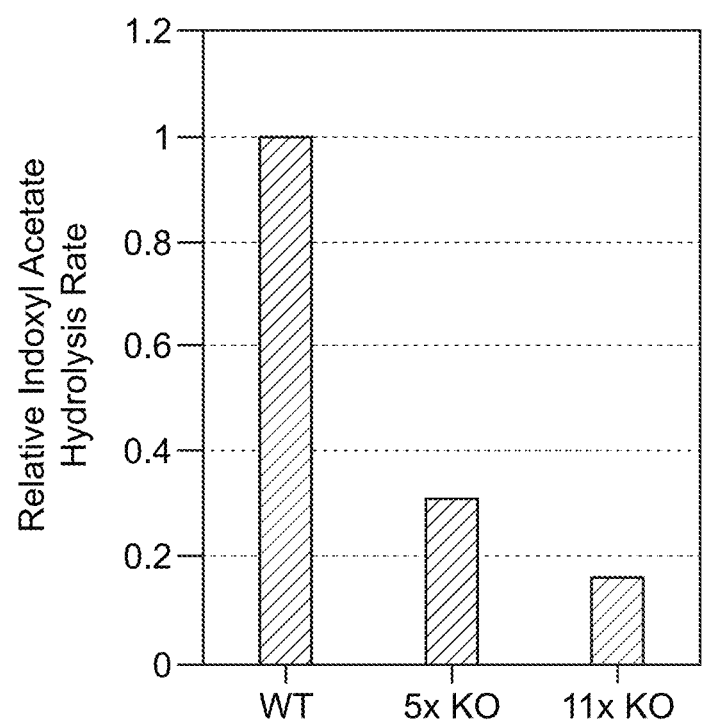
FIG. 11 depicts the relative rate of indoxyl acetate hydrolysis by wild-type *E. coli* strain MG1655 and two knockout strains upon incubation with 1 mM indoxyl acetate. Hydrolysis was calculated by an initial increase in indoxyl fluorescence when 1 mM indoxyl acetate is mixed with saturated culture (2 OD600 units per mL) in phosphate buffered saline pH 7 and 5% DMSO. 5×KO: Δaes, ΔyjfP, ΔbioH, ΔyeiG, ΔfrmB. 11×KO: Δaes, ΔyjfP, ΔbioH, ΔyeiG, ΔfrmB, ΔentH, ΔydiL, ΔtesA, ΔnanS, ΔyqiA, ΔybfF

In FIG. 11, 5×KO (Δaes, ΔyjfP, ΔbioH, ΔyeiG, ΔfrmB and 11×KO (Δaes, ΔyjfP, ΔbioH, ΔyeiG, ΔfrmB, ΔentH, ΔydiL, ΔtesA, ΔnanS, ΔyqiA, ΔybfF), exhibit decreased rates of indoxyl acetate hydrolysis as compared to a WT cell. Thus, it appears that knockouts of the following genes enhance stability of compounds containing an acetate moiety (including indoxyl acetate): Δaes, ΔyjfP, ΔbioH, ΔyeiG, ΔfrmB, ΔentH, ΔydiL, ΔtesA, ΔnanS, ΔyqiA, ΔybfF, ΔypfH, ΔargE, ΔfrsA, ΔybgC, ΔtnaA. This enhanced stability can contribute to higher product yields in fermentative processes.

TABLE 1

Sequences

| SEQ ID NO: | Name | Function | Amino Acid Sequence | Reference/ Source |
|---|---|---|---|---|
| 1 | *M. sp.* strain SK1 FMO | oxygenase | MATRIAILGAGPSGMAQLRAFQSAQEKGAEIPELV CFEKQADWGGQWNYTWRTGLDENGEPVHSSMY RYLWSNGPKECLEFADYTFDEHFGKPIASYPPREV LWDYIKGRVEKAGVRKYIRFNTAVRHVEFNEDSQT FTVTVQDHTTDTIYSEEFDYVVCCTGHFSTPYVPEF EGFEKFGGRILHAHDFRDALEFKDKTVLLVGSSYS AEDIGSQCYKYGAKKLISCYRTAPMGYKWPENWD ERPNLVRVDTENAYFADGSSEKVDAIILCTGYIHHF PFLNDDLRLVTNNRLWPLNLYKGVVWEDNPKFFYI GMQDQWYSFNMFDAQAWYARDVIMGRLPLPSKE EMKADSMAWREKELTLVTAEEMYTYQGDYIQNLID MTDYPSFDIPATNKTFLEWKHHKKENIMTFRDHSY RSLMTGTMAPKHHTPWIDALDDSLEAYLSDKSEIP VAKEA | Choi HS, Kim JK, Cho EH, Kim YC, Kim JI, Kim SW. A novel flavin-containing monooxygenase from Methylophaga sp strain SK1 and its indigo synthesis in *Escherichia coli*. Biochem Biophys Res Commun. 2003 Jul. 11; 306(4): 930-6. |
| 2 | *B. megaterium* CYP102A1 G4 (P450) | oxygenase | MTIKEMPQPKTFGELKNLPLLNTDKPVQALMKIADE LGEIFKFEAPGLVTRFLSSQRLIKEACDESRFDKNL SQALKFVRDFAGDGLATSWTHEKNWKKAHNILLPS FSQQAMKGYHAMMVDIAVQLVQKWERLNADEHIE VPEDMTRLTLDTIGLCGFNYRFNSFYRDQPHPFITS MVRALDEAMNKLQRANPDDPAYDENKRQFQEDIK VMNDLVDKIIADRKASGEQSDDLLTHMLNGKDPET GEPLDDENIRYQIITFLIAGHETTSGLLSFALYFLVKN PHVLQKAAEEAARVLVDPVPSYKQVKQLKYVGMV LNEALRLWPTLPAFSLYAKEDTVLGGEYPLEKGDE LMVLIPQLHRDKTIWGDDVEEFRPERFENPSAIPQH AFKPFGNGQRACIGQQFALHEATLVLGMMLKHFDF EDHTNYELDIKETLTLKPEGFVVKAKSKKIPLGGIPS PSTEQSAKKVRKKAENAHNTPLLVLYGSNMGTAE GTARDLADIAMSKGFAPQVATLDSHAGNLPREGAV LIVTASYNGHPPDNAKQFVDWLDQASADEVKGVR YSVFGCGDKNWATTYQKVPAFIDETLAAKGAENIA | Dietrich JA, Yoshikuni Y, Fisher KJ, Woolard FX, Ockey D, McPhee DJ, Renninger NS, Chang MC, Baker D, Keasling JD. A novel semi-biosynthetic route for artemisinin production using engineered |

TABLE 1-continued

Sequences

| SEQ ID NO:Name | Function | Amino Acid Sequence | Reference/Source |
|---|---|---|---|
| | | DRGEADASDDFEGTYEEWREHMWSDVAAYFNLDI ENSEDNKSTLSLQFVDSAADMPLAKMHGAFSTNV VASKELQQPGSARSTRHLEIELPKEASYQEGDHLG VIPRNYEGIVNRVTARFGLDASQQIRLEAEEEKLAH LPLAKTVSVEELLQYVELQDPVTRTQLRAMAAKTV CPPHKVELEALLEKQAYKEQVLAKRLTMLELLEKYP ACEMKFSEFIALLPSIRPRYYSISSSPRVDEKQASIT VSVVSGEAWSGYGEYKGIASNYLAELQEGDTITCFI STPQSEFTLPKDPETPLIMVGPGTGVAPFRGFVQA RKQLKEQGQSLGEAHLYFGCRSPHEDYLYQEELE NAQSEGIITLHTAFSRMPNQPKTYVQHVMEQDGKK LIELLDQGAHFYICGDGSQMAPAVEATLMKSYADV HQVSEADARLWLQQLEEKGRYAKDVWAG | substrate-promiscuous P450(BM3). ACS Chem Biol. 2009 Apr. 17; 4(4):261-7. doi: 10.1021/cb900006h. |
| 3 *P. tinctorium* UGT isoform 1 | glucosyl-transferase | MESPAAPPTTAPPPHVIIVPSAGMGHLIPLAEFAKR LLPRFTFTFAVPTSGPPSSSQRDFLSSLPASIDTSF LPEVDLSDAPSDAQIETLMSLMVVRSLPSLRDLIAS YSASGRRVAALVVDLFATDAIDVALELGIRPPFIFFPS TAMTLSFFLHLEKLDETVSCEFAELSDPVQIPGCIP VHGKDLIDPVQDRKNDAYKWLLHHSKRYKLAEGVI VNSFEGLEGGPIRELLHPEPGKPRVYPVGPLIQAG SCEKGAAARPECLKWLDQQPRGSVLFVNFGSGGV LSTEQQNELAGVLAHSQQRFLWVVRPPNDGIANA TYFSVDGEIDPLKLLPEGFLEQTAGRGLVLPMWAP QIDVLSHESTGGFLTHCGWNSTLESVFHGVPLITW PLYAEQKMNAVMLTEGLRVGLRPSVGKDGIIRGAEI ARVIGELMEGEEGKRIRSKMQELKRAASAVLSKDG SSTRALEEVAKIWESKV | Example 1 |
| 4 *P. tinctorium* UGT isoform 2 | glucosyl-transferase | MESPAAPPTTAPPPHVIIMPSAGMGHLIPLAEFAKR LLPRFTFTFAVPTSGPPSSSQRDFLSSLPASIDTSF LPEVDLSDAPSDAQIETLMSLMVVRSLPSLRDLIAS YSASGRRVAALVVDLFATDAIDVALELGIRPPFIFFPS TAMTLSFFLHLEKLDETVSCEFAELSDPVQIPGCIP VHGKDLIDPVQDRKNDAYKWLLHHSKRYKLAEGVI VNSFEGLEAGPIRQLLHPEPGKPRVYPVGPLIQAG SCEKGAAARPECLKWLDQQPRGSVLFVNFGSGGV LSTEQQNELAGVLAHSQQRFLWVVRPPNDGIANA TYFSVDGEIDPLKLLPEGFLEQTAGRGLVLPMWAP QIDVLSHESTGGFLTHCGWNSTLESVFHGVPLITW PLYAEQKMNAVMLTEGLRVGLRPSVGKDGIIRGDE IARVIGELMEGEEGKRIRSKMQELKRAASAVLSKD GSSTRALEEVAKIWESKV | Example 2 |
| 5 *N. tabacum* GenBank AHZ0876 1.1 | glucosyl-transferase | MAETAIVTKSENPHIVILPSPGMGHLIPLVEFSKRLIS QHQFSVTLILPTDGPISNSQKSFLNSLPSCMDYHLL PPVNFDDLPLDVKIETRISLTVTRSLSSLREVFKTLV DSKKVVAFVVDLFGTDAFDVAIDFNVSPYIFFPSTA MALSLFLYLPKLDATVSCEYRDLPDPIQIPGCIPIHG KDLLDPVQDRKNEAYRWLLHHSKRYRMAEGVVSN SFKELEGGPIKALQEEEPGKPPVYPVGPLIQMDSG SKVDGSGCLTWLDEQPRGSVLYVSYGSGGTLSHE QLIEVASGLEMSEQRFLWVIRCPNDTVANATYFNV QDSTNPLDFLPKGFLERTKGLGLVVPNWAPQAQIL SHGSTGGFLTHCGWNSTLESVVHGVPLIAWPLYA EQKMNAVMLTEDIKVALRPKANENGLVGRLEIAKV VKGLMEGEEGKGVRTRMRDLKDAAAKVLSQDGSS TKALAELATKLKNKVLIN | Example 3 |
| 6 *A. thaliana* UGT72B1 | glucosyl-transferase | MEESKTPHVAIIPSPGMGHLIPLVEFAKRLVHLHGL TVTFVIAGEGPPSKAQRTVLDSLPSSISSVFLPPVD LTDLSSSTRIESRISLTVTRSNPELRKVFDSFVEGG RLPTALVVDLFGTDAFDVAVEFHVPPYIFYPTTANV LSFFLHLPKLDETVSCEFRELTEPLMLPGCVPVAGK DFLDPAQDRKDDAYKWLLHNTKRYKEAEGILVNTF FELEPNAIKALQEPGLDKPPVYPVGPLVNIGKQEAK QTEESECLKWLDNQPLGSVLYVSFGSGGTLTCEQ LNELALGLADSEQRFLWVIRSPSGIANSSYFDSHS QTDPLTFLPPGFLERTKKRGFVIPFWAPQAQVLAH PSTGGFLTHCGWNSTLESVVSGIPLIAWPLYAEQK MNAVLLSEDIRAALRPRAGDDGLVRREEVARVVKG LMEGEEGKGVRNKMKELKEAACRVLKDDGSTKA LSLVALKWKAHKKELEQNGNH | Example 4 |

TABLE 1-continued

Sequences

| SEQ ID NO: Name | Function | Amino Acid Sequence | Reference/ Source |
|---|---|---|---|
| 7 *A. thaliana* UGT72E2 | glucosyl- transferase | MHITKPHAAMFSSPGMGHVIPVIELGKRLSANNGF HVTVFVLETDAASAQSKFLNSTGVDIVKLPSPDIYG LVDPDDHVVTKIGVIMRAAVPALRSKIAAMHQKPTA LIVDLFGTDALCLAKEFNMLSYVFIPTNARFLGVSIY YPNLDKDIKEEHTVQRNPLAIPGCEPVRFEDTLDAY LVPDEPVYRDFVRHGLAYPKADGILVNTWEEMEPK SLKSLLNPKLLGRVARVPVYPIGPLCRPIQSSETDH PVLDWLNEQPNESVLYISFGSGGCLSAKQLTELAW GLEQSQQRFVWVVRPPVDGSCCSEYVSANGGGT EDNTPEYLPEGFVSRTSDRGFVVPSWAPQAEILSH RAVGGFLTHCGWSSTLESVVGGVPMIAWPLFAEQ NMNAALLSDELGIAVRLDDPKEDISRWKIEALVRKV MTEKEGEAMRRKVKKLRDSAEMSLSIDGGGLAHE SLCRVTKECQRFLERVVDLSRGA | Example 5 |
| 8 *A. thaliana* UGT72E3 | glucosyl- transferase | MHITKPHAAMFSSPGMGHVLPVIELAKRLSANHGF HVTVFVLETDAASVQSKLLNSTGVDIVNLPSPDISG LVDPNAHVVTKIGVIMREAVPTLRSKIVAMHQNPTA LIIDLFGTDALCLAAELNMLTYVFIASNARYLGVSIYY PTLDEVIKEEHTVQRKPLTIPGCEPVRFEDIMDAYL VPDEPVYHDLVRHCLAYPKADGILVNTWEEMEPKS LKSLQDPKLLGRVARVPVYPVGPLCRPIQSSTTDH PVFDWLNKQPNESVLYISFGSGGSLTAQQLTELAW GLEESQQRFIWVVRPPVDGSSCSDYFSAKGGVTK DNTPEYLPEGFVTRTCDRGFMIPSWAPQAEILAHQ AVGGFLTHCGWSSTLESVLCGVPMIAWPLFAEQN MNAALLSDELGISVRVDDPKEAISRSKIEAMVRKVM AEDEGEEMRRKVKKLRDTAEMSLSIHGGGSAHES LCRVTKECQRFLECVGDLGRGA | Example 6 |
| 9 *H. sapiens* SULT1A*1 wild type | sulfotrans- ferase | MELIQDTSRPPLEYVKGVPLIKYFAEALGPLQSFQA RPDDLLISTYPKSGTTWVSQILDMIYQGGDLEKCH RAPIFMRVPFLEFKAPGIPSGMETLKDTPAPRLLKT HLPLALLPQTLLDQKVKVVYVARNAKDVAVSYYHF YHMAKVHPEPGTWDSFLEKFMVGEVSYGSWYQH VQEWWELSRTHPVLYLFYEDMKENPKREIQKILEF VGRSLPEETVDFVVQHTSFKEMKKNPMTNYTTVP QEFMDHSISPFMRKGMAGDWKTTFTVAQNERFDA DYAEKMAGCSLSFRSEL | Banoglu E, King RS. Sulfation of indoxyl by human and rat aryl (phenol) sulfotransferases to form indoxyl sulfate. Eur J Drug Metab Pharmacokine t. 2002 April- June; 27(2): 135- 40. |
| 10 *H. sapiens* SULT1A*1 D249G | sulfotrans- ferase | MELIQDTSRPPLEYVKGVPLIKYFAEALGPLQSFQA RPDDLLISTYPKSGTTWVSQILDMIYQGGDLEKCH RAPIFMRVPFLEFKAPGIPSGMETLKDTPAPRLLKT HLPLALLPQTLLDQKVKVVYVARNAKDVAVSYYHF YHMAKVHPEPGTWDSFLEKFMVGEVSYGSWYQH VQEWWELSRTHPVLYLFYEDMKENPKREIQKILEF VGRSLPEETVDFVVQHTSFKEMKKNPMTNYTTVP QEFMGHSISPFMRKGMAGDWKTTFTVAQNERFDA DYAEKMAGCSLSFRSEL | Berger I, Guttman C, Amar D, Zarivach R, Aharoni A (2011) The Molecular Basis for the Broad Substrate Specificity of Human Sulfotransferase 1A1. PLoS ONE 6(11): e26794.doi: 10.1371/journal. pone.0026794 |
| 11 *H. sapiens* SULT1A*1 enh1 | sulfotrans- ferase | MELIQDTSRPPLEYVKGVPLIKYFAEALGPLQSFQA RPDDLLISTYPKSGTTWVSEILDMIYQGGDVEKCH RAPIFMRVPFLEFKAPGIPSGMETLKDTPSPRLLKT HLPLALLPQSLLDQKVKVVYVARNAKDVAVSYYHF YHMAKVHPEPGTWDSFLEKFMVGEVSYGSWYQH VQEWWELSRTHPVLYLFYEDMKENPKREIQKILEF VGRSLPEETVDLVVQHTSFKEMKKNPMTNYTTIPQ EFMGHSISPFMRKGMAGDWKTTFTVAQNERFDAD YAEKMAGCSLSFRSEL | Berger I, Guttman C, Amar D, Zarivach R, Aharoni A (2011) The Molecular Basis for the Broad |

TABLE 1-continued

Sequences

| SEQ ID NO:Name | Function | Amino Acid Sequence | Reference/ Source |
|---|---|---|---|
| | | | Substrate Specificity of Human Sulfotransferase 1A1. PLoS ONE 6(11): e26794.doi: 10.1371/journal. pone.0026794 |
| 12 *H. sapiens* SULT1A3*1 wild type | sulfotrans- ferase | MELIQDTSRPPLEYVKGVPLIKYFAEALGPLQSFQA RPDDLLINTYPKSGTTWVSQILDMIYQGGDLEKCN RAPIYVRVPFLEVNDPGEPSGLETLKDTPPPRLIKS HLPLALLPQTLLDQKVKVVYVARNPKDVAVSYYHF HRMEKAHPEPGTWDSFLEKFMAGEVSYGSWYQH VQEWWELSRTHPVLYLFYEDMKENPKREIQKILEF VGRSLPEETMDFMVQHTSFKEMKKNPMTNYTTVP QELMDHSISPFMRKGMAGDWKTTFTVAQNERFDA DYAEKMAGCSLSFRSEL | Banoglu E, King RS. Sulfation of indoxyl by human and rat aryl (phenol) sulfotransferases to form indoxyl sulfate. Eur J Drug Metab Pharmacokinet. 2002 April- June; 27(2): 135- 40. |
| 13 *H. sapiens* SULT1A3*1 D249G | sulfotrans- ferase | MELIQDTSRPPLEYVKGVPLIKYFAEALGPLQSFQA RPDDLLINTYPKSGTTWVSQILDMIYQGGDLEKCN RAPIYVRVPFLEVNDPGEPSGLETLKDTPPPRLIKS HLPLALLPQTLLDQKVKVVYVARNPKDVAVSYYHF HRMEKAHPEPGTWDSFLEKFMAGEVSYGSWYQH VQEWWELSRTHPVLYLFYEDMKENPKREIQKILEF VGRSLPEETMDFMVQHTSFKEMKKNPMTNYTTVP QELMGHSISPFMRKGMAGDWKTTFTVAQNERFDA DYAEKMAGCSLSFRSEL | Berger I, Guttman C, Amar D, Zarivach R, Aharoni A (2011) The Molecular Basis for the Broad Substrate Specificity of Human Sulfotransferase 1A1. PLoS ONE 6(11): e26794.doi: 10.1371/journal. pone.0026794 |
| 14 *H. sapiens* SULT1A3*1 enh1 | sulfotrans- ferase | MELIQDTSRPPLEYVKGVPLIKYFAEALGPLQSFQA RPDDLLINTYPKSGTTWVSEILDMIYQGGDVEKCN RAPIYVRVPFLEVNDPGEPSGLETLKDTPPPRLIKS HLPLALLPQSLLDQKVKVVYVARNPKDVAVSYYHF HRMEKAHPEPGTWDSFLEKFMAGEVSYGSWYQH VQEWWELSRTHPVLYLFYEDMKENPKREIQKILEF VGRSLPEETMDLMVQHTSFKEMKKNPMTNYTTIPQ ELMGHSISPFMRKGMAGDWKTTFTVAQNERFDAD YAEKMAGCSLSFRSEL | Berger I, Guttman C, Amar D, Zarivach R, Aharoni A (2011) The Molecular Basis for the Broad Substrate Specificity of Human Sulfotransferase 1A1. PLoS ONE 6(11): e26794.doi: 10.1371/journal. pone.0026794 |
| 15 *I. tinctoria* UGT1 | glucosyl- transferase | NLAVTFIIPTDGPPSKAQKTVLHSLPPAISHTFLPPV NLSDVPKDAKIETIISLTVLRSLPSIRDLFRSLTASAL VVDLFGTDAFDVAKEFNVSPYIFFPSTAMALSFFLH LPHLDQEVHSEYRELAEPVKIPGCVPIHGKDLLDPV QDRKNDAYKWVLHHTKRYREAEGIIENSFLELEPG PIKELLKEEPGKPPVYSVGPLVNVETGRAGNGSEC LKWLDEQPPGSVLFVSFGSGGTLSSAQINELALGL EASEQRFLWVVRSPNDKVANASYFSADSQADPFD FLPKEFVKRTKERGLVVSSWAPQTQVLAHGSTGG FLTHCGWNSILESVVNGVPLIAWPL | Example 15 |

TABLE 1-continued

Sequences

| SEQ ID NO:Name | Function | Amino Acid Sequence | Reference/Source |
|---|---|---|---|
| 16 *I. tinctoria* UGT2 | glucosyl-transferase | ELNILSYLYFPSTAMLLSLCLYSSKLDKEISIEYKDLL EPIKLPGCIPISPSDLPDPLQDRSGESYQQFLEANE RFYLADGILVNSFVEMEGGTIRALQEEESRGIPSVY AIGPFVKMGSCSCDDYEGSEKDNYLTWLDKQEKC SILYVSFGSGGTLFHDQIIELAWGLELSGQKFLWVL RPPSKFGIVADLSAVNLDPLQFLPSGFLERTKGQG LVVPYWATQIEILSHSAIGGYLCHCGWNSILESVVH GVPIIAWPLFAEQKMNAAMLTTGLKVALRPKVSEK GMIEREEIAVVIKNLMVGEEVAKEIRQRMKWLKDAA HDALKEDGSSTRTLTQLAIKWESLAV | Example 15 |
| 17 *I. suffruticosa* UGT1 | glucosyl-transferase | SVTFIIPTDGPPSKAQKTVLQSLPPAISHTFLPPVNL SDVPKDAMIETIISLTVLRSLPSIRDLFRSLSPSVLVL DLFGTDAFDVAKEFNVSPYIFFPSTAMVLSFFLHLP HLDREVHSEYRELAEPVKIPGCVPVHGKDLLAPVQ DRKNDAYKWVLHHTKRYREAEGIIENSFLELEPGPI KELLKEDSVKPPVYPVGPLVNVETGRAGNGSECLK WLDEQPHGSVLFVSFGSGGTLSXAQXNELALGLE ASEZRFLWVVRSPNDXXANASFFSAXSXADPFDFL PKGFVERTKZRGXXXXSWAPQPQVLAHGSTGGFL THCGWNSILESVVNGVPLIAWPLYAEQKMNAVMLT QDXKVALRXXDXBGXLVXREEIAXVVKXLMXGXEG KKVRXXMKDLK | Example 15 |
| 18 *I. suffruticosa* UGT2 | glucosyl-transferase | MAKTVHIAVVPSAGFSHLVPVIEFSKRLIKHHPNFH VTCIIPSLESPPQSSKAYLETLPSNIDSIFLPPIKKED LPQGAYTGILIQLTLTYSLPSIHEALKSLNSKAPLAVL VADVFAYQALDPAKEFNSLSYIYVPGSATVLSLVLH MPRLDEEVSGEFKDHKEPIKLPGCVPLMGYDLPNP VQIRSSEAYKQFLERAKRMFDVDGMLINSFLELEP GAIKALEEKGNERRMRFYPVGPITQKGSSNEVDDD SGCLRWLDNQPVGSVLYVSFGSGGTLSQNQIDEL ASGLELSGQRFLWVLRAPSDSSSGAYLGGASEDP LKFLPSGFLERTKEQGLVVPSWAPQIQVLSHESVS GFLSHCGWNSILESVQMGVPLITWPLFAEQRMNA VMLTNGLKVALRPKVNEDGIVKKEEIAKVIRCLMEG EEGKGMRERMEKLKNSAAIALEDGSSTQSLLQLAS DLENLGGGF | Example 15 |
| 19 *P. trichocarpa* XP_002320190.1 | glucosyl-transferase | MAETDSPPHVAILPSPGMGHLIPLVELAKRLVHQH NLSVTFIIPTDGSPSKAQRSVLGSLPSTIHSVFLPPV NLSDLPEDVKIETLISLTVARSLPSLRDVLSSLVASG TRVVALVVDLFGTDAFDVAREFKASPYIFYPAPAMA LSLFFYLPKLDEMVSCEYSEMQEPVEIPGCLPIHGG ELLDPTRDRKNDAYKWLLHHSKRYRLAEGVMVNS FIDLERGALKALQEVEPGKPPVYPVGPLVNMDSNT SGVEGSECLKWLDDQPLGSVLFVSFGSGGTLSFD QITELALGLEMSEQRFLWVARVPNDKVANATYFSV DNHKDPFDFLPKGFLDRTKGRGLVVPSWAPQAQV LSHGSTGGFLTHCGWNSTLESVVNAVPLIVWPLYA EQKMNAWMLTKDVEVALRPKASENGLIGREEIANI VRGLMEGEEGKRVRNRMKDLKDAAAEVLSEAGSS TKALSEVARKWKNHKCTQDCN | BLASTP similarity to other glucosyltrans-ferases |
| 20 *L. barbarum* BAG80556.1 | glucosyl-transferase | MAETPVVTPHIAILPSPGMGHLIPLVEFSKRLIQNHH FSVTLILPTDGPVSNAQKIYLNSLPCSMDYHLLPPV NFDDLPLDTKMETRISLTVTRSLPSLREVFKTLVET KKTVALVVDLFGTDAFDVANDFKVSPYIFYPSTAMA LSLFLYLPKLDETVSCEYTDLPDPVQIPGCIPIHGKD LLDPVQDRKNEAYKWVLHHSKRYRMAEGIVANSF KELEGGAIKALQEEEPGKPPVYPVGPLIQMDSGSG SKADRSECLTWLDEQPRGSVLYISFGSGGTLSHEQ MIELASGLEMSEQRFLWVIRTPNDKMASATYFNVQ DSTNPLDFLPKGFLEKTKGLGLVVPNWAPQAQILG HGSTSGFLTHCGWNSTLESVVHGVPFIAWPLYAE QKMNAVMLSEDIKVALRPKANENGIVGRLEIAKVVK GLMEGEEGKVVRSRMRDLKDAAAKVLSEDGSSTK ALAELATKLKKKVSNN | BLASTP similarity to other glucosyltrans-ferases |
| 21 *P. putida* ndoA | oxygenase | MTVKWIEAVALSDILEGDVLGVTVEGKELALYEVEG EIYATDNLCTHGSARMSDYLEGREIECPLHQGRF DVCTGKALCAPVTQNIKTYPVKIENLRVMIDLS | Berry, A. et al. Application of metabolic engineering to improve both |

TABLE 1-continued

Sequences

| SEQ ID NO:Name | Function | Amino Acid Sequence | Reference/ Source |
|---|---|---|---|
| | | | the production and use of biotech indigo. Journal of Industrial Microbiology & Biotechnology 28, 127-133 (2002) |
| 22 *P. putida* ndoB | oxygenase | MNYNNKILVSESGLSQKHLIHGDEELFQHELKTIFA RNWLFLTHDSLIPAPGDYVTAKMGIDEVIVSRQND GSIRAFLNVCRHRGKTLVSVEAGNAKGFVCSYHG WGFGSNGELQSVPFEKDLYGESLNKKCLGLKEVA RVESFHGFIYGCFDQEAPPLMDYLGDAAWYLEPM FKHSGGLELVGPPGKVVIKANWKAPAENFVGDAY HVGWTHASSLRSGESIFSSLAGNAALPPEGAGLQ MTSKYGSGMGVLWDGYSGVHSADLVPELMAFGG AKQERLNKEIGDVRARIYRSHLNCTVFPNNSMLTC SGVFKVWNPIDANTTEVWTYAIVEKDMPEDLKRRL ADSVQRTFGPAGFWESDDNDNMETASQNGKKYQ SRDSDLLSNLGFGEDVYGDAVYPGVVGKSAIGETS YRGFYRAYQAHVSSSNWAEFEHASSTWHTELTKT TDR | Berry, A. et al. Application of metabolic engineering to improve both the production and use of biotech indigo. Journal of Industrial Microbiology & Biotechnology 28, 127-133 (2002) |
| 23 *P. putida* ndoC | oxygenase | MMINIQEDKLVSAHDAEEILRFFNCHDSALQQEATT LLTQEAHLLDIQAYRAWLEHCVGSEVQYQVISREL RAASERRYKLNEAMNVYNENFQQLKVRVEHQLDP QNWGNSPKLRFTRFITNVQAAMDVNDKELLHIRSN VILHRARRGNQVDVFYAAREDKWKRGEGGVRKLV QRFVDYPERILQTHNLMVFL | Berry, A. et al. Application of metabolic engineering to improve both the production and use of biotech indigo. Journal of Industrial Microbiology & Biotechnology 28, 127-133 (2002) |
| 24 *P. putida* ndoR | oxygenase | MELLIQPNNRIIPFSAGANLLEVLRENGVAISYSCLS GRCGTCRCRVIDGSVIDSGAENGQSNLTDKQYVLA CQSVLTGNCAIEVPEADEIVTHPARIIKGTVVAVESP THDIRRLRVRLSKPFEFSPGQYATLQFSPEHARPY SMAGLPDDQEMEFHIRKVPGGRVTEYVFEHVREG TSIKLSGPLGTAYLRQKHTGPMLCVGGGTGLAPVL SIVRGALKSGMTNPILLYFGVRSQQDLYDAERLHKL AADHPQLTVHTVIATGPINEGQRAGLITDVIEKDILS LAGWRAYLCGAPAMVEALCTVTKHLGISPEHIYAD AFYPGGI | Berry, A. et al. Application of metabolic engineering to improve both the production and use of biotech indigo. Journal of Industrial Microbiology & Biotechnology 28, 127-133 (2002) |
| 25 *B. circulans* bglA | G- hydrolase | MSIHMFPSDFKWGVATAAYQIEGAYNEDGRGMSI WDTFAHTPGKVKNGDNGNVACDSYHRVEEDVQLL KDLGVKVYRFSISWPRVLPQGTGEVNRAGLDYYH RLVDELLANGIEPFCTLYHWDLPQALQDQGGWGS RITIDAFAEYAELMFKELGGKIKQWITFNEPWCMAF LSNYLGVHAPGNKDLQLAIDVSHHLLVAHGRAVTL FRELGISGEIGIAPNTSWAVPYRRTKEDMEACLRV NGWSGDWYLDPIYFGEYPKFMLDWYENLGYKPPI VDGDMELIHQPIDFIGINYYTSSMNRYNPGEAGGM LSSEAISMGAPKTDIGWEIYAEGLYDLLRYTADKYG NPTLYITENGACYNDGLSLDGRIHDQRRIDYLAMHL IQASRAIEDGINLKGYMEWSLMDNFEWAEGYGMR FGLVHVDYDTLVRTPKDSFYWYKGVISRGWLDL | S Paavilainen, J Hellman, T Korpela. Purification, characterization, gene cloning, and sequencing of a new beta- glucosidase from Bacillus circulans subsp. alkalophilus. Appl. Environ. Microbiol. March 1993 vol. 59 no. 3 927-932 |

TABLE 1-continued

Sequences

| SEQ ID NO: Name | Function | Amino Acid Sequence | Reference/ Source |
|---|---|---|---|
| 26 P. aeruginosa atsA | S-hydrolase | MSKRPNFLVIVADDLGFSDIGAFGGEIATPNLDALAI AGLRLTDFHTASTCSPTRSMLLTGTDHHIAGIGTMA EALTPELEGKPGYEGHLNERVVALPELLREAGYQT LMAGKWHLGLKPEQTPHARGFERSFSLLPGAANH YGFEPPYDESTPRILKGTPALYVEDERYLDTLPEGF YSSDAFGDKLLQYLKERDQSRPFFAYLPFSAPHWP LQAPREIVEKYRGRYDAGPEALRQERLARLKELGL VEADVEAHPVLALTREWEALEDEERAKSARAMEV YAAMVERMDWNIGRVVDYLRRQGELDNTFVLFMS DNGAEGALLEAFPKFGPDLLGFLDRHYDNSLENIG RANSYVWYGPRWAQAATAPSRLYKAFTTQGGIRV PALVRYPRLSRQGAISHAFATVMDVTPTLLDLAGV RHPGKRWRGREIAEPRGRSWLGWLSGETEAAHD ENTVTGWELFGMRAIRQGDWKAVYLPAPVGPATW QLYDLARDPGEIHDLADSQPGKLAELIEHWKRYVS ETGVVEGASPFLVR | Beil S, Kehrli H, James P, Staudenmann W, Cook AM, Leisinger T, Kertesz MA. Purification and characterization of the arylsulfatase synthesized by *Pseudomonas aeruginosa* PAO during growth in sulfate-free medium and cloning of the arylsulfatase gene (atsA). Eur J Biochem. 1995 Apr. 15; 229(2): 385-94. |
| 27 E. coli yidJ | S-hydrolase | MKRPNFLFVMTDTQATNMVGCYSGKPLNTQNIDSL AAEGIRFNSAYTCSPVCTPARAGLFTGIYANQSGP WTNNVAPGKNISTMGRYFKDAGYHTCYIGKWHLD GHDYFGTGECPPEWDADYWFDGANYLSELTEKEI SLWRNGLNSVEDLQANHIDETFTWAHRISNRAVDF LQQPARADEPFLMVVSYDEPHHPFTCPVEYLEKYA DFYYELGEKAQDDLANKPEHHRLWAQAMPSPVGD DGLYHHPLYFACNDFVDDQIGRVINALTPEQRENT WVIYTSDHGEMMGAHKLISKGAAMYDDITRIPLIIRS PQGERRQVDTPVSHIDLLPTMMALADIEKPEILPGE NILAVKEPRGVMVEFNRYEIEHDSFGGFIPVRCWV TDDFKLVLNLFTSDELYDRRNDPNEMHNLIDDIRFA DVRSKMHDALLDYMDKIRDPFRSYQWSLRPWRKD ARPRWMGAFRPRPQDGYSPVVRDYDTGLPTQGV KVEEKKQKF | BLASTP similarity to other S-hydrolases |
| 28 P. stuartii arylsulfatase 3 | S-hydrolase | MKKTLLAIALSSVMSGVALGEVDDRPNVLIIIADDM GYSDISPFGGEIPTPNLQKMAEQGVRMSQYYTSP MSAPARSMLMTGATNQQAGMGGMWYENTVGK PGYELRLTDRVVTMAERFQDAGYNTLMSGKWHLG YTKGARPTDRGFNQAFAFMGGGTSHFDDAKPLGT VESFHTYYTLNGEKVSLPSDFYSSKNYAQQLEQWI KQTPSDQPIFAYLAFTAPHDPIQAPDDWIRKFDGKY DEGFGKIYRQRINRLKELGIINDKTPMPKLNLDKEW EQLTPEEKRYAAKTMQVYAAMIAYMDDQIGGVINT LKETGRDKNTIIIFATDNGANPASGFYYESDPEYWK QFDNSYENLGRKNSFVSVGPQWANVSNAPYANY HKTTSAQGGINTDLIITGPGIGKAGSIDKTPMAVYDI APTLYEFAGIDANKQIKNIHPLPMLGTSFKSHFLGK STVNPRQLFGVELHNQAALVEGDWKLRRLVKASP KAEMAPWQLFNLKEDPLETRDLAAKHPEIVQKLQK KYEQFAKTGMIIEAKGEAIDYIGVDESTGNYIGIDPK TNKRIEPAKVK | Dealler SF, Hawkey PM, Millar MR. Enzymatic degradation of urinary indoxyl sulfate by Providencia stuartii and *Klebsiella pneumoniae* causes the purple urine bag syndrome. J Clin Microbiol. 1988 October; 26(10): 2152-6. |
| 29 P. stuartii anaerobic sulfatase maturating enzyme (anSME) | S-hydrolase companion | MKISFYDPPRLQGKSLKSAIPHILLKPVGSGCNLK CDYCYYPQHNEQKAAPMLKAMLEPFIKNYIAAQPA YTKEINFVWQGGEPLLAGLDFYKRAIALQQKYAPH GVRIINTLQTNATLLTPSWCRFLKQHDFVIGVSLDG PESIHDQYRHDRRGNSGSYASVIKGIALLQQFDIEF NILTVVHDGVAHLGKEIYLHFVQLGIRYIQFQPLMLE GDAIHQGFTLSANNWGLFLSSVYQQWQASGHIGR VFVMNIEQVYSQYFTQVSSTCVHSERCGTNMMME TQGEIYACDHQANQSHYLGQFNGQQGFSDFVEAS ISLPFGQNKSRRKECQQCSVKMVCQGGCPAHLNQ | Dealler SF, Hawkey PM, Millar MR. Enzymatic degradation of urinary indoxyl sulfate by Providencia stuartii and *Klebsiella* |

TABLE 1-continued

Sequences

| SEQ ID NO: Name | Function | Amino Acid Sequence | Reference/ Source |
|---|---|---|---|
| | | FGRNQLCEGYFAFFSLVLAPIRQYQRNAQGVQHW RNAFLKNAVA | pneumoniae causes the purple urine bag syndrome. J Olin Microbiol. 1988 October; 26(10): 2152-6. |
| 30 N. crassa CDT1 | transporter | MSSHGSHDGASTEKHLATHDIAPTHDAIKIVPKGH GQTATKPGAQEKEVRNAALFAAIKESNIKPWSKESI HLYFAIFVAFCCACANGYDGSLMTGIIAMDKFQNQF HTGDTGPKVSVIFSLYTVGAMVGAPFAAILSDRFG RKKGMFIGGIFIIVGSIIVASSSKLAQFVVGRFVLGLG IAIMTVAAPAYSIEIAPPHWRGRCTGFYNCGWFGG SIPAACITYGCYFIKSNWSWRIPLILQAFTCLIVMSS VFFLPESPRFLFANGRDAEAVAFLVKYHGNGDPNS KLVLLETEEMRDGIRTDGVDKVWWDYRPLFMTHS GRWRMAQVLMISIFGQFSGNGLGYFNTVIFKNIGVT STSQQLAYNILNSVISAIGALTAVSMTDRMPRRAVLI IGTFMCAAALATNSGLSATLDKQTQRGTQINLNQG MNEQDAKDNAYLHVDSNYAKGALAAYFLFNVIFSF TYTPLQGVIPTEALETTIRGKGLALSGFIVNAMGFIN QFAGPIALHNIGYKYIFVFVGWDLIETVAWYFFGVE SQGRTLEQLEWVYDQPNPVKASLKVEKVVVQADG HVSEAIVA | Kim H, Lee WH, Galazka JM, Cate JH, Jin YS. Analysis of cellodextrin transporters from Neurospora crassa in Saccharomyces cerevisiae for cellobiose fermentation. Appl Microbiol Biotechnol. 2014 February; 98(3): 1087-94. doi: 10.1007/s002 53-013-5339- 2. Epub 2013 Nov. 5. |

What is claimed is:

1. A method for dyeing a textile article, the method comprising:
   a) producing a compound of Formula (A), the method comprising:
   culturing a host cell in vitro in a growth medium, wherein the host cell is genetically modified with heterologous nucleic acids comprising nucleotide sequences encoding:
   i) a heterologous oxygenase polypeptide comprising an amino acid sequence having at least 90% amino acid sequence identity to any one of SEQ ID NOs: 1 and 21-24; and
   ii) a heterologous glucosyltransferase polypeptide comprising an amino acid sequence having at least 90% amino acid sequence identity to any one of SEQ ID NOs:3-8, wherein the compound of Formula (A) is:

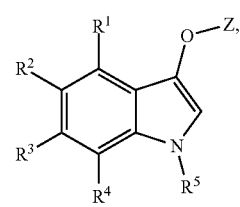

wherein:
$R^1$, $R^2$, $R^3$, and $R^4$ are independently selected from the group consisting of H, halo, nitro, sulfate, phosphate, hydroxyl, —C(O)OR$^b$, —R$^2$C(O)OR$^b$, —R$^a$OC(O)R$^b$, —OR$^a$, —NR$^b$R$^c$, and alkyl;
wherein alkyl is unsubstituted or substituted with one or more substituents independently selected from the group consisting of halo, nitro, sulfate, phosphate, hydroxyl, —C(O)OR$^b$, —R$^a$C(O)OR$^b$, —R$^a$OC(O)R$^b$, —OR$^a$, —NR$^b$R$^c$, and —R$^a$OR$^d$;

R$^5$ is H or alkyl, wherein alkyl is unsubstituted or substituted with one or more substituents independently selected from the group consisting of halo, hydroxyl, =O, —C(O)OR$^b$, —R$^a$C(O)OR$^b$, —R$^a$OC(O)R$^b$, —OR$^a$, and —NR$^b$R$^c$;

R$^a$ and R$^d$ are independently alkyl;
R$^b$ and R$^c$ are independently H or alkyl;
Z is a glycone;
b) converting the isolated compound of Formula (A) to a compound of Formula (II),
wherein the compound of Formula (II) is:

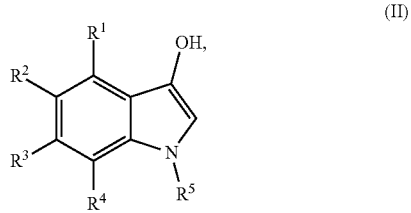

(II)

wherein R$^1$, R$^2$, R$^3$, R$^4$, and R$^5$ are defined as for Formula (A); and
c) applying the compound of Formula (II) to the textile article, thereby dyeing the textile article;
wherein the heterologous oxygenase polypeptide and the heterologous glucosyltransferase polypeptide are encoded by multiple heterologous nucleic acids, or wherein the heterologous oxygenase polypeptide and the heterologous glucosyltransferase polypeptide are encoded by a single heterologous nucleic acid.

2. The method of claim 1, wherein the host cell is a bacterial cell.

3. The method of claim 2, wherein the host cell is *Escherichia coli* or *Corynebacterium glutamicum*.

4. The method of claim 1, wherein the host cell is a eukaryotic cell.

5. The method of claim 4, wherein the host cell is a yeast cell.

6. The method of claim 5, wherein the host cell is selected from the group consisting of *Saccharomyces cerevisiae, Pichia pastoris, Kluyveromyces lactis, Kluyveromyces marxianus*, and *Schizosaccharomyces pombe*.

7. The method of claim 1, wherein the heterologous glucosyltransferase polypeptide comprises an amino acid sequence having at least 95% amino acid sequence identity to the amino acid sequence set forth in SEQ ID NO:4.

8. The method of claim 1, wherein the heterologous glucosyltransferase polypeptide comprises an amino acid sequence having at least 95% amino acid sequence identity to the amino acid sequence set forth in SEQ ID NO:5.

9. The method of claim 1, wherein the heterologous glucosyltransferase polypeptide comprises an amino acid sequence having at least 95% amino acid sequence identity to the amino acid sequence set forth in SEQ ID NO:6.

10. The method of claim 1, wherein the heterologous glucosyltransferase polypeptide comprises an amino acid sequence having at least 95% amino acid sequence identity to the amino acid sequence set forth in SEQ ID NO:7.

11. The method of claim 1, wherein the heterologous glucosyltransferase polypeptide comprises an amino acid sequence having at least 95% amino acid sequence identity to the amino acid sequence set forth in SEQ ID NO:8.

12. The method of claim 1, wherein the heterologous oxygenase polypeptide comprises an amino acid sequence having at least 95% amino acid sequence identity to the amino acid sequence set forth in SEQ ID NO:21.

13. The method of claim 1, wherein the heterologous glucosyltransferase polypeptide comprises an amino acid sequence having at least 98% amino acid sequence identity to the amino acid sequence set forth in any one of SEQ ID NOs:4-8.

14. The method of claim 1, wherein the heterologous oxygenase polypeptide comprises an amino acid sequence having at least 95% amino acid sequence identity to the amino acid sequence set forth in SEQ ID NO:22.

15. The method of claim 1, wherein the heterologous oxygenase polypeptide comprises an amino acid sequence having at least 95% amino acid sequence identity to the amino acid sequence set forth in SEQ ID NO:23.

16. The method of claim 1, wherein the heterologous oxygenase polypeptide comprises an amino acid sequence having at least 95% amino acid sequence identity to the amino acid sequence set forth in SEQ ID NO:24.

17. The method of claim 1, wherein the heterologous oxygenase polypeptide comprises an amino acid sequence having at least 98% amino acid sequence identity to the amino acid sequence set forth in any one of SEQ ID NOs:21-24.

18. The method of claim 1, wherein said converting comprises contacting the compound of Formula (A) with a glucosidase.

19. The method of claim 1, wherein the textile article is a fabric.

20. The method of claim 19, wherein the fabric is a component of jeans.

21. A method for dyeing a textile article, the method comprising:
a) producing a compound of Formula (A), the method comprising:
culturing a host cell in vitro in a growth medium, wherein the host cell is genetically modified with one or more heterologous nucleic acids comprising nucleotide sequences encoding:
i) a heterologous oxygenase polypeptide comprising an amino acid sequence having at least 90% amino acid sequence identity to any one of SEQ ID NOs: 1 and 21-24; and
ii) a heterologous glucosyltransferase polypeptide comprising an amino acid sequence having at least 90% amino acid sequence identity to any one of SEQ ID NOs:3-8, wherein the compound of Formula (A) is:

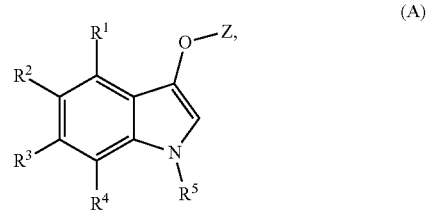

(A)

wherein:
R$^1$, R$^2$, R$^3$, and R$^4$ are independently selected from the group consisting of H, halo, nitro, sulfate, phosphate, hydroxyl, —C(O)OR$^b$, —R$^2$C(O)OR$^b$, —$R^aOC(O)R^b$, —$OR^a$, —$NR^bR^c$, and alkyl;
wherein alkyl is unsubstituted or substituted with one or more substituents independently selected from the group consisting of halo, nitro, sulfate, phosphate, hydroxyl, —$C(O)OR^b$, —$R^aC(O)OR^b$, —$R^aOC(O)R^b$, —$OR^a$, —$NR^bR^c$, and —$R^aOR^d$;

$R^5$ is H or alkyl, wherein alkyl is unsubstituted or substituted with one or more substituents independently selected from the group consisting of halo, hydroxyl, =O, —$C(O)OR^b$, —$R^aC(O)OR^b$, —$R^aOC(O)R^b$, —$OR^a$, and —$NR^bR^c$;

$R^a$ and $R^d$ are independently alkyl;
$R^b$ and $R^c$ are independently H or alkyl;
Z is a glycone;

b) converting the isolated compound of Formula (A) to a compound of Formula (II),
wherein the compound of Formula (II) is:

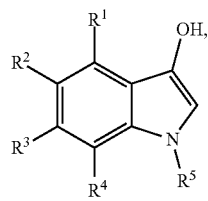

(II)

wherein $R^1$, $R^2$, $R^3$, $R^4$, and $R^5$ are defined as for Formula (A);

c) applying the compound of Formula (II) to the textile article; and
d) converting the compound of Formula (II) to a compound of Formula (B), thereby dyeing the textile article, wherein the compound of Formula (B) is

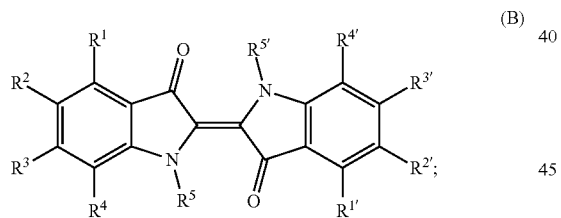

(B)

wherein $R^1$, $R^2$, $R^3$, $R^4$, and $R^5$ are defined as for Formula (A), and
$R^{1'}$, $R^{2'}$, $R^{3'}$, $R^{4'}$, and $R^{5'}$ are $R^1$, $R^2$, $R^3$, $R^4$, and $R^5$, respectively as defined in Formula (A).

22. The method of claim 21, wherein said converting of step d) comprises contacting the compound of Formula (II) with oxygen.

23. A method for dyeing a textile article, the method comprising:
a) producing a compound of Formula (A), the method comprising:
culturing a host cell in vitro in a growth medium,
wherein the host cell is genetically modified with one or more heterologous nucleic acids comprising nucleotide sequences encoding:
i) a heterologous oxygenase polypeptide comprising an amino acid sequence having at least 90% amino acid sequence identity to any one of SEQ ID NOs: 1 and 21-24; and
ii) a heterologous glucosyltransferase polypeptide comprising an amino acid sequence having at least 90% amino acid sequence identity to any one of SEQ ID NOs:3-8,
wherein the compound of Formula (A) is:

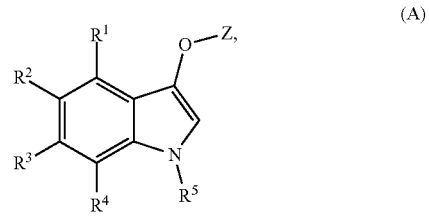

(A)

wherein:
$R^1$, $R^2$, $R^3$, and $R^4$ are independently selected from the group consisting of H, halo, nitro, sulfate, phosphate, hydroxyl, —$C(O)OR^b$, —$R^2C(O)OR^b$, —$R^aOC(O)R^b$, —$OR^a$, —$NR^bR^c$, and alkyl;
wherein alkyl is unsubstituted or substituted with one or more substituents independently selected from the group consisting of halo, nitro, sulfate, phosphate, hydroxyl, —$C(O)OR^b$, —$R^aC(O)OR^b$, —$R^aOC(O)R^b$, —$OR^a$, —$NR^bR^c$, and —$R^aOR^d$;

$R^5$ is H or alkyl, wherein alkyl is unsubstituted or substituted with one or more substituents independently selected from the group consisting of halo, hydroxyl, =O, —$C(O)OR^b$, —$R^aC(O)OR^b$, —$R^aOC(O)R^b$, —$OR^a$, and —$NR^bR^c$;

$R^a$ and $R^d$ are independently alkyl;
$R^b$ and $R^c$ are independently H or alkyl;
Z is a glycone;

b) converting the isolated compound of Formula (A) to a compound of Formula (II), wherein the compound of Formula (II) is:

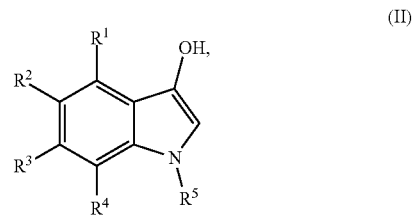

(II)

wherein $R^1$, $R^2$, $R^3$, $R^4$, and $R^5$ are defined as for Formula (A);

c) converting the compound of Formula (II) to a compound of Formula (B),
wherein the compound of Formula (B) is

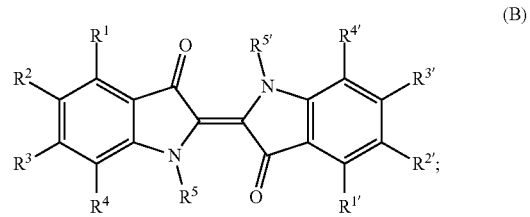

(B)

wherein $R^1$, $R^2$, $R^3$, $R^4$, and $R^5$ are defined as for Formula (A), and $R^{1'}$, $R^{2'}$, $R^{3'}$, $R^{4'}$, and $R^{5'}$ are $R^1$, $R^2$, $R^3$, $R^4$, and $R^5$, respectively as defined in Formula (A), d) reducing the compound of Formula (B) to provide a reduced intermediate of the compound of Formula (B), e) applying the reduced intermediate to the textile article, and f) oxidizing the reduced intermediate to a compound of Formula (B), thereby dying the textile article.

* * * * *

SEQUENCE LISTING

<160> NUMBER OF SEQ ID NOS: 30

<210> SEQ ID NO 1
<211> LENGTH: 456
<212> TYPE: PRT
<213> ORGANISM: Unknown
<220> FEATURE:
<223> OTHER INFORMATION: Methylophaga sp. strain SK1

<400> SEQUENCE: 1

```
Met Ala Thr Arg Ile Ala Ile Leu Gly Ala Gly Pro Ser Gly Met Ala
1               5                   10                  15

Gln Leu Arg Ala Phe Gln Ser Ala Gln Glu Lys Gly Ala Glu Ile Pro
            20                  25                  30

Glu Leu Val Cys Phe Glu Lys Gln Ala Asp Trp Gly Gly Gln Trp Asn
        35                  40                  45

Tyr Thr Trp Arg Thr Gly Leu Asp Glu Asn Gly Glu Pro Val His Ser
    50                  55                  60

Ser Met Tyr Arg Tyr Leu Trp Ser Asn Gly Pro Lys Glu Cys Leu Glu
65                  70                  75                  80

Phe Ala Asp Tyr Thr Phe Asp Glu His Phe Gly Lys Pro Ile Ala Ser
                85                  90                  95

Tyr Pro Pro Arg Glu Val Leu Trp Asp Tyr Ile Lys Gly Arg Val Glu
            100                 105                 110

Lys Ala Gly Val Arg Lys Tyr Ile Arg Phe Asn Thr Ala Val Arg His
        115                 120                 125
```

Val Glu Phe Asn Glu Asp Ser Gln Thr Phe Thr Val Thr Val Gln Asp
    130                 135                 140

His Thr Thr Asp Thr Ile Tyr Ser Glu Glu Phe Asp Tyr Val Val Cys
145                 150                 155                 160

Cys Thr Gly His Phe Ser Thr Pro Tyr Val Pro Glu Phe Glu Gly Phe
                165                 170                 175

Glu Lys Phe Gly Gly Arg Ile Leu His Ala His Asp Phe Arg Asp Ala
            180                 185                 190

Leu Glu Phe Lys Asp Lys Thr Val Leu Leu Val Gly Ser Ser Tyr Ser
        195                 200                 205

Ala Glu Asp Ile Gly Ser Gln Cys Tyr Lys Tyr Gly Ala Lys Lys Leu
    210                 215                 220

Ile Ser Cys Tyr Arg Thr Ala Pro Met Gly Tyr Lys Trp Pro Glu Asn
225                 230                 235                 240

Trp Asp Glu Arg Pro Asn Leu Val Arg Val Asp Thr Glu Asn Ala Tyr
                245                 250                 255

Phe Ala Asp Gly Ser Ser Glu Lys Val Asp Ala Ile Ile Leu Cys Thr
            260                 265                 270

Gly Tyr Ile His His Phe Pro Phe Leu Asn Asp Asp Leu Arg Leu Val
        275                 280                 285

Thr Asn Asn Arg Leu Trp Pro Leu Asn Leu Tyr Lys Gly Val Val Trp
    290                 295                 300

Glu Asp Asn Pro Lys Phe Phe Tyr Ile Gly Met Gln Asp Gln Trp Tyr
305                 310                 315                 320

Ser Phe Asn Met Phe Asp Ala Gln Ala Trp Tyr Ala Arg Asp Val Ile
                325                 330                 335

Met Gly Arg Leu Pro Leu Pro Ser Lys Glu Glu Met Lys Ala Asp Ser
            340                 345                 350

Met Ala Trp Arg Glu Lys Glu Leu Thr Leu Val Thr Ala Glu Glu Met
        355                 360                 365

Tyr Thr Tyr Gln Gly Asp Tyr Ile Gln Asn Leu Ile Asp Met Thr Asp
    370                 375                 380

Tyr Pro Ser Phe Asp Ile Pro Ala Thr Asn Lys Thr Phe Leu Glu Trp
385                 390                 395                 400

Lys His His Lys Lys Glu Asn Ile Met Thr Phe Arg Asp His Ser Tyr
                405                 410                 415

Arg Ser Leu Met Thr Gly Thr Met Ala Pro Lys His His Thr Pro Trp
            420                 425                 430

Ile Asp Ala Leu Asp Asp Ser Leu Glu Ala Tyr Leu Ser Asp Lys Ser
        435                 440                 445

Glu Ile Pro Val Ala Lys Glu Ala
    450                 455

<210> SEQ ID NO 2
<211> LENGTH: 1049
<212> TYPE: PRT
<213> ORGANISM: Bacillus megaterium

<400> SEQUENCE: 2

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu

```
                35                  40                  45
Val Thr Arg Phe Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Ala Thr Ser Trp Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
                115                 120                 125

Gln Lys Trp Glu Arg Leu Asn Ala Asp Glu His Ile Glu Val Pro Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
                195                 200                 205

Asp Ile Lys Val Met Asn Asp Leu Val Asp Lys Ile Ile Ala Asp Arg
                210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Leu Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
                370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
450                 455                 460
```

```
Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                    485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
            850                 855                 860

Ala Ser Asn Tyr Leu Ala Glu Leu Gln Glu Gly Asp Thr Ile Thr Cys
865                 870                 875                 880
```

-continued

```
Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 3
<211> LENGTH: 477
<212> TYPE: PRT
<213> ORGANISM: Persicaria tinctoria

<400> SEQUENCE: 3

Met Glu Ser Pro Ala Ala Pro Pro Thr Thr Ala Pro Pro His Val
1               5                   10                  15

Ile Ile Val Pro Ser Ala Gly Met Gly His Leu Ile Pro Leu Ala Glu
            20                  25                  30

Phe Ala Lys Arg Leu Leu Pro Arg Phe Thr Phe Thr Phe Ala Val Pro
        35                  40                  45

Thr Ser Gly Pro Pro Ser Ser Ser Gln Arg Asp Phe Leu Ser Ser Leu
    50                  55                  60

Pro Ala Ser Ile Asp Thr Ser Phe Leu Pro Glu Val Asp Leu Ser Asp
65                  70                  75                  80

Ala Pro Ser Asp Ala Gln Ile Glu Thr Leu Met Ser Leu Met Val Val
                85                  90                  95

Arg Ser Leu Pro Ser Leu Arg Asp Leu Ile Ala Ser Tyr Ser Ala Ser
            100                 105                 110

Gly Arg Arg Val Ala Ala Leu Val Val Asp Leu Phe Ala Thr Asp Ala
        115                 120                 125

Ile Asp Val Ala Leu Glu Leu Gly Ile Arg Pro Phe Ile Phe Phe Pro
    130                 135                 140

Ser Thr Ala Met Thr Leu Ser Phe Phe Leu His Leu Glu Lys Leu Asp
145                 150                 155                 160

Glu Thr Val Ser Cys Glu Phe Ala Glu Leu Ser Asp Pro Val Gln Ile
                165                 170                 175

Pro Gly Cys Ile Pro Val His Gly Lys Asp Leu Ile Asp Pro Val Gln
            180                 185                 190

Asp Arg Lys Asn Asp Ala Tyr Lys Trp Leu Leu His His Ser Lys Arg
        195                 200                 205
```

Tyr Lys Leu Ala Glu Gly Val Ile Val Asn Ser Phe Glu Gly Leu Glu
210                 215                 220

Gly Gly Pro Ile Arg Glu Leu Leu His Pro Glu Pro Gly Lys Pro Arg
225                 230                 235                 240

Val Tyr Pro Val Gly Pro Leu Ile Gln Ala Gly Ser Cys Glu Lys Gly
                245                 250                 255

Ala Ala Ala Arg Pro Glu Cys Leu Lys Trp Leu Asp Gln Gln Pro Arg
            260                 265                 270

Gly Ser Val Leu Phe Val Asn Phe Gly Ser Gly Val Leu Ser Thr
        275                 280                 285

Glu Gln Gln Asn Glu Leu Ala Gly Val Leu Ala His Ser Gln Gln Arg
290                 295                 300

Phe Leu Trp Val Val Arg Pro Pro Asn Asp Gly Ile Ala Asn Ala Thr
305                 310                 315                 320

Tyr Phe Ser Val Asp Gly Glu Ile Asp Pro Leu Lys Leu Leu Pro Glu
                325                 330                 335

Gly Phe Leu Glu Gln Thr Ala Gly Arg Gly Leu Val Leu Pro Met Trp
            340                 345                 350

Ala Pro Gln Ile Asp Val Leu Ser His Glu Ser Thr Gly Gly Phe Leu
        355                 360                 365

Thr His Cys Gly Trp Asn Ser Thr Leu Glu Ser Val Phe His Gly Val
370                 375                 380

Pro Leu Ile Thr Trp Pro Leu Tyr Ala Glu Gln Lys Met Asn Ala Val
385                 390                 395                 400

Met Leu Thr Glu Gly Leu Arg Val Gly Leu Arg Pro Ser Val Gly Lys
                405                 410                 415

Asp Gly Ile Ile Arg Gly Ala Glu Ile Ala Arg Val Ile Gly Glu Leu
            420                 425                 430

Met Glu Gly Glu Glu Gly Lys Arg Ile Arg Ser Lys Met Gln Glu Leu
        435                 440                 445

Lys Arg Ala Ala Ser Ala Val Leu Ser Lys Asp Gly Ser Ser Thr Arg
450                 455                 460

Ala Leu Glu Glu Val Ala Lys Ile Trp Glu Ser Lys Val
465                 470                 475

<210> SEQ ID NO 4
<211> LENGTH: 477
<212> TYPE: PRT
<213> ORGANISM: Persicaria tinctoria

<400> SEQUENCE: 4

Met Glu Ser Pro Ala Ala Pro Pro Thr Thr Ala Pro Pro His Val
1               5                   10                  15

Ile Ile Met Pro Ser Ala Gly Met Gly His Leu Ile Pro Leu Ala Glu
            20                  25                  30

Phe Ala Lys Arg Leu Leu Pro Arg Phe Thr Phe Thr Phe Ala Val Pro
        35                  40                  45

Thr Ser Gly Pro Pro Ser Ser Ser Gln Arg Asp Phe Leu Ser Ser Leu
50                  55                  60

Pro Ala Ser Ile Asp Thr Ser Phe Leu Pro Glu Val Asp Leu Ser Asp
65                  70                  75                  80

Ala Pro Ser Asp Ala Gln Ile Glu Thr Leu Met Ser Leu Met Val Val
                85                  90                  95

Arg Ser Leu Pro Ser Leu Arg Asp Leu Ile Ala Ser Tyr Ser Ala Ser

```
            100                 105                 110
Gly Arg Arg Val Ala Leu Val Asp Leu Phe Ala Thr Asp Ala
            115                 120                 125
Ile Asp Val Ala Leu Glu Leu Gly Ile Arg Pro Phe Ile Phe Pro
    130                 135                 140
Ser Thr Ala Met Thr Leu Ser Phe Phe Leu His Leu Glu Lys Leu Asp
145                 150                 155                 160
Glu Thr Val Ser Cys Glu Phe Ala Glu Leu Ser Asp Pro Val Gln Ile
                165                 170                 175
Pro Gly Cys Ile Pro Val His Gly Lys Asp Leu Ile Asp Pro Val Gln
            180                 185                 190
Asp Arg Lys Asn Asp Ala Tyr Lys Trp Leu Leu His His Ser Lys Arg
            195                 200                 205
Tyr Lys Leu Ala Glu Gly Val Ile Val Asn Ser Phe Glu Gly Leu Glu
            210                 215                 220
Ala Gly Pro Ile Arg Gln Leu Leu His Pro Glu Pro Gly Lys Pro Arg
225                 230                 235                 240
Val Tyr Pro Val Gly Pro Leu Ile Gln Ala Gly Ser Cys Glu Lys Gly
                245                 250                 255
Ala Ala Ala Arg Pro Glu Cys Leu Lys Trp Leu Asp Gln Gln Pro Arg
                260                 265                 270
Gly Ser Val Leu Phe Val Asn Phe Gly Ser Gly Gly Val Leu Ser Thr
            275                 280                 285
Glu Gln Gln Asn Glu Leu Ala Gly Val Leu Ala His Ser Gln Gln Arg
            290                 295                 300
Phe Leu Trp Val Val Arg Pro Pro Asn Asp Gly Ile Ala Asn Ala Thr
305                 310                 315                 320
Tyr Phe Ser Val Asp Gly Glu Ile Asp Pro Leu Lys Leu Leu Pro Glu
                325                 330                 335
Gly Phe Leu Glu Gln Thr Ala Gly Arg Gly Leu Val Leu Pro Met Trp
            340                 345                 350
Ala Pro Gln Ile Asp Val Leu Ser His Glu Ser Thr Gly Gly Phe Leu
            355                 360                 365
Thr His Cys Gly Trp Asn Ser Thr Leu Glu Ser Val Phe His Gly Val
    370                 375                 380
Pro Leu Ile Thr Trp Pro Leu Tyr Ala Glu Gln Lys Met Asn Ala Val
385                 390                 395                 400
Met Leu Thr Glu Gly Leu Arg Val Gly Leu Arg Pro Ser Val Gly Lys
                405                 410                 415
Asp Gly Ile Ile Arg Gly Asp Glu Ile Ala Arg Val Ile Gly Glu Leu
                420                 425                 430
Met Glu Gly Glu Gly Lys Arg Ile Arg Ser Lys Met Gln Glu Leu
            435                 440                 445
Lys Arg Ala Ala Ser Ala Val Leu Ser Lys Asp Gly Ser Ser Thr Arg
            450                 455                 460
Ala Leu Glu Glu Val Ala Lys Ile Trp Glu Ser Lys Val
465                 470                 475

<210> SEQ ID NO 5
<211> LENGTH: 478
<212> TYPE: PRT
<213> ORGANISM: Nicotiana tabacum

<400> SEQUENCE: 5
```

```
Met Ala Glu Thr Ala Ile Val Thr Lys Ser Glu Asn Pro His Ile Val
1               5                   10                  15

Ile Leu Pro Ser Pro Gly Met Gly His Leu Ile Pro Leu Val Glu Phe
            20                  25                  30

Ser Lys Arg Leu Ile Ser Gln His Gln Phe Ser Val Thr Leu Ile Leu
        35                  40                  45

Pro Thr Asp Gly Pro Ile Ser Asn Ser Gln Lys Ser Phe Leu Asn Ser
    50                  55                  60

Leu Pro Ser Cys Met Asp Tyr His Leu Leu Pro Val Asn Phe Asp
65                  70                  75                  80

Asp Leu Pro Leu Asp Val Lys Ile Glu Thr Arg Ile Ser Leu Thr Val
                85                  90                  95

Thr Arg Ser Leu Ser Ser Leu Arg Glu Val Phe Lys Thr Leu Val Asp
            100                 105                 110

Ser Lys Lys Val Val Ala Phe Val Val Asp Leu Phe Gly Thr Asp Ala
        115                 120                 125

Phe Asp Val Ala Ile Asp Phe Asn Val Ser Pro Tyr Ile Phe Phe Pro
    130                 135                 140

Ser Thr Ala Met Ala Leu Ser Leu Phe Leu Tyr Leu Pro Lys Leu Asp
145                 150                 155                 160

Ala Thr Val Ser Cys Glu Tyr Arg Asp Leu Pro Asp Pro Ile Gln Ile
                165                 170                 175

Pro Gly Cys Ile Pro Ile His Gly Lys Asp Leu Leu Asp Pro Val Gln
            180                 185                 190

Asp Arg Lys Asn Glu Ala Tyr Arg Trp Leu Leu His His Ser Lys Arg
        195                 200                 205

Tyr Arg Met Ala Glu Gly Val Val Ser Asn Ser Phe Lys Glu Leu Glu
    210                 215                 220

Gly Gly Pro Ile Lys Ala Leu Gln Glu Glu Pro Gly Lys Pro Pro
225                 230                 235                 240

Val Tyr Pro Val Gly Pro Leu Ile Gln Met Asp Ser Gly Ser Lys Val
                245                 250                 255

Asp Gly Ser Gly Cys Leu Thr Trp Leu Asp Glu Gln Pro Arg Gly Ser
            260                 265                 270

Val Leu Tyr Val Ser Tyr Gly Ser Gly Gly Thr Leu Ser His Glu Gln
        275                 280                 285

Leu Ile Glu Val Ala Ser Gly Leu Glu Met Ser Glu Gln Arg Phe Leu
    290                 295                 300

Trp Val Ile Arg Cys Pro Asn Asp Thr Val Ala Asn Ala Thr Tyr Phe
305                 310                 315                 320

Asn Val Gln Asp Ser Thr Asn Pro Leu Asp Phe Leu Pro Lys Gly Phe
                325                 330                 335

Leu Glu Arg Thr Lys Gly Leu Gly Leu Val Val Pro Asn Trp Ala Pro
            340                 345                 350

Gln Ala Gln Ile Leu Ser His Gly Ser Thr Gly Gly Phe Leu Thr His
        355                 360                 365

Cys Gly Trp Asn Ser Thr Leu Glu Ser Val Val His Gly Val Pro Leu
    370                 375                 380

Ile Ala Trp Pro Leu Tyr Ala Glu Gln Lys Met Asn Ala Val Met Leu
385                 390                 395                 400

Thr Glu Asp Ile Lys Val Ala Leu Arg Pro Lys Ala Asn Glu Asn Gly
                405                 410                 415

Leu Val Gly Arg Leu Glu Ile Ala Lys Val Val Lys Gly Leu Met Glu
```

```
                     420                425                430
Gly Glu Glu Gly Lys Gly Val Arg Thr Arg Met Arg Asp Leu Lys Asp
                435                440                445

Ala Ala Ala Lys Val Leu Ser Gln Asp Gly Ser Ser Thr Lys Ala Leu
450                455                460

Ala Glu Leu Ala Thr Lys Leu Lys Asn Lys Val Leu Ile Asn
465                470                475

<210> SEQ ID NO 6
<211> LENGTH: 480
<212> TYPE: PRT
<213> ORGANISM: Arabidopsis thaliana

<400> SEQUENCE: 6

Met Glu Glu Ser Lys Thr Pro His Val Ala Ile Ile Pro Ser Pro Gly
1               5                  10                 15

Met Gly His Leu Ile Pro Leu Val Glu Phe Ala Lys Arg Leu Val His
                20                 25                 30

Leu His Gly Leu Thr Val Thr Phe Val Ile Ala Gly Glu Gly Pro Pro
            35                 40                 45

Ser Lys Ala Gln Arg Thr Val Leu Asp Ser Leu Pro Ser Ser Ile Ser
50                 55                 60

Ser Val Phe Leu Pro Pro Val Asp Leu Thr Asp Leu Ser Ser Ser Thr
65                 70                 75                 80

Arg Ile Glu Ser Arg Ile Ser Leu Thr Val Thr Arg Ser Asn Pro Glu
                85                 90                 95

Leu Arg Lys Val Phe Asp Ser Phe Glu Gly Gly Arg Leu Pro Thr
                100                105                110

Ala Leu Val Val Asp Leu Phe Gly Thr Asp Ala Phe Asp Val Ala Val
            115                120                125

Glu Phe His Val Pro Pro Tyr Ile Phe Tyr Pro Thr Thr Ala Asn Val
130                135                140

Leu Ser Phe Phe Leu His Leu Pro Lys Leu Asp Glu Thr Val Ser Cys
145                150                155                160

Glu Phe Arg Glu Leu Thr Glu Pro Leu Met Leu Pro Gly Cys Val Pro
                165                170                175

Val Ala Gly Lys Asp Phe Leu Asp Pro Ala Gln Asp Arg Lys Asp Asp
            180                185                190

Ala Tyr Lys Trp Leu Leu His Asn Thr Lys Arg Tyr Lys Glu Ala Glu
            195                200                205

Gly Ile Leu Val Asn Thr Phe Phe Glu Leu Glu Pro Asn Ala Ile Lys
210                215                220

Ala Leu Gln Glu Pro Gly Leu Asp Lys Pro Val Tyr Pro Val Gly
225                230                235                240

Pro Leu Val Asn Ile Gly Lys Gln Glu Ala Lys Gln Thr Glu Glu Ser
                245                250                255

Glu Cys Leu Lys Trp Leu Asp Asn Gln Pro Leu Gly Ser Val Leu Tyr
                260                265                270

Val Ser Phe Gly Ser Gly Gly Thr Leu Thr Cys Glu Gln Leu Asn Glu
            275                280                285

Leu Ala Leu Gly Leu Ala Asp Ser Glu Gln Arg Phe Leu Trp Val Ile
            290                295                300

Arg Ser Pro Ser Gly Ile Ala Asn Ser Ser Tyr Phe Asp Ser His Ser
305                310                315                320
```

```
Gln Thr Asp Pro Leu Thr Phe Leu Pro Pro Gly Phe Leu Glu Arg Thr
                325                 330                 335

Lys Lys Arg Gly Phe Val Ile Pro Phe Trp Ala Pro Gln Ala Gln Val
            340                 345                 350

Leu Ala His Pro Ser Thr Gly Gly Phe Leu Thr His Cys Gly Trp Asn
        355                 360                 365

Ser Thr Leu Glu Ser Val Val Ser Gly Ile Pro Leu Ile Ala Trp Pro
    370                 375                 380

Leu Tyr Ala Glu Gln Lys Met Asn Ala Val Leu Ser Glu Asp Ile
385                 390                 395                 400

Arg Ala Leu Arg Pro Arg Ala Gly Asp Asp Gly Leu Val Arg Arg
                405                 410                 415

Glu Glu Val Ala Arg Val Val Lys Gly Leu Met Glu Gly Glu Gly
                420                 425                 430

Lys Gly Val Arg Asn Lys Met Lys Glu Leu Lys Glu Ala Ala Cys Arg
            435                 440                 445

Val Leu Lys Asp Asp Gly Thr Ser Thr Lys Ala Leu Ser Leu Val Ala
        450                 455                 460

Leu Lys Trp Lys Ala His Lys Lys Glu Leu Glu Gln Asn Gly Asn His
465                 470                 475                 480
```

<210> SEQ ID NO 7
<211> LENGTH: 481
<212> TYPE: PRT
<213> ORGANISM: Arabidopsis thaliana

<400> SEQUENCE: 7

```
Met His Ile Thr Lys Pro His Ala Ala Met Phe Ser Ser Pro Gly Met
1               5                   10                  15

Gly His Val Ile Pro Val Ile Glu Leu Gly Lys Arg Leu Ser Ala Asn
                20                  25                  30

Asn Gly Phe His Val Thr Val Phe Val Leu Glu Thr Asp Ala Ala Ser
            35                  40                  45

Ala Gln Ser Lys Phe Leu Asn Ser Thr Gly Val Asp Ile Val Lys Leu
        50                  55                  60

Pro Ser Pro Asp Ile Tyr Gly Leu Val Asp Pro Asp His Val Val
65                  70                  75                  80

Thr Lys Ile Gly Val Ile Met Arg Ala Ala Val Pro Ala Leu Arg Ser
                85                  90                  95

Lys Ile Ala Ala Met His Gln Lys Pro Thr Ala Leu Ile Val Asp Leu
            100                 105                 110

Phe Gly Thr Asp Ala Leu Cys Leu Ala Lys Glu Phe Asn Met Leu Ser
        115                 120                 125

Tyr Val Phe Ile Pro Thr Asn Ala Arg Phe Leu Gly Val Ser Ile Tyr
    130                 135                 140

Tyr Pro Asn Leu Asp Lys Asp Ile Lys Glu Glu His Thr Val Gln Arg
145                 150                 155                 160

Asn Pro Leu Ala Ile Pro Gly Cys Glu Pro Val Arg Phe Glu Asp Thr
                165                 170                 175

Leu Asp Ala Tyr Leu Val Pro Asp Glu Pro Val Tyr Arg Asp Phe Val
            180                 185                 190

Arg His Gly Leu Ala Tyr Pro Lys Ala Asp Gly Ile Leu Val Asn Thr
        195                 200                 205

Trp Glu Glu Met Glu Pro Lys Ser Leu Lys Ser Leu Leu Asn Pro Lys
    210                 215                 220
```

```
Leu Leu Gly Arg Val Ala Arg Val Pro Val Tyr Pro Ile Gly Pro Leu
225                 230                 235                 240

Cys Arg Pro Ile Gln Ser Ser Glu Thr Asp His Pro Val Leu Asp Trp
            245                 250                 255

Leu Asn Glu Gln Pro Asn Glu Ser Val Leu Tyr Ile Ser Phe Gly Ser
        260                 265                 270

Gly Gly Cys Leu Ser Ala Lys Gln Leu Thr Glu Leu Ala Trp Gly Leu
    275                 280                 285

Glu Gln Ser Gln Gln Arg Phe Val Trp Val Arg Pro Pro Val Asp
290                 295                 300

Gly Ser Cys Cys Ser Glu Tyr Val Ser Ala Asn Gly Gly Thr Glu
305                 310                 315                 320

Asp Asn Thr Pro Glu Tyr Leu Pro Glu Gly Phe Val Ser Arg Thr Ser
            325                 330                 335

Asp Arg Gly Phe Val Val Pro Ser Trp Ala Pro Gln Ala Glu Ile Leu
            340                 345                 350

Ser His Arg Ala Val Gly Gly Phe Leu Thr His Cys Gly Trp Ser Ser
        355                 360                 365

Thr Leu Glu Ser Val Val Gly Gly Val Pro Met Ile Ala Trp Pro Leu
370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
            405                 410                 415

Ile Glu Ala Leu Val Arg Lys Val Met Thr Glu Lys Glu Gly Glu Ala
        420                 425                 430

Met Arg Arg Lys Val Lys Lys Leu Arg Asp Ser Ala Glu Met Ser Leu
        435                 440                 445

Ser Ile Asp Gly Gly Gly Leu Ala His Glu Ser Leu Cys Arg Val Thr
    450                 455                 460

Lys Glu Cys Gln Arg Phe Leu Glu Arg Val Val Asp Leu Ser Arg Gly
465                 470                 475                 480

Ala

<210> SEQ ID NO 8
<211> LENGTH: 481
<212> TYPE: PRT
<213> ORGANISM: Arabidopsis thaliana

<400> SEQUENCE: 8

Met His Ile Thr Lys Pro His Ala Ala Met Phe Ser Ser Pro Gly Met
1               5                   10                  15

Gly His Val Leu Pro Val Ile Glu Leu Ala Lys Arg Leu Ser Ala Asn
            20                  25                  30

His Gly Phe His Val Thr Val Phe Val Leu Glu Thr Asp Ala Ala Ser
        35                  40                  45

Val Gln Ser Lys Leu Leu Asn Ser Thr Gly Val Asp Ile Val Asn Leu
    50                  55                  60

Pro Ser Pro Asp Ile Ser Gly Leu Val Asp Pro Asn Ala His Val Val
65                  70                  75                  80

Thr Lys Ile Gly Val Ile Met Arg Glu Ala Val Pro Thr Leu Arg Ser
                85                  90                  95

Lys Ile Val Ala Met His Gln Asn Pro Thr Ala Leu Ile Ile Asp Leu
            100                 105                 110
```

Phe Gly Thr Asp Ala Leu Cys Leu Ala Ala Glu Leu Asn Met Leu Thr
    115                 120                 125

Tyr Val Phe Ile Ala Ser Asn Ala Arg Tyr Leu Gly Val Ser Ile Tyr
    130                 135                 140

Tyr Pro Thr Leu Asp Glu Val Ile Lys Glu His Thr Val Gln Arg
145                 150                 155                 160

Lys Pro Leu Thr Ile Pro Gly Cys Glu Pro Val Arg Phe Glu Asp Ile
                165                 170                 175

Met Asp Ala Tyr Leu Val Pro Asp Glu Pro Val Tyr His Asp Leu Val
                180                 185                 190

Arg His Cys Leu Ala Tyr Pro Lys Ala Asp Gly Ile Leu Val Asn Thr
        195                 200                 205

Trp Glu Glu Met Glu Pro Lys Ser Leu Lys Ser Leu Gln Asp Pro Lys
    210                 215                 220

Leu Leu Gly Arg Val Ala Arg Val Pro Val Tyr Pro Val Gly Pro Leu
225                 230                 235                 240

Cys Arg Pro Ile Gln Ser Ser Thr Thr Asp His Pro Val Phe Asp Trp
                245                 250                 255

Leu Asn Lys Gln Pro Asn Glu Ser Val Leu Tyr Ile Ser Phe Gly Ser
                260                 265                 270

Gly Gly Ser Leu Thr Ala Gln Gln Leu Thr Glu Leu Ala Trp Gly Leu
        275                 280                 285

Glu Glu Ser Gln Gln Arg Phe Ile Trp Val Val Arg Pro Pro Val Asp
    290                 295                 300

Gly Ser Ser Cys Ser Asp Tyr Phe Ser Ala Lys Gly Gly Val Thr Lys
305                 310                 315                 320

Asp Asn Thr Pro Glu Tyr Leu Pro Glu Gly Phe Val Thr Arg Thr Cys
                325                 330                 335

Asp Arg Gly Phe Met Ile Pro Ser Trp Ala Pro Gln Ala Glu Ile Leu
                340                 345                 350

Ala His Gln Ala Val Gly Gly Phe Leu Thr His Cys Gly Trp Ser Ser
        355                 360                 365

Thr Leu Glu Ser Val Leu Cys Gly Val Pro Met Ile Ala Trp Pro Leu
    370                 375                 380

Phe Ala Glu Gln Asn Met Asn Ala Ala Leu Leu Ser Asp Glu Leu Gly
385                 390                 395                 400

Ile Ser Val Arg Val Asp Asp Pro Lys Glu Ala Ile Ser Arg Ser Lys
                405                 410                 415

Ile Glu Ala Met Val Arg Lys Val Met Ala Glu Asp Glu Gly Glu Glu
                420                 425                 430

Met Arg Arg Lys Val Lys Lys Leu Arg Asp Thr Ala Glu Met Ser Leu
        435                 440                 445

Ser Ile His Gly Gly Gly Ser Ala His Glu Ser Leu Cys Arg Val Thr
    450                 455                 460

Lys Glu Cys Gln Arg Phe Leu Glu Cys Val Gly Asp Leu Gly Arg Gly
465                 470                 475                 480

Ala

<210> SEQ ID NO 9
<211> LENGTH: 295
<212> TYPE: PRT
<213> ORGANISM: Homo sapiens

<400> SEQUENCE: 9

```
Met Glu Leu Ile Gln Asp Thr Ser Arg Pro Leu Glu Tyr Val Lys
1               5                   10                  15

Gly Val Pro Leu Ile Lys Tyr Phe Ala Glu Ala Leu Gly Pro Leu Gln
            20                  25                  30

Ser Phe Gln Ala Arg Pro Asp Asp Leu Leu Ile Ser Thr Tyr Pro Lys
        35                  40                  45

Ser Gly Thr Thr Trp Val Ser Gln Ile Leu Asp Met Ile Tyr Gln Gly
50                  55                  60

Gly Asp Leu Glu Lys Cys His Arg Ala Pro Ile Phe Met Arg Val Pro
65                  70                  75                  80

Phe Leu Glu Phe Lys Ala Pro Gly Ile Pro Ser Gly Met Glu Thr Leu
                85                  90                  95

Lys Asp Thr Pro Ala Pro Arg Leu Leu Lys Thr His Leu Pro Leu Ala
            100                 105                 110

Leu Leu Pro Gln Thr Leu Leu Asp Gln Lys Val Lys Val Val Tyr Val
        115                 120                 125

Ala Arg Asn Ala Lys Asp Val Ala Val Ser Tyr Tyr His Phe Tyr His
130                 135                 140

Met Ala Lys Val His Pro Glu Pro Gly Thr Trp Asp Ser Phe Leu Glu
145                 150                 155                 160

Lys Phe Met Val Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Val Asp Phe Val Val
210                 215                 220

Gln His Thr Ser Phe Lys Glu Met Lys Lys Asn Pro Met Thr Asn Tyr
225                 230                 235                 240

Thr Thr Val Pro Gln Glu Phe Met Asp His Ser Ile Ser Pro Phe Met
                245                 250                 255

Arg Lys Gly Met Ala Gly Asp Trp Lys Thr Thr Phe Thr Val Ala Gln
            260                 265                 270

Asn Glu Arg Phe Asp Ala Asp Tyr Ala Glu Lys Met Ala Gly Cys Ser
        275                 280                 285

Leu Ser Phe Arg Ser Glu Leu
        290                 295

<210> SEQ ID NO 10
<211> LENGTH: 295
<212> TYPE: PRT
<213> ORGANISM: Homo sapiens

<400> SEQUENCE: 10

Met Glu Leu Ile Gln Asp Thr Ser Arg Pro Leu Glu Tyr Val Lys
1               5                   10                  15

Gly Val Pro Leu Ile Lys Tyr Phe Ala Glu Ala Leu Gly Pro Leu Gln
            20                  25                  30

Ser Phe Gln Ala Arg Pro Asp Asp Leu Leu Ile Ser Thr Tyr Pro Lys
        35                  40                  45

Ser Gly Thr Thr Trp Val Ser Gln Ile Leu Asp Met Ile Tyr Gln Gly
50                  55                  60

Gly Asp Leu Glu Lys Cys His Arg Ala Pro Ile Phe Met Arg Val Pro
```

```
                65                  70                  75                  80
        Phe Leu Glu Phe Lys Ala Pro Gly Ile Pro Ser Gly Met Glu Thr Leu
                        85                  90                  95

Lys Asp Thr Pro Ala Pro Arg Leu Leu Lys Thr His Leu Pro Leu Ala
                        100                 105                 110

Leu Leu Pro Gln Thr Leu Leu Asp Gln Lys Val Lys Val Val Tyr Val
                        115                 120                 125

Ala Arg Asn Ala Lys Asp Val Ala Val Ser Tyr Tyr His Phe Tyr His
                130                 135                 140

Met Ala Lys Val His Pro Glu Pro Gly Thr Trp Asp Ser Phe Leu Glu
        145                 150                 155                 160

Lys Phe Met Val Gly Glu Val Ser Tyr Gly Ser Trp Tyr Gln His Val
                            165                 170                 175

Gln Glu Trp Trp Glu Leu Ser Arg Thr His Pro Val Leu Tyr Leu Phe
                        180                 185                 190

Tyr Glu Asp Met Lys Glu Asn Pro Lys Arg Glu Ile Gln Lys Ile Leu
                        195                 200                 205

Glu Phe Val Gly Arg Ser Leu Pro Glu Glu Thr Val Asp Phe Val Val
                        210                 215                 220

Gln His Thr Ser Phe Lys Glu Met Lys Lys Asn Pro Met Thr Asn Tyr
        225                 230                 235                 240

Thr Thr Val Pro Gln Glu Phe Met Gly His Ser Ile Ser Pro Phe Met
                        245                 250                 255

Arg Lys Gly Met Ala Gly Asp Trp Lys Thr Thr Phe Thr Val Ala Gln
                        260                 265                 270

Asn Glu Arg Phe Asp Ala Asp Tyr Ala Glu Lys Met Ala Gly Cys Ser
                        275                 280                 285

Leu Ser Phe Arg Ser Glu Leu
                        290                 295

<210> SEQ ID NO 11
<211> LENGTH: 295
<212> TYPE: PRT
<213> ORGANISM: Homo sapiens

<400> SEQUENCE: 11

Met Glu Leu Ile Gln Asp Thr Ser Arg Pro Pro Leu Glu Tyr Val Lys
        1               5                   10                  15

Gly Val Pro Leu Ile Lys Tyr Phe Ala Glu Ala Leu Gly Pro Leu Gln
                        20                  25                  30

Ser Phe Gln Ala Arg Pro Asp Asp Leu Leu Ile Ser Thr Tyr Pro Lys
                        35                  40                  45

Ser Gly Thr Thr Trp Val Ser Glu Ile Leu Asp Met Ile Tyr Gln Gly
                50                  55                  60

Gly Asp Val Glu Lys Cys His Arg Ala Pro Ile Phe Met Arg Val Pro
        65                  70                  75                  80

Phe Leu Glu Phe Lys Ala Pro Gly Ile Pro Ser Gly Met Glu Thr Leu
                        85                  90                  95

Lys Asp Thr Pro Ser Pro Arg Leu Leu Lys Thr His Leu Pro Leu Ala
                        100                 105                 110

Leu Leu Pro Gln Ser Leu Leu Asp Gln Lys Val Lys Val Val Tyr Val
                        115                 120                 125

Ala Arg Asn Ala Lys Asp Val Ala Val Ser Tyr Tyr His Phe Tyr His
                130                 135                 140
```

Met Ala Lys Val His Pro Glu Pro Gly Thr Trp Asp Ser Phe Leu Glu
145                 150                 155                 160

Lys Phe Met Val Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Val Asp Leu Val Val
    210                 215                 220

Gln His Thr Ser Phe Lys Glu Met Lys Lys Asn Pro Met Thr Asn Tyr
225                 230                 235                 240

Thr Thr Ile Pro Gln Glu Phe Met Gly His Ser Ile Ser Pro Phe Met
                245                 250                 255

Arg Lys Gly Met Ala Gly Asp Trp Lys Thr Thr Phe Thr Val Ala Gln
                260                 265                 270

Asn Glu Arg Phe Asp Ala Asp Tyr Ala Glu Lys Met Ala Gly Cys Ser
            275                 280                 285

Leu Ser Phe Arg Ser Glu Leu
        290                 295

<210> SEQ ID NO 12
<211> LENGTH: 295
<212> TYPE: PRT
<213> ORGANISM: Homo sapiens

<400> SEQUENCE: 12

Met Glu Leu Ile Gln Asp Thr Ser Arg Pro Pro Leu Glu Tyr Val Lys
1               5                   10                  15

Gly Val Pro Leu Ile Lys Tyr Phe Ala Glu Ala Leu Gly Pro Leu Gln
                20                  25                  30

Ser Phe Gln Ala Arg Pro Asp Asp Leu Leu Ile Asn Thr Tyr Pro Lys
            35                  40                  45

Ser Gly Thr Thr Trp Val Ser Gln Ile Leu Asp Met Ile Tyr Gln Gly
        50                  55                  60

Gly Asp Leu Glu Lys Cys Asn Arg Ala Pro Ile Tyr Val Arg Val Pro
65                  70                  75                  80

Phe Leu Glu Val Asn Asp Pro Gly Glu Pro Ser Gly Leu Glu Thr Leu
                85                  90                  95

Lys Asp Thr Pro Pro Arg Leu Ile Lys Ser His Leu Pro Leu Ala
            100                 105                 110

Leu Leu Pro Gln Thr Leu Leu Asp Gln Lys Val Lys Val Val Tyr Val
        115                 120                 125

Ala Arg Asn Pro Lys Asp Val Ala Val Ser Tyr Tyr His Phe His Arg
    130                 135                 140

Met Glu Lys Ala His Pro Glu Pro Gly Thr Trp Asp Ser Phe Leu Glu
145                 150                 155                 160

Lys Phe Met Ala Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Met Asp Phe Met Val
    210                 215                 220

```
Gln His Thr Ser Phe Lys Glu Met Lys Lys Asn Pro Met Thr Asn Tyr
225                 230                 235                 240

Thr Thr Val Pro Gln Glu Leu Met Asp His Ser Ile Ser Pro Phe Met
            245                 250                 255

Arg Lys Gly Met Ala Gly Asp Trp Lys Thr Thr Phe Thr Val Ala Gln
        260                 265                 270

Asn Glu Arg Phe Asp Ala Asp Tyr Ala Glu Lys Met Ala Gly Cys Ser
    275                 280                 285

Leu Ser Phe Arg Ser Glu Leu
    290                 295

<210> SEQ ID NO 13
<211> LENGTH: 295
<212> TYPE: PRT
<213> ORGANISM: Homo sapiens

<400> SEQUENCE: 13

Met Glu Leu Ile Gln Asp Thr Ser Arg Pro Leu Glu Tyr Val Lys
1               5                   10                  15

Gly Val Pro Leu Ile Lys Tyr Phe Ala Glu Ala Leu Gly Pro Leu Gln
            20                  25                  30

Ser Phe Gln Ala Arg Pro Asp Asp Leu Leu Ile Asn Thr Tyr Pro Lys
        35                  40                  45

Ser Gly Thr Thr Trp Val Ser Gln Ile Leu Asp Met Ile Tyr Gln Gly
    50                  55                  60

Gly Asp Leu Glu Lys Cys Asn Arg Ala Pro Ile Tyr Val Arg Val Pro
65                  70                  75                  80

Phe Leu Glu Val Asn Asp Pro Gly Glu Pro Ser Gly Leu Glu Thr Leu
                85                  90                  95

Lys Asp Thr Pro Pro Arg Leu Ile Lys Ser His Leu Pro Leu Ala
            100                 105                 110

Leu Leu Pro Gln Thr Leu Leu Asp Gln Lys Val Lys Val Val Tyr Val
            115                 120                 125

Ala Arg Asn Pro Lys Asp Val Ala Val Ser Tyr Tyr His Phe His Arg
130                 135                 140

Met Glu Lys Ala His Pro Glu Pro Gly Thr Trp Asp Ser Phe Leu Glu
145                 150                 155                 160

Lys Phe Met Ala Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Met Asp Phe Met Val
210                 215                 220

Gln His Thr Ser Phe Lys Glu Met Lys Lys Asn Pro Met Thr Asn Tyr
225                 230                 235                 240

Thr Thr Val Pro Gln Glu Leu Met Gly His Ser Ile Ser Pro Phe Met
            245                 250                 255

Arg Lys Gly Met Ala Gly Asp Trp Lys Thr Thr Phe Thr Val Ala Gln
        260                 265                 270

Asn Glu Arg Phe Asp Ala Asp Tyr Ala Glu Lys Met Ala Gly Cys Ser
    275                 280                 285

Leu Ser Phe Arg Ser Glu Leu
```

```
            290                 295

<210> SEQ ID NO 14
<211> LENGTH: 295
<212> TYPE: PRT
<213> ORGANISM: Homo sapiens

<400> SEQUENCE: 14

Met Glu Leu Ile Gln Asp Thr Ser Arg Pro Leu Glu Tyr Val Lys
1               5                   10                  15

Gly Val Pro Leu Ile Lys Tyr Phe Ala Glu Ala Leu Gly Pro Leu Gln
                20                  25                  30

Ser Phe Gln Ala Arg Pro Asp Asp Leu Leu Ile Asn Thr Tyr Pro Lys
            35                  40                  45

Ser Gly Thr Thr Trp Val Ser Glu Ile Leu Asp Met Ile Tyr Gln Gly
        50                  55                  60

Gly Asp Val Glu Lys Cys Asn Arg Ala Pro Ile Tyr Val Arg Val Pro
65                  70                  75                  80

Phe Leu Glu Val Asn Asp Pro Gly Glu Pro Ser Gly Leu Glu Thr Leu
                85                  90                  95

Lys Asp Thr Pro Pro Pro Arg Leu Ile Lys Ser His Leu Pro Leu Ala
            100                 105                 110

Leu Leu Pro Gln Ser Leu Leu Asp Gln Lys Val Lys Val Val Tyr Val
        115                 120                 125

Ala Arg Asn Pro Lys Asp Val Ala Val Ser Tyr Tyr His Phe His Arg
130                 135                 140

Met Glu Lys Ala His Pro Glu Pro Gly Thr Trp Asp Ser Phe Leu Glu
145                 150                 155                 160

Lys Phe Met Ala Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Met Asp Leu Met Val
210                 215                 220

Gln His Thr Ser Phe Lys Glu Met Lys Lys Asn Pro Met Thr Asn Tyr
225                 230                 235                 240

Thr Thr Ile Pro Gln Glu Leu Met Gly His Ser Ile Ser Pro Phe Met
                245                 250                 255

Arg Lys Gly Met Ala Gly Asp Trp Lys Thr Thr Phe Thr Val Ala Gln
            260                 265                 270

Asn Glu Arg Phe Asp Ala Asp Tyr Ala Glu Lys Met Ala Gly Cys Ser
        275                 280                 285

Leu Ser Phe Arg Ser Glu Leu
        290                 295

<210> SEQ ID NO 15
<211> LENGTH: 345
<212> TYPE: PRT
<213> ORGANISM: Indigofera tinctoria

<400> SEQUENCE: 15

Asn Leu Ala Val Thr Phe Ile Ile Pro Thr Asp Gly Pro Pro Ser Lys
1               5                   10                  15

Ala Gln Lys Thr Val Leu His Ser Leu Pro Pro Ala Ile Ser His Thr
```

```
            20                  25                  30
Phe Leu Pro Pro Val Asn Leu Ser Asp Val Pro Lys Asp Ala Lys Ile
            35                  40                  45
Glu Thr Ile Ile Ser Leu Thr Val Leu Arg Ser Leu Pro Ser Ile Arg
            50                  55                  60
Asp Leu Phe Arg Ser Leu Thr Ala Ser Ala Leu Val Val Asp Leu Phe
65                  70                  75                  80
Gly Thr Asp Ala Phe Asp Val Ala Lys Glu Phe Asn Val Ser Pro Tyr
                    85                  90                  95
Ile Phe Phe Pro Ser Thr Ala Met Ala Leu Ser Phe Phe Leu His Leu
                    100                 105                 110
Pro His Leu Asp Gln Glu Val His Ser Glu Tyr Arg Glu Leu Ala Glu
            115                 120                 125
Pro Val Lys Ile Pro Gly Cys Val Pro Ile His Gly Lys Asp Leu Leu
            130                 135                 140
Asp Pro Val Gln Asp Arg Lys Asn Asp Ala Tyr Lys Trp Val Leu His
145                 150                 155                 160
His Thr Lys Arg Tyr Arg Glu Ala Glu Gly Ile Ile Glu Asn Ser Phe
                    165                 170                 175
Leu Glu Leu Glu Pro Gly Pro Ile Lys Glu Leu Leu Lys Glu Glu Pro
                    180                 185                 190
Gly Lys Pro Pro Val Tyr Ser Val Gly Pro Leu Val Asn Val Glu Thr
            195                 200                 205
Gly Arg Ala Gly Asn Gly Ser Glu Cys Leu Lys Trp Leu Asp Glu Gln
            210                 215                 220
Pro Pro Gly Ser Val Leu Phe Val Ser Phe Gly Ser Gly Gly Thr Leu
225                 230                 235                 240
Ser Ser Ala Gln Ile Asn Glu Leu Ala Leu Gly Leu Glu Ala Ser Glu
                    245                 250                 255
Gln Arg Phe Leu Trp Val Val Arg Ser Pro Asn Asp Lys Val Ala Asn
                    260                 265                 270
Ala Ser Tyr Phe Ser Ala Asp Ser Gln Ala Asp Pro Phe Asp Phe Leu
            275                 280                 285
Pro Lys Glu Phe Val Lys Arg Thr Lys Glu Arg Gly Leu Val Val Ser
            290                 295                 300
Ser Trp Ala Pro Gln Thr Gln Val Leu Ala His Gly Ser Thr Gly Gly
305                 310                 315                 320
Phe Leu Thr His Cys Gly Trp Asn Ser Ile Leu Glu Ser Val Val Asn
                    325                 330                 335
Gly Val Pro Leu Ile Ala Trp Pro Leu
                    340                 345

<210> SEQ ID NO 16
<211> LENGTH: 348
<212> TYPE: PRT
<213> ORGANISM: Indigofera tinctoria

<400> SEQUENCE: 16

Glu Leu Asn Ile Leu Ser Tyr Leu Tyr Phe Pro Ser Thr Ala Met Leu
1               5                   10                  15
Leu Ser Leu Cys Leu Tyr Ser Ser Lys Leu Asp Lys Glu Ile Ser Ile
            20                  25                  30
Glu Tyr Lys Asp Leu Leu Glu Pro Ile Lys Leu Pro Gly Cys Ile Pro
            35                  40                  45
```

```
Ile Ser Pro Ser Asp Leu Pro Asp Pro Leu Gln Asp Arg Ser Gly Glu
    50                  55                  60

Ser Tyr Gln Gln Phe Leu Glu Ala Asn Glu Arg Phe Tyr Leu Ala Asp
65                  70                  75                  80

Gly Ile Leu Val Asn Ser Phe Val Glu Met Glu Gly Gly Thr Ile Arg
                85                  90                  95

Ala Leu Gln Glu Glu Ser Arg Gly Ile Pro Ser Val Tyr Ala Ile
                100                 105                 110

Gly Pro Phe Val Lys Met Gly Ser Cys Ser Cys Asp Tyr Glu Gly
            115                 120                 125

Ser Glu Lys Asp Asn Tyr Leu Thr Trp Leu Asp Lys Gln Glu Lys Cys
130                 135                 140

Ser Ile Leu Tyr Val Ser Phe Gly Ser Gly Gly Thr Leu Phe His Asp
145                 150                 155                 160

Gln Ile Ile Glu Leu Ala Trp Gly Leu Glu Leu Ser Gly Gln Lys Phe
                165                 170                 175

Leu Trp Val Leu Arg Pro Pro Ser Lys Phe Gly Ile Val Ala Asp Leu
            180                 185                 190

Ser Ala Val Asn Leu Asp Pro Leu Gln Phe Leu Pro Ser Gly Phe Leu
            195                 200                 205

Glu Arg Thr Lys Gly Gln Gly Leu Val Val Pro Tyr Trp Ala Thr Gln
210                 215                 220

Ile Glu Ile Leu Ser His Ser Ala Ile Gly Gly Tyr Leu Cys His Cys
225                 230                 235                 240

Gly Trp Asn Ser Ile Leu Glu Ser Val Val His Gly Val Pro Ile Ile
                245                 250                 255

Ala Trp Pro Leu Phe Ala Glu Gln Lys Met Asn Ala Ala Met Leu Thr
            260                 265                 270

Thr Gly Leu Lys Val Ala Leu Arg Pro Lys Val Ser Glu Lys Gly Met
            275                 280                 285

Ile Glu Arg Glu Glu Ile Ala Val Val Ile Lys Asn Leu Met Val Gly
            290                 295                 300

Glu Glu Val Ala Lys Glu Ile Arg Gln Arg Met Lys Trp Leu Lys Asp
305                 310                 315                 320

Ala Ala His Asp Ala Leu Lys Glu Asp Gly Ser Ser Thr Arg Thr Leu
                325                 330                 335

Thr Gln Leu Ala Ile Lys Trp Glu Ser Leu Ala Val
            340                 345

<210> SEQ ID NO 17
<211> LENGTH: 401
<212> TYPE: PRT
<213> ORGANISM: Indigofera suffruticosa
<220> FEATURE:
<221> NAME/KEY: VARIANT
<222> LOCATION: 240, 243, 267, 268, 277, 279, 299, 300, 301, 302, 358,
      364, 365, 367, 370, 373, 379, 383, 386, 388, 395, 396
<223> OTHER INFORMATION: Xaa = Any Amino Acid

<400> SEQUENCE: 17

Ser Val Thr Phe Ile Ile Pro Thr Asp Gly Pro Pro Ser Lys Ala Gln
1               5                   10                  15

Lys Thr Val Leu Gln Ser Leu Pro Pro Ala Ile Ser His Thr Phe Leu
                20                  25                  30

Pro Pro Val Asn Leu Ser Asp Val Pro Lys Asp Ala Met Ile Glu Thr
            35                  40                  45
```

```
Ile Ile Ser Leu Thr Val Leu Arg Ser Leu Pro Ser Ile Arg Asp Leu
    50                  55                  60

Phe Arg Ser Leu Ser Pro Ser Val Leu Val Leu Asp Leu Phe Gly Thr
 65                  70                  75                  80

Asp Ala Phe Asp Val Ala Lys Glu Phe Asn Val Ser Pro Tyr Ile Phe
                 85                  90                  95

Phe Pro Ser Thr Ala Met Val Leu Ser Phe Phe Leu His Leu Pro His
                100                 105                 110

Leu Asp Arg Glu Val His Ser Glu Tyr Arg Glu Leu Ala Glu Pro Val
                115                 120                 125

Lys Ile Pro Gly Cys Val Pro Val His Gly Lys Asp Leu Leu Ala Pro
130                 135                 140

Val Gln Asp Arg Lys Asn Asp Ala Tyr Lys Trp Val Leu His His Thr
145                 150                 155                 160

Lys Arg Tyr Arg Glu Ala Glu Gly Ile Ile Glu Asn Ser Phe Leu Glu
                165                 170                 175

Leu Glu Pro Gly Pro Ile Lys Glu Leu Leu Lys Glu Asp Ser Val Lys
                180                 185                 190

Pro Pro Val Tyr Pro Val Gly Pro Leu Val Asn Val Glu Thr Gly Arg
                195                 200                 205

Ala Gly Asn Gly Ser Glu Cys Leu Lys Trp Leu Asp Glu Gln Pro His
210                 215                 220

Gly Ser Val Leu Phe Val Ser Phe Gly Ser Gly Gly Thr Leu Ser Xaa
225                 230                 235                 240

Ala Gln Xaa Asn Glu Leu Ala Leu Gly Leu Glu Ala Ser Glu Glx Arg
                245                 250                 255

Phe Leu Trp Val Val Arg Ser Pro Asn Asp Xaa Xaa Ala Asn Ala Ser
                260                 265                 270

Phe Phe Ser Ala Xaa Ser Xaa Ala Asp Pro Phe Asp Phe Leu Pro Lys
                275                 280                 285

Gly Phe Val Glu Arg Thr Lys Glx Arg Gly Xaa Xaa Xaa Xaa Ser Trp
                290                 295                 300

Ala Pro Gln Pro Gln Val Leu Ala His Gly Ser Thr Gly Gly Phe Leu
305                 310                 315                 320

Thr His Cys Gly Trp Asn Ser Ile Leu Glu Ser Val Val Asn Gly Val
                325                 330                 335

Pro Leu Ile Ala Trp Pro Leu Tyr Ala Glu Gln Lys Met Asn Ala Val
                340                 345                 350

Met Leu Thr Gln Asp Xaa Lys Val Ala Leu Arg Xaa Xaa Asp Xaa Asx
                355                 360                 365

Gly Xaa Leu Val Xaa Arg Glu Glu Ile Ala Xaa Val Val Lys Xaa Leu
370                 375                 380

Met Xaa Gly Xaa Glu Gly Lys Lys Val Arg Xaa Xaa Met Lys Asp Leu
385                 390                 395                 400

Lys

<210> SEQ ID NO 18
<211> LENGTH: 470
<212> TYPE: PRT
<213> ORGANISM: Indigofera suffruticosa

<400> SEQUENCE: 18

Met Ala Lys Thr Val His Ile Ala Val Val Pro Ser Ala Gly Phe Ser
 1               5                  10                  15
```

```
His Leu Val Pro Val Ile Glu Phe Ser Lys Arg Leu Ile Lys His His
             20                  25                  30

Pro Asn Phe His Val Thr Cys Ile Ile Pro Ser Leu Glu Ser Pro Pro
         35                  40                  45

Gln Ser Ser Lys Ala Tyr Leu Glu Thr Leu Pro Ser Asn Ile Asp Ser
     50                  55                  60

Ile Phe Leu Pro Pro Ile Lys Lys Glu Asp Leu Pro Gln Gly Ala Tyr
 65                  70                  75                  80

Thr Gly Ile Leu Ile Gln Leu Thr Leu Thr Tyr Ser Leu Pro Ser Ile
                 85                  90                  95

His Glu Ala Leu Lys Ser Leu Asn Ser Lys Ala Pro Leu Ala Val Leu
            100                 105                 110

Val Ala Asp Val Phe Ala Tyr Gln Ala Leu Asp Phe Ala Lys Glu Phe
        115                 120                 125

Asn Ser Leu Ser Tyr Ile Tyr Val Pro Gly Ser Ala Thr Val Leu Ser
    130                 135                 140

Leu Val Leu His Met Pro Arg Leu Asp Glu Val Ser Gly Glu Phe
145                 150                 155                 160

Lys Asp His Lys Glu Pro Ile Lys Leu Pro Gly Cys Val Pro Leu Met
                165                 170                 175

Gly Tyr Asp Leu Pro Asn Pro Val Gln Ile Arg Ser Ser Glu Ala Tyr
            180                 185                 190

Lys Gln Phe Leu Glu Arg Ala Lys Arg Met Phe Asp Val Asp Gly Met
        195                 200                 205

Leu Ile Asn Ser Phe Leu Glu Leu Glu Pro Gly Ala Ile Lys Ala Leu
    210                 215                 220

Glu Glu Lys Gly Asn Glu Arg Arg Met Arg Phe Tyr Pro Val Gly Pro
225                 230                 235                 240

Ile Thr Gln Lys Gly Ser Ser Asn Glu Val Asp Asp Ser Gly Cys
                245                 250                 255

Leu Arg Trp Leu Asp Asn Gln Pro Val Gly Ser Val Leu Tyr Val Ser
            260                 265                 270

Phe Gly Ser Gly Gly Thr Leu Ser Gln Asn Gln Ile Asp Glu Leu Ala
        275                 280                 285

Ser Gly Leu Glu Leu Ser Gly Gln Arg Phe Leu Trp Val Leu Arg Ala
    290                 295                 300

Pro Ser Asp Ser Ser Gly Ala Tyr Leu Gly Gly Ala Ser Glu Asp
305                 310                 315                 320

Pro Leu Lys Phe Leu Pro Ser Gly Phe Leu Glu Arg Thr Lys Glu Gln
                325                 330                 335

Gly Leu Val Val Pro Ser Trp Ala Pro Gln Ile Gln Val Leu Ser His
            340                 345                 350

Glu Ser Val Ser Gly Phe Leu Ser His Cys Gly Trp Asn Ser Ile Leu
        355                 360                 365

Glu Ser Val Gln Met Gly Val Pro Leu Ile Thr Trp Pro Leu Phe Ala
    370                 375                 380

Glu Gln Arg Met Asn Ala Val Met Leu Thr Asn Gly Leu Lys Val Ala
385                 390                 395                 400

Leu Arg Pro Lys Val Asn Glu Asp Gly Ile Val Lys Lys Glu Glu Ile
                405                 410                 415

Ala Lys Val Ile Arg Cys Leu Met Glu Gly Glu Glu Gly Lys Gly Met
            420                 425                 430

Arg Glu Arg Met Glu Lys Leu Lys Asn Ser Ala Ala Ile Ala Leu Glu
```

```
                435                 440                 445
Asp Gly Ser Ser Thr Gln Ser Leu Leu Gln Leu Ala Ser Asp Leu Glu
    450                 455                 460

Asn Leu Gly Gly Gly Phe
465             470

<210> SEQ ID NO 19
<211> LENGTH: 478
<212> TYPE: PRT
<213> ORGANISM: Populus trichocarpa

<400> SEQUENCE: 19

Met Ala Glu Thr Asp Ser Pro Pro His Val Ala Ile Leu Pro Ser Pro
1               5                   10                  15

Gly Met Gly His Leu Ile Pro Leu Val Glu Leu Ala Lys Arg Leu Val
                20                  25                  30

His Gln His Asn Leu Ser Val Thr Phe Ile Ile Pro Thr Asp Gly Ser
            35                  40                  45

Pro Ser Lys Ala Gln Arg Ser Val Leu Gly Ser Leu Pro Ser Thr Ile
        50                  55                  60

His Ser Val Phe Leu Pro Pro Val Asn Leu Ser Asp Leu Pro Glu Asp
65                  70                  75                  80

Val Lys Ile Glu Thr Leu Ile Ser Leu Thr Val Ala Arg Ser Leu Pro
                85                  90                  95

Ser Leu Arg Asp Val Leu Ser Ser Leu Val Ala Ser Gly Thr Arg Val
                100                 105                 110

Val Ala Leu Val Val Asp Leu Phe Gly Thr Asp Ala Phe Asp Val Ala
                115                 120                 125

Arg Glu Phe Lys Ala Ser Pro Tyr Ile Phe Tyr Pro Ala Pro Ala Met
130                 135                 140

Ala Leu Ser Leu Phe Phe Tyr Leu Pro Lys Leu Asp Glu Met Val Ser
145                 150                 155                 160

Cys Glu Tyr Ser Glu Met Gln Glu Pro Val Glu Ile Pro Gly Cys Leu
                165                 170                 175

Pro Ile His Gly Gly Glu Leu Leu Asp Pro Thr Arg Asp Arg Lys Asn
                180                 185                 190

Asp Ala Tyr Lys Trp Leu Leu His His Ser Lys Arg Tyr Arg Leu Ala
            195                 200                 205

Glu Gly Val Met Val Asn Ser Phe Ile Asp Leu Glu Arg Gly Ala Leu
    210                 215                 220

Lys Ala Leu Gln Glu Val Glu Pro Gly Lys Pro Pro Val Tyr Pro Val
225                 230                 235                 240

Gly Pro Leu Val Asn Met Asp Ser Asn Thr Ser Gly Val Glu Gly Ser
                245                 250                 255

Glu Cys Leu Lys Trp Leu Asp Gln Pro Leu Gly Ser Val Leu Phe
                260                 265                 270

Val Ser Phe Gly Ser Gly Gly Thr Leu Ser Phe Asp Gln Ile Thr Glu
            275                 280                 285

Leu Ala Leu Gly Leu Glu Met Ser Glu Gln Arg Phe Leu Trp Val Ala
        290                 295                 300

Arg Val Pro Asn Asp Lys Val Ala Asn Ala Thr Tyr Phe Ser Val Asp
305                 310                 315                 320

Asn His Lys Asp Pro Phe Asp Phe Leu Pro Lys Gly Phe Leu Asp Arg
                325                 330                 335
```

```
Thr Lys Gly Arg Gly Leu Val Val Pro Ser Trp Ala Pro Gln Ala Gln
            340                 345                 350

Val Leu Ser His Gly Ser Thr Gly Gly Phe Leu Thr His Cys Gly Trp
            355                 360                 365

Asn Ser Thr Leu Glu Ser Val Val Asn Ala Val Pro Leu Ile Val Trp
            370                 375                 380

Pro Leu Tyr Ala Glu Gln Lys Met Asn Ala Trp Met Leu Thr Lys Asp
385                 390                 395                 400

Val Glu Val Ala Leu Arg Pro Lys Ala Ser Glu Asn Gly Leu Ile Gly
                405                 410                 415

Arg Glu Glu Ile Ala Asn Ile Val Arg Gly Leu Met Glu Gly Glu Glu
            420                 425                 430

Gly Lys Arg Val Arg Asn Arg Met Lys Asp Leu Lys Asp Ala Ala Ala
            435                 440                 445

Glu Val Leu Ser Glu Ala Gly Ser Ser Thr Lys Ala Leu Ser Glu Val
            450                 455                 460

Ala Arg Lys Trp Lys Asn His Lys Cys Thr Gln Asp Cys Asn
465                 470                 475

<210> SEQ ID NO 20
<211> LENGTH: 476
<212> TYPE: PRT
<213> ORGANISM: Lycium barbarum

<400> SEQUENCE: 20

Met Ala Glu Thr Pro Val Val Thr Pro His Ile Ala Ile Leu Pro Ser
1               5                   10                  15

Pro Gly Met Gly His Leu Ile Pro Leu Val Glu Phe Ser Lys Arg Leu
            20                  25                  30

Ile Gln Asn His His Phe Ser Val Thr Leu Ile Leu Pro Thr Asp Gly
            35                  40                  45

Pro Val Ser Asn Ala Gln Lys Ile Tyr Leu Asn Ser Leu Pro Cys Ser
        50                  55                  60

Met Asp Tyr His Leu Leu Pro Pro Val Asn Phe Asp Asp Leu Pro Leu
65              70                  75                  80

Asp Thr Lys Met Glu Thr Arg Ile Ser Leu Thr Val Thr Arg Ser Leu
            85                  90                  95

Pro Ser Leu Arg Glu Val Phe Lys Thr Leu Val Glu Thr Lys Lys Thr
            100                 105                 110

Val Ala Leu Val Val Asp Leu Phe Gly Thr Asp Ala Phe Asp Val Ala
            115                 120                 125

Asn Asp Phe Lys Val Ser Pro Tyr Ile Phe Tyr Pro Ser Thr Ala Met
        130                 135                 140

Ala Leu Ser Leu Phe Leu Tyr Leu Pro Lys Leu Asp Glu Thr Val Ser
145                 150                 155                 160

Cys Glu Tyr Thr Asp Leu Pro Asp Pro Val Gln Ile Pro Gly Cys Ile
            165                 170                 175

Pro Ile His Gly Lys Asp Leu Leu Asp Pro Val Gln Asp Arg Lys Asn
            180                 185                 190

Glu Ala Tyr Lys Trp Val Leu His His Ser Lys Arg Tyr Arg Met Ala
        195                 200                 205

Glu Gly Ile Val Ala Asn Ser Phe Lys Glu Leu Glu Gly Gly Ala Ile
            210                 215                 220

Lys Ala Leu Gln Glu Glu Glu Pro Gly Lys Pro Pro Val Tyr Pro Val
225                 230                 235                 240
```

```
Gly Pro Leu Ile Gln Met Asp Ser Gly Ser Ser Lys Ala Asp Arg
                245                 250                 255

Ser Glu Cys Leu Thr Trp Leu Asp Glu Gln Pro Arg Gly Ser Val Leu
            260                 265                 270

Tyr Ile Ser Phe Gly Ser Gly Thr Leu Ser His Glu Gln Met Ile
        275                 280                 285

Glu Leu Ala Ser Gly Leu Glu Met Ser Glu Gln Arg Phe Leu Trp Val
    290                 295                 300

Ile Arg Thr Pro Asn Asp Lys Met Ala Ser Thr Tyr Phe Asn Val
305                 310                 315                 320

Gln Asp Ser Thr Asn Pro Leu Asp Phe Leu Pro Lys Gly Phe Leu Glu
                325                 330                 335

Lys Thr Lys Gly Leu Gly Leu Val Val Pro Asn Trp Ala Pro Gln Ala
            340                 345                 350

Gln Ile Leu Gly His Gly Ser Thr Ser Gly Phe Leu Thr His Cys Gly
        355                 360                 365

Trp Asn Ser Thr Leu Glu Ser Val Val His Gly Val Pro Phe Ile Ala
    370                 375                 380

Trp Pro Leu Tyr Ala Glu Gln Lys Met Asn Ala Val Met Leu Ser Glu
385                 390                 395                 400

Asp Ile Lys Val Ala Leu Arg Pro Lys Ala Asn Glu Asn Gly Ile Val
                405                 410                 415

Gly Arg Leu Glu Ile Ala Lys Val Val Lys Gly Leu Met Glu Gly Glu
            420                 425                 430

Glu Gly Lys Val Val Arg Ser Arg Met Arg Asp Leu Lys Asp Ala Ala
        435                 440                 445

Ala Lys Val Leu Ser Glu Asp Gly Ser Ser Thr Lys Ala Leu Ala Glu
    450                 455                 460

Leu Ala Thr Lys Leu Lys Lys Val Ser Asn Asn
465                 470                 475

<210> SEQ ID NO 21
<211> LENGTH: 104
<212> TYPE: PRT
<213> ORGANISM: Pseudomonas putida

<400> SEQUENCE: 21

Met Thr Val Lys Trp Ile Glu Ala Val Ala Leu Ser Asp Ile Leu Glu
1               5                   10                  15

Gly Asp Val Leu Gly Val Thr Val Glu Gly Lys Glu Leu Ala Leu Tyr
            20                  25                  30

Glu Val Glu Gly Glu Ile Tyr Ala Thr Asp Asn Leu Cys Thr His Gly
        35                  40                  45

Ser Ala Arg Met Ser Asp Gly Tyr Leu Glu Gly Arg Glu Ile Glu Cys
    50                  55                  60

Pro Leu His Gln Gly Arg Phe Asp Val Cys Thr Gly Lys Ala Leu Cys
65                  70                  75                  80

Ala Pro Val Thr Gln Asn Ile Lys Thr Tyr Pro Val Lys Ile Glu Asn
                85                  90                  95

Leu Arg Val Met Ile Asp Leu Ser
            100

<210> SEQ ID NO 22
<211> LENGTH: 449
<212> TYPE: PRT
```

-continued

<213> ORGANISM: Pseudomonas putida

<400> SEQUENCE: 22

Met Asn Tyr Asn Asn Lys Ile Leu Val Ser Glu Gly Leu Ser Gln
1               5                   10                  15

Lys His Leu Ile His Gly Asp Glu Glu Leu Phe Gln His Glu Leu Lys
            20                  25                  30

Thr Ile Phe Ala Arg Asn Trp Leu Phe Leu Thr His Asp Ser Leu Ile
        35                  40                  45

Pro Ala Pro Gly Asp Tyr Val Thr Ala Lys Met Gly Ile Asp Glu Val
    50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Phe
            340                 345                 350

Gly Pro Ala Gly Phe Trp Glu Ser Asp Asp Asn Asp Asn Met Glu Thr
        355                 360                 365

Ala Ser Gln Asn Gly Lys Lys Tyr Gln Ser Arg Asp Ser Asp Leu Leu
    370                 375                 380

Ser Asn Leu Gly Phe Gly Glu Asp Val Tyr Gly Asp Ala Val Tyr Pro
385                 390                 395                 400

```
Gly Val Val Gly Lys Ser Ala Ile Gly Glu Thr Ser Tyr Arg Gly Phe
                405                 410                 415

Tyr Arg Ala Tyr Gln Ala His Val Ser Ser Asn Trp Ala Glu Phe
            420                 425                 430

Glu His Ala Ser Ser Thr Trp His Thr Glu Leu Thr Lys Thr Thr Asp
        435                 440                 445

Arg
```

<210> SEQ ID NO 23
<211> LENGTH: 194
<212> TYPE: PRT
<213> ORGANISM: Pseudomonas putida

<400> SEQUENCE: 23

```
Met Met Ile Asn Ile Gln Glu Asp Lys Leu Val Ser Ala His Asp Ala
1               5                   10                  15

Glu Glu Ile Leu Arg Phe Phe Asn Cys His Asp Ser Ala Leu Gln Gln
            20                  25                  30

Glu Ala Thr Thr Leu Leu Thr Gln Glu Ala His Leu Leu Asp Ile Gln
        35                  40                  45

Ala Tyr Arg Ala Trp Leu Glu His Cys Val Gly Ser Glu Val Gln Tyr
    50                  55                  60

Gln Val Ile Ser Arg Glu Leu Arg Ala Ala Ser Glu Arg Arg Tyr Lys
65                  70                  75                  80

Leu Asn Glu Ala Met Asn Val Tyr Asn Glu Asn Phe Gln Gln Leu Lys
                85                  90                  95

Val Arg Val Glu His Gln Leu Asp Pro Gln Asn Trp Gly Asn Ser Pro
            100                 105                 110

Lys Leu Arg Phe Thr Arg Phe Ile Thr Asn Val Gln Ala Ala Met Asp
        115                 120                 125

Val Asn Asp Lys Glu Leu Leu His Ile Arg Ser Asn Val Ile Leu His
    130                 135                 140

Arg Ala Arg Arg Gly Asn Gln Val Asp Val Phe Tyr Ala Ala Arg Glu
145                 150                 155                 160

Asp Lys Trp Lys Arg Gly Glu Gly Val Arg Lys Leu Val Gln Arg
                165                 170                 175

Phe Val Asp Tyr Pro Glu Arg Ile Leu Gln Thr His Asn Leu Met Val
            180                 185                 190

Phe Leu
```

<210> SEQ ID NO 24
<211> LENGTH: 328
<212> TYPE: PRT
<213> ORGANISM: Pseudomonas putida

<400> SEQUENCE: 24

```
Met Glu Leu Leu Ile Gln Pro Asn Asn Arg Ile Ile Pro Phe Ser Ala
1               5                   10                  15

Gly Ala Asn Leu Leu Glu Val Leu Arg Glu Asn Gly Val Ala Ile Ser
            20                  25                  30

Tyr Ser Cys Leu Ser Gly Arg Cys Gly Thr Cys Arg Cys Arg Val Ile
        35                  40                  45

Asp Gly Ser Val Ile Asp Ser Gly Ala Glu Asn Gly Gln Ser Asn Leu
    50                  55                  60

Thr Asp Lys Gln Tyr Val Leu Ala Cys Gln Ser Val Leu Thr Gly Asn
65                  70                  75                  80
```

```
Cys Ala Ile Glu Val Pro Glu Ala Asp Glu Ile Val Thr His Pro Ala
                85                  90                  95

Arg Ile Ile Lys Gly Thr Val Val Ala Val Glu Ser Pro Thr His Asp
            100                 105                 110

Ile Arg Arg Leu Arg Val Arg Leu Ser Lys Pro Phe Glu Phe Ser Pro
        115                 120                 125

Gly Gln Tyr Ala Thr Leu Gln Phe Ser Pro Glu His Ala Arg Pro Tyr
    130                 135                 140

Ser Met Ala Gly Leu Pro Asp Asp Gln Glu Met Glu Phe His Ile Arg
145                 150                 155                 160

Lys Val Pro Gly Gly Arg Val Thr Glu Tyr Val Phe Glu His Val Arg
                165                 170                 175

Glu Gly Thr Ser Ile Lys Leu Ser Gly Pro Leu Gly Thr Ala Tyr Leu
            180                 185                 190

Arg Gln Lys His Thr Gly Pro Met Leu Cys Val Gly Gly Thr Gly Gly
        195                 200                 205

Leu Ala Pro Val Leu Ser Ile Val Arg Gly Ala Leu Lys Ser Gly Met
    210                 215                 220

Thr Asn Pro Ile Leu Leu Tyr Phe Gly Val Arg Ser Gln Gln Asp Leu
225                 230                 235                 240

Tyr Asp Ala Glu Arg Leu His Lys Leu Ala Ala Asp His Pro Gln Leu
                245                 250                 255

Thr Val His Thr Val Ile Ala Thr Gly Pro Ile Asn Glu Gly Gln Arg
            260                 265                 270

Ala Gly Leu Ile Thr Asp Val Ile Glu Lys Asp Ile Leu Ser Leu Ala
        275                 280                 285

Gly Trp Arg Ala Tyr Leu Cys Gly Ala Pro Ala Met Val Glu Ala Leu
    290                 295                 300

Cys Thr Val Thr Lys His Leu Gly Ile Ser Pro Glu His Ile Tyr Ala
305                 310                 315                 320

Asp Ala Phe Tyr Pro Gly Gly Ile
                325

<210> SEQ ID NO 25
<211> LENGTH: 450
<212> TYPE: PRT
<213> ORGANISM: Bacillus circulans

<400> SEQUENCE: 25

Met Ser Ile His Met Phe Pro Ser Asp Phe Lys Trp Gly Val Ala Thr
1               5                   10                  15

Ala Ala Tyr Gln Ile Glu Gly Ala Tyr Asn Glu Asp Gly Arg Gly Met
            20                  25                  30

Ser Ile Trp Asp Thr Phe Ala His Thr Pro Gly Lys Val Lys Asn Gly
        35                  40                  45

Asp Asn Gly Asn Val Ala Cys Asp Ser Tyr His Arg Val Glu Glu Asp
    50                  55                  60

Val Gln Leu Leu Lys Asp Leu Gly Val Lys Val Tyr Arg Phe Ser Ile
65                  70                  75                  80

Ser Trp Pro Arg Val Leu Pro Gln Gly Thr Gly Glu Val Asn Arg Ala
                85                  90                  95

Gly Leu Asp Tyr Tyr His Arg Leu Val Asp Glu Leu Leu Ala Asn Gly
            100                 105                 110

Ile Glu Pro Phe Cys Thr Leu Tyr His Trp Asp Leu Pro Gln Ala Leu
```

115                 120                 125
Gln Asp Gln Gly Gly Trp Gly Ser Arg Ile Thr Ile Asp Ala Phe Ala
            130                 135                 140
Glu Tyr Ala Glu Leu Met Phe Lys Glu Leu Gly Gly Lys Ile Lys Gln
145                 150                 155                 160
Trp Ile Thr Phe Asn Glu Pro Trp Cys Met Ala Phe Leu Ser Asn Tyr
                165                 170                 175
Leu Gly Val His Ala Pro Gly Asn Lys Asp Leu Gln Leu Ala Ile Asp
            180                 185                 190
Val Ser His His Leu Leu Val Ala His Gly Arg Ala Val Thr Leu Phe
        195                 200                 205
Arg Glu Leu Gly Ile Ser Gly Glu Ile Gly Ile Ala Pro Asn Thr Ser
210                 215                 220
Trp Ala Val Pro Tyr Arg Arg Thr Lys Glu Asp Met Glu Ala Cys Leu
225                 230                 235                 240
Arg Val Asn Gly Trp Ser Gly Asp Trp Tyr Leu Asp Pro Ile Tyr Phe
                245                 250                 255
Gly Glu Tyr Pro Lys Phe Met Leu Asp Trp Tyr Glu Asn Leu Gly Tyr
            260                 265                 270
Lys Pro Pro Ile Val Asp Gly Asp Met Glu Leu Ile His Gln Pro Ile
        275                 280                 285
Asp Phe Ile Gly Ile Asn Tyr Tyr Thr Ser Ser Met Asn Arg Tyr Asn
290                 295                 300
Pro Gly Glu Ala Gly Gly Met Leu Ser Ser Glu Ala Ile Ser Met Gly
305                 310                 315                 320
Ala Pro Lys Thr Asp Ile Gly Trp Glu Ile Tyr Ala Glu Gly Leu Tyr
                325                 330                 335
Asp Leu Leu Arg Tyr Thr Ala Asp Lys Tyr Gly Asn Pro Thr Leu Tyr
            340                 345                 350
Ile Thr Glu Asn Gly Ala Cys Tyr Asn Asp Gly Leu Ser Leu Asp Gly
        355                 360                 365
Arg Ile His Asp Gln Arg Ile Asp Tyr Leu Ala Met His Leu Ile
370                 375                 380
Gln Ala Ser Arg Ala Ile Glu Asp Gly Ile Asn Leu Lys Gly Tyr Met
385                 390                 395                 400
Glu Trp Ser Leu Met Asp Asn Phe Glu Trp Ala Glu Gly Tyr Gly Met
                405                 410                 415
Arg Phe Gly Leu Val His Val Asp Tyr Asp Thr Leu Val Arg Thr Pro
            420                 425                 430
Lys Asp Ser Phe Tyr Trp Tyr Lys Gly Val Ile Ser Arg Gly Trp Leu
        435                 440                 445
Asp Leu
    450

<210> SEQ ID NO 26
<211> LENGTH: 536
<212> TYPE: PRT
<213> ORGANISM: Pseudomonas aeruginosa

<400> SEQUENCE: 26

Met Ser Lys Arg Pro Asn Phe Leu Val Ile Val Ala Asp Asp Leu Gly
1               5                   10                  15
Phe Ser Asp Ile Gly Ala Phe Gly Gly Glu Ile Ala Thr Pro Asn Leu
            20                  25                  30

-continued

Asp Ala Leu Ala Ile Ala Gly Leu Arg Leu Thr Asp Phe His Thr Ala
         35                  40                  45

Ser Thr Cys Ser Pro Thr Arg Ser Met Leu Leu Thr Gly Thr Asp His
 50                  55                  60

His Ile Ala Gly Ile Gly Thr Met Ala Glu Ala Leu Thr Pro Glu Leu
 65                  70                  75                  80

Glu Gly Lys Pro Gly Tyr Gly His Leu Asn Glu Arg Val Val Ala
                 85                  90                  95

Leu Pro Glu Leu Leu Arg Glu Ala Gly Tyr Gln Thr Leu Met Ala Gly
             100                 105                 110

Lys Trp His Leu Gly Leu Lys Pro Glu Gln Thr Pro His Ala Arg Gly
         115                 120                 125

Phe Glu Arg Ser Phe Ser Leu Leu Pro Gly Ala Ala Asn His Tyr Gly
         130                 135                 140

Phe Glu Pro Pro Tyr Asp Glu Ser Thr Pro Arg Ile Leu Lys Gly Thr
145                 150                 155                 160

Pro Ala Leu Tyr Val Glu Asp Glu Arg Tyr Leu Asp Thr Leu Pro Glu
                 165                 170                 175

Gly Phe Tyr Ser Ser Asp Ala Phe Gly Asp Lys Leu Leu Gln Tyr Leu
             180                 185                 190

Lys Glu Arg Asp Gln Ser Arg Pro Phe Phe Ala Tyr Leu Pro Phe Ser
         195                 200                 205

Ala Pro His Trp Pro Leu Gln Ala Pro Arg Glu Ile Val Glu Lys Tyr
         210                 215                 220

Arg Gly Arg Tyr Asp Ala Gly Pro Glu Ala Leu Arg Gln Glu Arg Leu
225                 230                 235                 240

Ala Arg Leu Lys Glu Leu Gly Leu Val Glu Ala Asp Val Glu Ala His
                 245                 250                 255

Pro Val Leu Ala Leu Thr Arg Glu Trp Glu Ala Leu Glu Asp Glu Glu
             260                 265                 270

Arg Ala Lys Ser Ala Arg Ala Met Glu Val Tyr Ala Ala Met Val Glu
         275                 280                 285

Arg Met Asp Trp Asn Ile Gly Arg Val Val Asp Tyr Leu Arg Arg Gln
290                 295                 300

Gly Glu Leu Asp Asn Thr Phe Val Leu Phe Met Ser Asp Asn Gly Ala
305                 310                 315                 320

Glu Gly Ala Leu Leu Glu Ala Phe Pro Lys Phe Gly Pro Asp Leu Leu
                 325                 330                 335

Gly Phe Leu Asp Arg His Tyr Asp Asn Ser Leu Glu Asn Ile Gly Arg
             340                 345                 350

Ala Asn Ser Tyr Val Trp Tyr Gly Pro Arg Trp Ala Gln Ala Ala Thr
         355                 360                 365

Ala Pro Ser Arg Leu Tyr Lys Ala Phe Thr Thr Gln Gly Gly Ile Arg
370                 375                 380

Val Pro Ala Leu Val Arg Tyr Pro Arg Leu Ser Arg Gln Gly Ala Ile
385                 390                 395                 400

Ser His Ala Phe Ala Thr Val Met Asp Val Thr Pro Thr Leu Leu Asp
                 405                 410                 415

Leu Ala Gly Val Arg His Pro Gly Lys Arg Trp Arg Gly Arg Glu Ile
             420                 425                 430

Ala Glu Pro Arg Gly Arg Ser Trp Leu Gly Trp Leu Ser Gly Glu Thr
         435                 440                 445

Glu Ala Ala His Asp Glu Asn Thr Val Thr Gly Trp Glu Leu Phe Gly

```
            450                 455                 460
Met Arg Ala Ile Arg Gln Gly Asp Trp Lys Ala Val Tyr Leu Pro Ala
465                 470                 475                 480

Pro Val Gly Pro Ala Thr Trp Gln Leu Tyr Asp Leu Ala Arg Asp Pro
                    485                 490                 495

Gly Glu Ile His Asp Leu Ala Asp Ser Gln Pro Gly Lys Leu Ala Glu
                500                 505                 510

Leu Ile Glu His Trp Lys Arg Tyr Val Ser Glu Thr Gly Val Val Glu
                515                 520                 525

Gly Ala Ser Pro Phe Leu Val Arg
                530                 535

<210> SEQ ID NO 27
<211> LENGTH: 497
<212> TYPE: PRT
<213> ORGANISM: Escherichia coli

<400> SEQUENCE: 27

Met Lys Arg Pro Asn Phe Leu Phe Val Met Thr Asp Thr Gln Ala Thr
1               5                   10                  15

Asn Met Val Gly Cys Tyr Ser Gly Lys Pro Leu Asn Thr Gln Asn Ile
                20                  25                  30

Asp Ser Leu Ala Ala Glu Gly Ile Arg Phe Asn Ser Ala Tyr Thr Cys
            35                  40                  45

Ser Pro Val Cys Thr Pro Ala Arg Ala Gly Leu Phe Thr Gly Ile Tyr
        50                  55                  60

Ala Asn Gln Ser Gly Pro Trp Thr Asn Asn Val Ala Pro Gly Lys Asn
65                  70                  75                  80

Ile Ser Thr Met Gly Arg Tyr Phe Lys Asp Ala Gly Tyr His Thr Cys
                85                  90                  95

Tyr Ile Gly Lys Trp His Leu Asp Gly His Asp Tyr Phe Gly Thr Gly
                100                 105                 110

Glu Cys Pro Pro Glu Trp Asp Ala Asp Tyr Trp Phe Asp Gly Ala Asn
            115                 120                 125

Tyr Leu Ser Glu Leu Thr Glu Lys Glu Ile Ser Leu Trp Arg Asn Gly
        130                 135                 140

Leu Asn Ser Val Glu Asp Leu Gln Ala Asn His Ile Asp Glu Thr Phe
145                 150                 155                 160

Thr Trp Ala His Arg Ile Ser Asn Arg Ala Val Asp Phe Leu Gln Gln
                165                 170                 175

Pro Ala Arg Ala Asp Glu Pro Phe Leu Met Val Val Ser Tyr Asp Glu
            180                 185                 190

Pro His His Pro Phe Thr Cys Pro Val Glu Tyr Leu Glu Lys Tyr Ala
        195                 200                 205

Asp Phe Tyr Tyr Glu Leu Gly Glu Lys Ala Gln Asp Asp Leu Ala Asn
        210                 215                 220

Lys Pro Glu His His Arg Leu Trp Ala Gln Ala Met Pro Ser Pro Val
225                 230                 235                 240

Gly Asp Asp Gly Leu Tyr His His Pro Leu Tyr Phe Ala Cys Asn Asp
                245                 250                 255

Phe Val Asp Asp Gln Ile Gly Arg Val Ile Asn Ala Leu Thr Pro Glu
            260                 265                 270

Gln Arg Glu Asn Thr Trp Val Ile Tyr Thr Ser Asp His Gly Glu Met
        275                 280                 285
```

```
Met Gly Ala His Lys Leu Ile Ser Lys Gly Ala Ala Met Tyr Asp Asp
    290                 295                 300

Ile Thr Arg Ile Pro Leu Ile Arg Ser Pro Gln Gly Glu Arg Arg
305                 310                 315                 320

Gln Val Asp Thr Pro Val Ser His Ile Asp Leu Leu Pro Thr Met Met
                325                 330                 335

Ala Leu Ala Asp Ile Glu Lys Pro Glu Ile Leu Pro Gly Glu Asn Ile
                340                 345                 350

Leu Ala Val Lys Glu Pro Arg Gly Val Met Val Glu Phe Asn Arg Tyr
                355                 360                 365

Glu Ile Glu His Asp Ser Phe Gly Gly Phe Ile Pro Val Arg Cys Trp
370                 375                 380

Val Thr Asp Asp Phe Lys Leu Val Leu Asn Leu Phe Thr Ser Asp Glu
385                 390                 395                 400

Leu Tyr Asp Arg Arg Asn Asp Pro Asn Glu Met His Asn Leu Ile Asp
                405                 410                 415

Asp Ile Arg Phe Ala Asp Val Arg Ser Lys Met His Asp Ala Leu Leu
                420                 425                 430

Asp Tyr Met Asp Lys Ile Arg Asp Pro Phe Arg Ser Tyr Gln Trp Ser
                435                 440                 445

Leu Arg Pro Trp Arg Lys Asp Ala Arg Pro Arg Trp Met Gly Ala Phe
450                 455                 460

Arg Pro Arg Pro Gln Asp Gly Tyr Ser Pro Val Val Arg Asp Tyr Asp
465                 470                 475                 480

Thr Gly Leu Pro Thr Gln Gly Val Lys Val Glu Glu Lys Lys Gln Lys
                485                 490                 495

Phe

<210> SEQ ID NO 28
<211> LENGTH: 571
<212> TYPE: PRT
<213> ORGANISM: Providencia stuartii

<400> SEQUENCE: 28

Met Lys Lys Thr Leu Leu Ala Ile Ala Leu Ser Ser Val Met Ser Gly
1               5                   10                  15

Val Ala Leu Gly Glu Val Asp Asp Arg Pro Asn Val Leu Ile Ile Ile
                20                  25                  30

Ala Asp Asp Met Gly Tyr Ser Asp Ile Ser Pro Phe Gly Gly Glu Ile
                35                  40                  45

Pro Thr Pro Asn Leu Gln Lys Met Ala Glu Gln Gly Val Arg Met Ser
    50                  55                  60

Gln Tyr Tyr Thr Ser Pro Met Ser Ala Pro Ala Arg Ser Met Leu Met
65                  70                  75                  80

Thr Gly Ala Thr Asn Gln Gln Ala Gly Met Gly Gly Met Trp Trp Tyr
                85                  90                  95

Glu Asn Thr Val Gly Lys Pro Gly Tyr Glu Leu Arg Leu Thr Asp Arg
                100                 105                 110

Val Val Thr Met Ala Glu Arg Phe Gln Asp Ala Gly Tyr Asn Thr Leu
                115                 120                 125

Met Ser Gly Lys Trp His Leu Gly Tyr Thr Lys Gly Ala Arg Pro Thr
                130                 135                 140

Asp Arg Gly Phe Asn Gln Ala Phe Ala Phe Met Gly Gly Gly Thr Ser
145                 150                 155                 160
```

```
His Phe Asp Asp Ala Lys Pro Leu Gly Thr Val Glu Ser Phe His Thr
            165                 170                 175
Tyr Tyr Thr Leu Asn Gly Glu Lys Val Ser Leu Pro Ser Asp Phe Tyr
        180                 185                 190
Ser Ser Lys Asn Tyr Ala Gln Gln Leu Glu Gln Trp Ile Lys Gln Thr
        195                 200                 205
Pro Ser Asp Gln Pro Ile Phe Ala Tyr Leu Ala Phe Thr Ala Pro His
    210                 215                 220
Asp Pro Ile Gln Ala Pro Asp Asp Trp Ile Arg Lys Phe Asp Gly Lys
225                 230                 235                 240
Tyr Asp Glu Gly Phe Gly Lys Ile Tyr Arg Gln Arg Ile Asn Arg Leu
                245                 250                 255
Lys Glu Leu Gly Ile Ile Asn Asp Lys Thr Pro Met Pro Lys Leu Asn
            260                 265                 270
Leu Asp Lys Glu Trp Glu Gln Leu Thr Pro Glu Glu Lys Arg Tyr Ala
        275                 280                 285
Ala Lys Thr Met Gln Val Tyr Ala Ala Met Ile Ala Tyr Met Asp Asp
        290                 295                 300
Gln Ile Gly Gly Val Ile Asn Thr Leu Lys Glu Thr Gly Arg Asp Lys
305                 310                 315                 320
Asn Thr Ile Ile Ile Phe Ala Thr Asp Asn Gly Ala Asn Pro Ala Ser
                325                 330                 335
Gly Phe Tyr Tyr Glu Ser Asp Pro Glu Tyr Trp Lys Gln Phe Asp Asn
            340                 345                 350
Ser Tyr Glu Asn Leu Gly Arg Lys Asn Ser Phe Val Ser Val Gly Pro
        355                 360                 365
Gln Trp Ala Asn Val Ser Asn Ala Pro Tyr Ala Asn Tyr His Lys Thr
    370                 375                 380
Thr Ser Ala Gln Gly Gly Ile Asn Thr Asp Leu Ile Ile Thr Gly Pro
385                 390                 395                 400
Gly Ile Gly Lys Ala Gly Ser Ile Asp Lys Thr Pro Met Ala Val Tyr
                405                 410                 415
Asp Ile Ala Pro Thr Leu Tyr Glu Phe Ala Gly Ile Asp Ala Asn Lys
            420                 425                 430
Gln Ile Lys Asn Ile His Pro Leu Pro Met Leu Gly Thr Ser Phe Lys
        435                 440                 445
Ser His Phe Leu Gly Lys Ser Thr Val Asn Pro Arg Gln Leu Phe Gly
    450                 455                 460
Val Glu Leu His Asn Gln Ala Ala Leu Val Glu Gly Asp Trp Lys Leu
465                 470                 475                 480
Arg Arg Leu Val Lys Ala Ser Pro Lys Ala Glu Met Ala Pro Trp Gln
                485                 490                 495
Leu Phe Asn Leu Lys Glu Asp Pro Leu Glu Thr Arg Asp Leu Ala Ala
            500                 505                 510
Lys His Pro Glu Ile Val Gln Lys Leu Gln Lys Tyr Glu Gln Phe
        515                 520                 525
Ala Lys Thr Gly Met Ile Ile Glu Ala Lys Gly Glu Ala Ile Asp Tyr
        530                 535                 540
Ile Gly Val Asp Glu Ser Thr Gly Asn Tyr Ile Gly Ile Asp Pro Lys
545                 550                 555                 560
Thr Asn Lys Arg Ile Glu Pro Ala Lys Val Lys
                565                 570
```

<210> SEQ ID NO 29
<211> LENGTH: 395
<212> TYPE: PRT
<213> ORGANISM: Providencia stuartii

<400> SEQUENCE: 29

```
Met Lys Ile Ser Phe Tyr Asp Pro Pro Arg Leu Gln Gly Lys Ser Leu
1               5                   10                  15

Lys Ser Ala Ile Pro Phe His Ile Leu Leu Lys Pro Val Gly Ser Gly
            20                  25                  30

Cys Asn Leu Lys Cys Asp Tyr Cys Tyr Tyr Pro Gln His Asn Glu Gln
        35                  40                  45

Lys Ala Ala Pro Met Leu Lys Ala Met Leu Glu Pro Phe Ile Lys Asn
50                  55                  60

Tyr Ile Ala Ala Gln Pro Ala Tyr Thr Lys Glu Ile Asn Phe Val Trp
65                  70                  75                  80

Gln Gly Gly Glu Pro Leu Leu Ala Gly Leu Asp Phe Tyr Lys Arg Ala
                85                  90                  95

Ile Ala Leu Gln Gln Lys Tyr Ala Pro His Gly Val Arg Ile Ile Asn
            100                 105                 110

Thr Leu Gln Thr Asn Ala Thr Leu Leu Thr Pro Ser Trp Cys Arg Phe
        115                 120                 125

Leu Lys Gln His Asp Phe Val Ile Gly Val Ser Leu Asp Gly Pro Glu
130                 135                 140

Ser Ile His Asp Gln Tyr Arg His Asp Arg Arg Gly Asn Ser Gly Ser
145                 150                 155                 160

Tyr Ala Ser Val Ile Lys Gly Ile Ala Leu Leu Gln Gln Phe Asp Ile
                165                 170                 175

Glu Phe Asn Ile Leu Thr Val Val His Asp Gly Val Ala His Leu Gly
            180                 185                 190

Lys Glu Ile Tyr Leu His Phe Val Gln Leu Gly Ile Arg Tyr Ile Gln
        195                 200                 205

Phe Gln Pro Leu Met Leu Glu Gly Asp Ala Ile His Gln Gly Phe Thr
210                 215                 220

Leu Ser Ala Asn Asn Trp Gly Leu Phe Leu Ser Ser Val Tyr Gln Gln
225                 230                 235                 240

Trp Gln Ala Ser Gly His Ile Gly Arg Val Phe Val Met Asn Ile Glu
                245                 250                 255

Gln Val Tyr Ser Gln Tyr Phe Thr Gln Val Ser Ser Thr Cys Val His
            260                 265                 270

Ser Glu Arg Cys Gly Thr Asn Met Met Met Glu Thr Gln Gly Glu Ile
        275                 280                 285

Tyr Ala Cys Asp His Gln Ala Asn Gln Ser His Tyr Leu Gly Gln Phe
290                 295                 300

Asn Gly Gln Gln Gly Phe Ser Asp Phe Val Glu Ala Ser Ile Ser Leu
305                 310                 315                 320

Pro Phe Gly Gln Asn Lys Ser Arg Arg Lys Glu Cys Gln Gln Cys Ser
                325                 330                 335

Val Lys Met Val Cys Gln Gly Gly Cys Pro Ala His Leu Asn Gln Phe
            340                 345                 350

Gly Arg Asn Gln Leu Cys Glu Gly Tyr Phe Ala Phe Phe Ser Leu Val
        355                 360                 365

Leu Ala Pro Ile Arg Gln Tyr Gln Arg Asn Ala Gln Gly Val Gln His
370                 375                 380
```

Trp Arg Asn Ala Phe Leu Lys Asn Ala Val Ala
385                 390                 395

<210> SEQ ID NO 30
<211> LENGTH: 579
<212> TYPE: PRT
<213> ORGANISM: Neurospora crassa

<400> SEQUENCE: 30

Met Ser Ser His Gly Ser His Asp Gly Ala Ser Thr Glu Lys His Leu
1               5                   10                  15

Ala Thr His Asp Ile Ala Pro Thr His Asp Ala Ile Lys Ile Val Pro
            20                  25                  30

Lys Gly His Gly Gln Thr Ala Thr Lys Pro Gly Ala Gln Glu Lys Glu
        35                  40                  45

Val Arg Asn Ala Ala Leu Phe Ala Ile Lys Glu Ser Asn Ile Lys
    50                  55                  60

Pro Trp Ser Lys Glu Ser Ile His Leu Tyr Phe Ala Ile Phe Val Ala
65                  70                  75                  80

Phe Cys Cys Ala Cys Ala Asn Gly Tyr Asp Gly Ser Leu Met Thr Gly
                85                  90                  95

Ile Ile Ala Met Asp Lys Phe Gln Asn Gln Phe His Thr Gly Asp Thr
            100                 105                 110

Gly Pro Lys Val Ser Val Ile Phe Ser Leu Tyr Thr Val Gly Ala Met
        115                 120                 125

Val Gly Ala Pro Phe Ala Ala Ile Leu Ser Asp Arg Phe Gly Arg Lys
130                 135                 140

Lys Gly Met Phe Ile Gly Gly Ile Phe Ile Ile Val Gly Ser Ile Ile
145                 150                 155                 160

Val Ala Ser Ser Ser Lys Leu Ala Gln Phe Val Val Gly Arg Phe Val
                165                 170                 175

Leu Gly Leu Gly Ile Ala Ile Met Thr Val Ala Ala Pro Ala Tyr Ser
            180                 185                 190

Ile Glu Ile Ala Pro Pro His Trp Arg Gly Arg Cys Thr Gly Phe Tyr
        195                 200                 205

Asn Cys Gly Trp Phe Gly Gly Ser Ile Pro Ala Ala Cys Ile Thr Tyr
210                 215                 220

Gly Cys Tyr Phe Ile Lys Ser Asn Trp Ser Trp Arg Ile Pro Leu Ile
225                 230                 235                 240

Leu Gln Ala Phe Thr Cys Leu Ile Val Met Ser Ser Val Phe Phe Leu
                245                 250                 255

Pro Glu Ser Pro Arg Phe Leu Phe Ala Asn Gly Arg Asp Ala Glu Ala
            260                 265                 270

Val Ala Phe Leu Val Lys Tyr His Gly Asn Gly Asp Pro Asn Ser Lys
        275                 280                 285

Leu Val Leu Leu Glu Thr Glu Glu Met Arg Asp Gly Ile Arg Thr Asp
290                 295                 300

```
Gly Val Asp Lys Val Trp Trp Asp Tyr Arg Pro Leu Phe Met Thr His
305                 310                 315                 320

Ser Gly Arg Trp Arg Met Ala Gln Val Leu Met Ile Ser Ile Phe Gly
            325                 330                 335

Gln Phe Ser Gly Asn Gly Leu Gly Tyr Phe Asn Thr Val Ile Phe Lys
            340                 345                 350

Asn Ile Gly Val Thr Ser Thr Ser Gln Gln Leu Ala Tyr Asn Ile Leu
            355                 360                 365

Asn Ser Val Ile Ser Ala Ile Gly Ala Leu Thr Ala Val Ser Met Thr
370                 375                 380

Asp Arg Met Pro Arg Arg Ala Val Leu Ile Ile Gly Thr Phe Met Cys
385                 390                 395                 400

Ala Ala Ala Leu Ala Thr Asn Ser Gly Leu Ser Ala Thr Leu Asp Lys
            405                 410                 415

Gln Thr Gln Arg Gly Thr Gln Ile Asn Leu Asn Gln Gly Met Asn Glu
            420                 425                 430

Gln Asp Ala Lys Asp Asn Ala Tyr Leu His Val Asp Ser Asn Tyr Ala
            435                 440                 445

Lys Gly Ala Leu Ala Ala Tyr Phe Leu Phe Asn Val Ile Phe Ser Phe
450                 455                 460

Thr Tyr Thr Pro Leu Gln Gly Val Ile Pro Thr Glu Ala Leu Glu Thr
465                 470                 475                 480

Thr Ile Arg Gly Lys Gly Leu Ala Leu Ser Gly Phe Ile Val Asn Ala
            485                 490                 495

Met Gly Phe Ile Asn Gln Phe Ala Gly Pro Ile Ala Leu His Asn Ile
            500                 505                 510

Gly Tyr Lys Tyr Ile Phe Val Phe Val Gly Trp Asp Leu Ile Glu Thr
            515                 520                 525

Val Ala Trp Tyr Phe Phe Gly Val Glu Ser Gln Gly Arg Thr Leu Glu
530                 535                 540

Gln Leu Glu Trp Val Tyr Asp Gln Pro Asn Pro Val Lys Ala Ser Leu
545                 550                 555                 560

Lys Val Glu Lys Val Val Val Gln Ala Asp Gly His Val Ser Glu Ala
            565                 570                 575

Ile Val Ala
```